US011512303B2

(12) United States Patent
Chen et al.

(10) Patent No.: US 11,512,303 B2
(45) **Date of Patent: *Nov. 29, 2022**

(54) ENGINEERED POLYPEPTIDES AND THEIR APPLICATIONS IN THE SYNTHESIS OF BETA-HYDROXY-ALPHA-AMINO ACIDS

(71) Applicant: Enzymaster (Ningbo) Bio-Engineering Co., Ltd, Ningbo (CN)

(72) Inventors: Haibin Chen, Ningbo (CN); Yong Koy Bong, Ningbo (CN); Qing Xu, Ningbo (CN); Ameng Zhou, Ningbo (CN); Tianran Shen, Ningbo (CN); Jiadong Yang, Ningbo (CN); Zhuhong Yang, Ningbo (CN)

(73) Assignee: ENZYMASTER (NINGBO) BIO-ENGINEERING CO., LTD., Ningbo (CN)

( * ) Notice: Subject to any disclaimer, the term of this patent is extended or adjusted under 35 U.S.C. 154(b) by 55 days.

This patent is subject to a terminal disclaimer.

(21) Appl. No.: 16/615,120

(22) PCT Filed: May 9, 2018

(86) PCT No.: PCT/CN2018/086227

§ 371 (c)(1),
(2) Date: Nov. 19, 2019

(87) PCT Pub. No.: WO2018/219107

PCT Pub. Date: Dec. 6, 2018

(65) Prior Publication Data

US 2021/0284987 A1 Sep. 16, 2021

(30) Foreign Application Priority Data

May 27, 2017 (CN) ......................... 201710386994.9

(51) Int. Cl.
*C12P 13/04* (2006.01)
*C12N 9/88* (2006.01)
*C12N 1/15* (2006.01)
*C12N 11/00* (2006.01)

(52) U.S. Cl.
CPC ................ *C12N 9/88* (2013.01); *C12N 11/00* (2013.01); *C12P 13/04* (2013.01); *C12Y 401/02048* (2013.01)

(58) Field of Classification Search
CPC ..... C12Y 401/02048; C12Y 202/01002; C12P 13/04; C12N 9/88; C12N 11/00; C12N 9/1096; C12N 15/70; C12N 9/0008; C12N 9/1029; C12N 9/18
USPC .................. 435/193, 106, 128, 252.3, 320.1
See application file for complete search history.

(56) References Cited

FOREIGN PATENT DOCUMENTS

| | | | |
|---|---|---|---|
| CA | 2648697 | A1 | 10/2007 |
| CN | 104673814 | A | 6/2015 |
| EP | 0460883 | A2 | 12/1991 |
| JP | 2006/121983 | A | 5/2006 |

OTHER PUBLICATIONS

BAD91544.1 phenylserine aldolase [Pseudomonas putida], GenBank (Aug. 10, 2005).
Fesko, K. et al., "Threonine aldolase perspectives in engineering and screening the enzymes with enhanced substrate and stereo specificities", *Appl. Microbiol. Biotechnol.*, vol. 100, pp. 2579-2590 (Jan. 26, 2016).
Gwon, H.J. et al., "Diastereoselective synthesis of L-threo-3, 4-dihydroxyphenylserine by low-specific L-threonine aldolase mutants", *Biotechnol. Lett.*, vol. 32, pp. 143-149 (Sep. 17, 2009).
Lee, S.J. et al., "High-throughput screening methods for selecting 1-threonine aldolases with improved activity", Journal of Molecular Catalysis B: Enzymatic, vol. 26, pp. 265-272 (Dec. 31, 2003).

*Primary Examiner* — Robert B Mondesi
*Assistant Examiner* — Mohammad Y Meah
(74) *Attorney, Agent, or Firm* — Smith Patent, LLC; Chalin A. Smith

(57) ABSTRACT

The present invention provides engineered polypeptides that are useful for the asymmetric synthesis of β-hydroxy-α-amino acids under industrial-relevant conditions. The engineered polypeptides disclosed in this invention were developed through directed evolution based on the ability of catalytic synthesis of (2S, 3R)-2-amino-3-hydroxy-3-(4-nitrophenyl) propanoic acid. The present disclosure also provides polynucleotides encoding engineered polypeptides, host cells capable of expressing engineered polypeptides, and methods of producing β-hydroxy-α-amino acids using engineered polypeptides. Compared to other processes of preparation, the use of the engineered polypeptides of the present invention for the preparation of β-hydroxy-α-amino acids results in high purity of the desired stereoisomers, mild reaction conditions, low pollution and low energy consumption. So, it has good industrial application prospects.

19 Claims, No Drawings

Specification includes a Sequence Listing.

ENGINEERED POLYPEPTIDES AND THEIR APPLICATIONS IN THE SYNTHESIS OF BETA-HYDROXY-ALPHA-AMINO ACIDS

PRIORITY

This application corresponds to the U.S. National phase of International Application No. PCT/CN2018/086227, filed May 9, 2018, which, in turn, claims priority to Chinese Patent Application No. 2017 10386994.9 filed May 27, 2017, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Aug. 21, 2019, is named LNK_203US_SEQ_listing.txt and is 552,072 bytes in size.

TECHNICAL FIELD

The present invention relates to the field of biotechnology, in particular to engineered aldolase polypeptides and their application in industrial biocatalysis.

BACKGROUND TECHNIQUE

β-hydroxy-α-amino acids are a kind of important amino acids which are critical intermediates to construct a variety of natural products and drugs. They have many important biological activities. The chemical structure of these compounds generally has two chiral centers with multiple stereoisomers (Scheme 1). (2S, 3R)-2-amino-3-hydroxy-3-(4-nitrophenyl) propanoic acid (a compound of formula A2 as shown in Scheme 2), is a β-hydroxy-α-amino acid and is available as an intermediate in the synthesis of D-(−)-threo-2-amino-1-(4-nitrophenyl)-1,3-propanediol.

At present, there are two main routes in the synthesis of D-(−)-threo-2-amino-1-(4-nitrophenyl)-1,3-propanediol (or Levoamine): p-nitrobenzaldehyde or p-nitro-acetophenone is used as the starting material respectively. Using p-nitrobenzaldehyde as the starting material requires less number of substrates and is a relatively simpler process. However, due to the presence of multiple isomeric structures, this route requires excessive p-nitrobenzaldehyde; it also requires calcium borohydride as reducing agent which is very expensive. Therefore, the current industrial process is mainly the second route. P-nitro-acetophenone is subject to bromination, amination, acylation, formaldehyde condensation, reduction and hydrolysis to produce racemic product which is then resoluted by tartaric acid to obtain D-(−)-threo-2-amino-1-(4-nitrophenyl)-1,3-propanediol. This process uses a lot of irritating organic solvents such as acetic anhydride, benzyl chloride, acetic acid, bromine, giving terrible environmental impact and also making it very difficult to manage the production site. And this synthesis process consists of many steps including protection, deprotection, resolution, etc, which is tedious and makes overall yield low.

It has been reported that aldolase can condense aldehydes and amino acids to form β-hydroxy-α-amino acids. The condition of this enzymatic reaction is mild and its pollution is little, but the stereoselectivity of wild-type aldolases s is not good enough to meet industrial application request. The present invention provides a series of engineered polypeptides which high stereoselectivity. These engineered polypeptides were developed through directed evolution towards the selection of (2S, 3R)-2-amino-3-hydroxy-3-(4-nitrophenyl) propanoic acid. According to the enzymatic process disclosed by this invention, p-nitrobenzaldehyde and glycine are directly and selectively condensed into (2S, 3R)-2-amino-3-hydroxy-3-(4-nitrophenyl) propanoic acid, thus determining two chiral centers in one step. (2S, 3R)-2-amino-3-hydroxy-3-(4-nitrophenyl) propanoic acid can be simply esterified and reduced to give D-(−)-threo-2-amino-1-(4-nitrophenyl)-1,3-propanediol. This entire process is simple and easy to operate, and does not require chemical resolution, effectively reducing production cost. At the same time, the condition of enzyme-catalyzed reaction is mild without requiring strong acid, alkali, high temperature or high pressure environment, alleviating the requirements of production equipment, effectively guaranteeing the quality of products, enabling economical and environmental-friendly production.

BRIEF DESCRIPTION OF THE SCHEMES

Scheme 1 depicts β-hydroxy-α-amino acids.

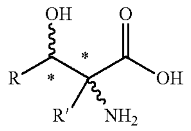

(* refers to chiral center)

Scheme 2 depicts the synthesis of A2 by an asymmetric reaction catalyzed by an engineered aldolase polypeptide of the present invention.

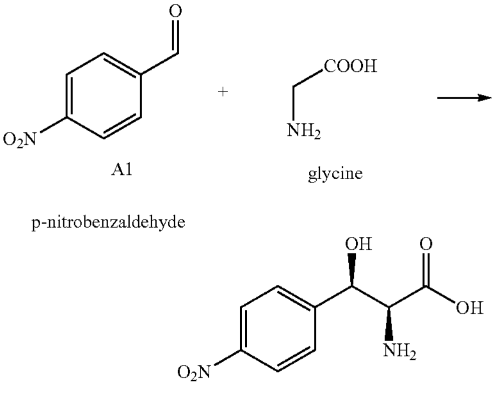

A1 glycine p-nitrobenzaldehyde

A2

(2S, 3R)-2-amino-3-hydroxy-3-(4-nitrophenyl) propanoic acid

Content of the Invention

1. Overview

The present invention provides engineered polypeptides with high stereoselectivity, high catalytic activity and good stability, which can synthesize β-hydroxy-α-amino acids asymmetrically, and in particular asymmetrically synthesize (2S, 3R)-2-amino-3-hydroxy-3-(4-nitrophenyl) propanoic acid. The present invention also provides gene sequences of engineered polypeptides, recombinant expression vectors containing the genes, engineered strains and efficient methods for the production thereof, as well as reaction processes for the asymmetric synthesis of β-hydroxy-α-amino acids using engineered polypeptides.

In the first aspect, the present invention provides engineered aldolase polypeptides with improved catalytic properties. These engineered polypeptides are derived from directed evolution of a wild-type aldolase which is less stereoselective toward the product, through substitutions, insertions, or deletions of a number of amino acid residues. The wild-type aldolase is from *Pseudomonas putida* which consists of 357 amino acids and has the sequence shown in SEQ ID No: 2. The wild-type aldolase showed low stereoselectivity for the product. As measured by the inventors, in the reaction of converting p-nitrobenzaldehyde (i.e. A1) with glycine to produce (2S, 3R)-2-amino-3-hydroxy-3-(4-nitrophenyl) propanoic acid (i.e. A2) in Scheme 2 using SEQ ID No: 2, the diastereomeric excess number (i.e. de) for A2 is ≤40%.

In some embodiments, engineered aldolase polypeptides of the present disclosure are capable of converting A1 and glycine to A2 at a stereoselectivity at least equal to or greater than that of SEQ ID No: 2. Under the indicated reaction conditions, the engineered aldolase polypeptides of the present disclosure are capable of producing at least 60%, 65%, 70%, 75%, 80%, 85%, 90%, 91%, 92%, 93% 94%, 95%, 96%, 97%, 98% or 99% or more diastereomeric excess for A2. In some embodiments, the reaction conditions include 20% organic solvent (including but not limited to dimethyl sulfoxide, ethanol or methanol) and temperature of about 30° C. and a pH of about 6.0.

In some embodiments, the engineered aldolase polypeptides are capable of converting A1 and glycine to A2 at a higher stereoselectivity than the polypeptide of SEQ ID NO: 2 under the indicated reaction conditions. The engineered aldolase polypeptides comprise an amino acid sequence that is at least 80%, 85%, 86%, 87%, 88%, 89%, 90%, 91%, 92%, 93%, 94%, 95%, 96%, 97%, 98%, 99% or more identical to the sequence of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236.

The identity between two amino acid sequences or two nucleotide sequences can be obtained by commonly used algorithms in the art and can be calculated according to default parameters by using NCBI Blastp and Blastn software, or by using the Clustal W algorithm (Nucleic Acid Research, 22 (22): 4673-4680, 1994). For example, using the Clustal W algorithm, the amino acid sequence identity of SEQ ID NO: 2 to SEQ ID NO: 184 is 93.3%.

In some embodiments, engineered aldolase polypeptides can comprise an amino acid sequence that differs in one or more residues compared to the sequence of SEQ ID NO: 2 in the residue position: X16, X17, X19, X26, X32, X33, X37, X38, X39, X41, X42, X43, X44, X45, X46, X47, X48, X49, X91, X92, X118, X132, X134, X154, X164, X168, X176, X182, X185, X189, X191, X216, X217, X218, X227, X234, X237, X244, X247, X262, X282, X284, X285, X288, X291, X292, X293, X294, X295, X302, X305, X316, X318, X319, X320, X324, X352; more specifically, engineered aldolase polypeptides comprise an amino acid sequence comprising at least one of the following features (these features are substitutions of amino acid residues with the reference sequence of SEQ ID NO: 2): D16E, N17G, N17E, A19W, A19N, A26V, A26L, H32V, S33N, A37T, A37M, A37K, G38D, G38P, G385, G38E, G38A, P39L, P39A, G41Y, T42M, D43P, D43Y, E44D, L45I, T46H, A47H, Q48L, V495, P91H, P91S, P91L, P91K, P91N, A92W, P118R, P118I, P118G, R132S, K134Q, V154G, V154S, V154A, V154F, V154R, E164R, D168N, G176P, S182A, A185T, V189S, L191H, V216C, L217W, A218C, A218S, T227P, 5234R, R237T, S244I, S244V, M247Y, M247H, L262I, E282R, E282Y, E282K, L284K, L284F, L284A, L284V, G285P, G285S, G285K, E288I, E288T, G291F, G291V, G291W, G291Y, G292K, G292V, T293P, E294K, E294M, A295G, A295Q, L302M, A305T, A305P, G316K, G316S, G316V, G316R, Y318G, Y318L, H319Y, H319V, D320K, D320E, P324L, D352Y, D352Q, D352A; Or, in addition to the abovementioned differences, engineered aldolase polypeptides comprise insertions or deletions of 1, 2, 3, 4, 5, 6, 7, 8, 9, 10, 11, 12, 13, 14, 15, 16, 18, 20, 21, 22, 23, 24, 25 or 30 of amino acid residues.

More specifically, in some embodiments, the engineered aldolase polypeptides which were improved over SEQ ID NO: 2 comprises a sequence corresponding to SEQ ID No: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236.

In another aspect, this invention provides polynucleotide sequences encoding engineered aldolase polypeptides. In some embodiments, a polynucleotide can be part of an expression vector having one or more control sequences for the expression of an engineered aldolase polypeptide. In some embodiments, polynucleotides can comprise sequences corresponding to SEQ ID No: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235.

As known to people skilled in the art, due to the degeneracy of the nucleotide codons, the polynucleotide sequences encoding amino acid sequences SEQ ID No: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236 are not limited to SEQ ID No: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235. The polynucleotide sequences of the engineered polypeptides of the present invention may also be any other polynucleotide sequences encoding amino acid sequences SEQ ID No: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236.

In another aspect, this disclosure provides polynucleotides comprising sequences encoding engineered aldolase polypeptides, expression vectors and host cells capable of expressing engineered aldolase polypeptides. In some embodiments, the host cell can be bacterial host cell, such as *E. coli*. The host cell can be used to express and isolate the engineered aldolase described herein, or alternatively be directly used in the reaction for conversion of substrates to products.

In some embodiments, the engineered aldolase in the form of whole cell, crude extract, isolated enzyme, or purified enzyme can be used alone or in an immobilized form, such as immobilization on a resin.

The present disclosure also provides the process of the asymmetric synthesis of β-hydroxy-α-amino acid compounds using the herein disclosed engineered aldolase polypeptides, the resulting β-hydroxy-α-amino acid products having the structure shown in Formula (I):

(I)

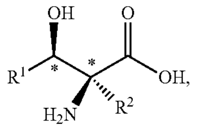

The β-hydroxy-α-amino acid products of formula (I) have the indicated stereochemical configuration shown at the chiral center marked with an*; the β-hydroxy-α-amino acid products of formula (I) are in a diastereoisomeric excess over the other isomers, where $R^1$ is optionally substituted or unsubstituted aryl or heteroaryl, or optionally substituted or unsubstituted $C_1$-$C_8$ hydrocarbyl;

$R^2$ is —H, —$CH_2OH$, —$CH_2SH$, —$CH_2SCH_3$, or optionally substituted or unsubstituted $C_1$-$C_4$ hydrocarbyl, the process comprising that, under suitable reaction conditions of reacting the aldehyde substrate and the amino acid substrate to obtain β-hydroxy-α-amino acid products, the aldehyde substrate of formula (II) and the amino acid substrate of formula (III):

(II)

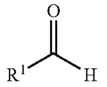

(III)

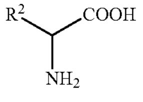

were contacted with the aldolase polypeptides, wherein the aldolase polypeptides are engineered aldolase polypeptides described herein. In some embodiments, the engineered aldolase polypeptides have at least 80%, 85%, 86%, 87%, 88%, 89%, 90%, 91%, 92%, 93%, 94%, 95%, 96%, 97%, 98%, 99% or more of sequence identity to SEQ ID NO: 2 and are capable of condensing the aldehyde substrate of formula (II) and the amino acid substrate of formula (III) to obtain the β-hydroxy-α-amino acid products of formula (I) at higher conversion or higher stereoselectivity compared to SEQ ID NO: 2.

In some embodiments, the β-hydroxy-α-amino acid product of formula (I) is present in diastereomeric excess of at least 60%, 65%, 70%, 75%, 80%, 85%, 90%, 91%, 92%, 93%, 94%, 95%, 96%, 97%, 98%, or 99% or greater.

In some embodiments of this process, the β-hydroxy-α-amino acid products of formula (I) are:

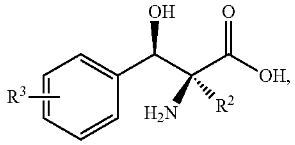

wherein $R^3$ is $C_1$-$C_4$ hydrocarbyl, —H, halogen such as —F, —Cl, —Br and —I, —$NO_2$, —NO, —$SO_2R'$ or SOR', —SR', —NR'—C(O) NR', —$SO_2NH_2$ or —$SONH_2$, —CN, $CF_3$, wherein each R' is independently selected from —H or ($C_1$-$C_4$) hydrocarbyl;

$R^3$ may also be

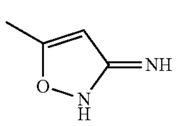

or

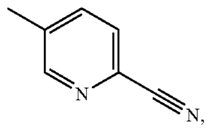

$R^2$ is —H, —$CH_3$, —$CH_2CH_3$, —CH $(CH_3)_2$, —$CH_2OH$, —$CH_2SH$ or —$CH_2SCH_3$, and the aldehyde substrate of formula (II) is:

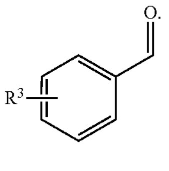

In some embodiments, $R^3$ is in the para position of the phenyl ring. In some embodiments, $R^3$ is in the meta position of the phenyl ring. In some embodiments, $R^3$ is ortho to the phenyl ring. In some embodiments, $R^3$ is both para and meta to the phenyl ring. In some embodiments, $R^3$ is both para and ortho to the phenyl ring. In some embodiments, $R^3$ is both meta and ortho to the phenyl ring.

In some embodiments of this process, the β-hydroxy-α-amino acid product of formula (I) is:

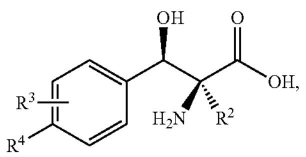

wherein $R^4$ is defined same as $R^3$ above, $R^3$ and $R^2$ are as defined above, and the aldehyde substrate of formula (II) is:

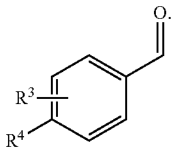

In some embodiments, $R^3$ is in the meta position of the phenyl ring. In some embodiments, $R^3$ is ortho to the phenyl ring.

In some embodiments, the engineered aldolase polypeptides can be used in the production process of diastereomeric excess of the compound of formula A2, (2S, 3R)-2-amino-3-hydroxy-3-(4-nitrophenyl) propanoic acid:

A2

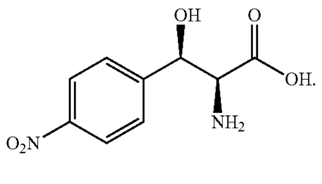

In these embodiments, the production process comprises that, under suitable reaction conditions for converting compound of formula A1 to compound of formula A2, in a suitable organic solvent, in the presence of glycine, the compound of formula A1:

A1

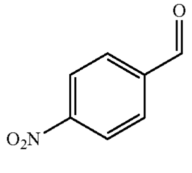

were contacted with the engineered aldolase polypeptides disclosed herein.

In some embodiments of the above process, the compound of formula (I) or the compound of formula A2 is present in a diastereomeric excess of at least 60%, 65%, 70%, 75%, 80%, 85%, 90%, 91%, 92%, 93% 94%, 95%, 96%, 97%, 98% or 99% or more.

Specific embodiments of engineered aldolase polypeptides for use in this method are further provided in the detailed description. An engineered aldolase polypeptide that can be used in the above process can comprise one or more sequences selected from the amino acid sequences corresponding to SEQ ID NOs: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236.

In another aspect, this disclosure provides a process of producing (2S, 3R) -2-amino-3-hydroxy-3-(4-nitrophenyl) propanoic acid using an engineered aldolase polypeptide disclosed herein. In some embodiments, the process comprises that, under suitable reaction conditions for converting p-nitrobenzaldehyde to (2S, 3R)-2-amino-3-hydroxy-3-(4-nitrophenyl) propanoic acid, in the presence of glycine, the p-nitrobenzaldehyde is contacted with the engineered aldolase polypeptides described herein.

Any of the processes for the preparation of a compound of formula (I) or a compound of formula A2 using an engineered polypeptide as disclosed herein can be performed under a range of suitable reaction conditions, which including, but not limited to, amino donor, pH, temperature, buffer, solvent system, substrate loading, polypeptide loading, cofactor loading, pressure and reaction time range. For example, in some embodiments, preparing a compound of formula (I) or a compound of formula A2 may be performed, wherein suitable reaction conditions include: (a) about 10 g/L to 200 g/L of a substrate compound (e.g. compound (II) or A1); (b) about 0.5 g/L to 10 g/L of engineered polypeptide; (c) about 30 g/L to 300 g/L of glycine loading; (d) about 0.1 mM-5 mM PLP cofactor; (e) from 0% (v/v) to about 60% (v/v) of organic solvent, including but not limited to, dimethylsulfoxide (DMSO), Dimethylformamide (DMF), isopropyl acetate, methanol, ethanol, propanol or isopropanol (IPA); (F) a pH of about 4.0 to about 8.0; and (g) a temperature of about 10° C. to about 60° C.

In some embodiments, the process is capable of forming the product (2S, 3R)-2-amino-3-hydroxy-3-(4-nitrophenyl) propanoic acid in a diastereomeric excess of at least 60%.

In some embodiments, the process is capable of forming the product (2S, 3R)-2-amino-3-hydroxy-3-(4-nitrophenyl) propanoic acid in a diastereomeric excess of at least 70%.

In some embodiments, the process is capable of forming the product (2S, 3R)-2-amino-3-hydroxy-3-(4-nitrophenyl) propanoic acid in a diastereomeric excess of at least 80%.

In some embodiments, the process is capable of forming the product (2S, 3R)-2-amino-3-hydroxy-3-(4-nitrophenyl) propanoic acid in a diastereomeric excess of at least 85%.

In some embodiments, the process is capable of forming the product (2S, 3R)-2-amino-3-hydroxy-3-(4-nitrophenyl) propanoic acid in a diastereomeric excess of at least 90%.

In some embodiments, the process is capable of forming the product (2S, 3R)-2-amino-3-hydroxy-3-(4-nitrophenyl) propanoic acid in a diastereomeric excess of at least 95%.

In some embodiments, the process is capable of forming the product (2S, 3R)-2-amino-3-hydroxy-3-(4-nitrophenyl) propanoic acid in a diastereomeric excess of at least 99%.

2. Details

2.1 Definition

Unless expressly defined otherwise, technical and scientific terms used in this disclosure have the meanings that are commonly understood by people skilled in the art.

"Protein", "polypeptide" and "peptide" are used interchangeably herein to denote a polymer of at least two amino acids covalently linked by an amide bond, regardless of length or post-translational modification (e.g., glycosylation, phosphorylation, lipidation, myristoylation, ubiquitination, etc.).

This definition includes D-amino acids and L-amino acids, as well as mixtures of D-amino acids and L-amino acids.

"Engineered aldolase", "engineered aldolase polypeptide", "aldolase polypeptide", "improved aldolase polypeptide", and "engineered polypeptide" are used interchangeably herein.

"Polynucleotide" and "nucleic acid" are used interchangeably herein.

"Cofactor" as used herein refers to a non-protein compound that operates in conjunction with an enzyme in a catalytic reaction. As used herein, "cofactor" is intended to encompass the vitamin B6 family compounds PLP, PN, PL, PM, PNP and PMP, which are sometimes also referred to as coenzymes.

"Pyridoxal phosphate", "PLP", "pyridoxal 5'-phosphate", "PYP" and "P5P" are used interchangeably herein to refer to compounds that act as coenzyme in aldolase reactions.

"Coding sequence" refers to that portion of a nucleic acid (e.g., a gene) that encodes an amino acid sequence of a protein.

"Naturally occurring" or "wild-type" refers to the form found in nature. For example, a naturally-occurring or wild-type polypeptide or polynucleotide sequence is a sequence that is present in an organism that can be isolated from sources in nature and which has not been intentionally modified by manual procedures.

"Recombinant" or "engineered" or "non-naturally occurring" when used with reference to, for example, a cell, nucleic acid or polypeptide, refers to a material or material corresponding to the native or native form of the material, that has been modified in a manner that would not otherwise exist in nature, or is identical thereto but produced or derived from synthetic material and/or by manipulation using recombinant techniques.

"Sequence identity" and "homology" are used interchangeably herein to refer to comparisons between polynucleotide sequences or polypeptide sequences ("sequence identity" and "homology" are generally expressed as a percentage), and are determined by comparing two optimally aligned sequences over a comparison window, where the portion of the polynucleotide or polypeptide sequence in the comparison window may comprise additions or deletions (i.e., gaps) as compared to the reference sequence for optimal alignment of the two sequences. The percentage can be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those skilled in the art will appreciate that there are many established algorithms available to align two sequences. The optimal alignment of sequences for comparison can be conducted, for example, by the local homology algorithm of Smith and Waterman, 1981, Adv. Appl. Math. 2: 482, by the Homology alignment algorithm of Needleman and Wunsch, 1970, J. Mol. Biol. 48: 443, by the search for similarity method of Pearson and Lipman, 1988, Proc. Natl. Acad. Sci. USA 85: 2444, by computerized implementations of these algorithms (GAP, BESTFIT, FASTA, and TFASTA in the GCG Wisconsin Package) or by visual inspection (see generally, Current Protocols in Molecular Biology, FM Ausubel et al. eds., Current Protocols, a Joint Venture between Greene Publishing Associates, Inc. and John Wiley & Sons, Inc., (1995 Supplement) (Ausubel)). Examples of algorithms that are suitable for determining the percent sequence identity and percent sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analysis is publicly available through the National Center for Biotechnology Information website. The algorithm involves first identifying high scoring sequence pairs (HSPs) by identifying short words of length W in the query sequence, which either match or satisfy some positive-valued threshold scores T when aligned with a word of the same length in the database sequence. T is referred to as, the neighborhood word score threshold (Altschul et al., Supra). These initial neighborhood word hits serve as seeds for initiating searches to find longer HSPs that contain them. The word hits are then extended in both directions along each sequence for as far as the cumulative alignment score can be increased. For nucleotide sequences, the cumulative scores are calculated using the parameters M (reward score for matched pair of residues; always>0) and N (penalty score for mismatched residues; always <0). For amino acid sequences, a scoring matrix is used to calculate the cumulative score. The extension of the word hits in each direction are halted when: the cumulative alignment score falls off by the quality X from its maximum achieved value; the cumulative score goes 0 or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, the expected value (E) of 10, M=5, N=−4, and a comparison of both strands as a default value. For amino acid sequences, the BLASTP program uses as defaults the wordlength (W) of 3, the expected value (E) of 10 and the BLOSUM62 scoring matrix (see Henikoff and Henikoff, 1989, Proc Natl Acad Sci USA 89: 10915). Exemplary determination of sequence alignments and % sequence identity can employ the BESTFIT or GAP programs in the GCG Wisconsin Software package (Accelrys, Madison Wis.), using the default parameters provided.

"Reference sequence" refers to a defined sequence that is used as a basis for sequence comparison. The reference sequence may be a subset of a larger sequence, for example, a full-length gene or a fragment of a polypeptide sequence. In general, a reference sequence is at least 20 nucleotides or amino acid residues in length, at least 25 residues long, at least 50 residues in length, or the full length of the nucleic acid or polypeptide. Because two polynucleotides or polypeptides may each (1) comprise a sequence (i.e., a portion of the complete sequence) that is similar between two sequences, and (2) may further comprise sequences that is divergent between the two sequences, sequence comparisons between two (or more) polynucleotides or polypeptides are typically performed by comparing the sequences of the two polynucleotides or polypeptides over a "comparison window" to identify and compare local regions of sequence similarity. In some embodiments, a "reference sequence" is not intended to be limited to a wild-type sequence, and may comprise engineered or altered sequences. For example, "a reference sequence with leucine at the residue corresponding to X39 based on SEQ ID NO: 2" refers to a reference sequence wherein the corresponding residue at position X39 in SEQ ID NO: 2 which is proline, has been altered to leucine.

A "comparison window" refers to a conceptual segment of at least about 20 contiguous nucleotide positions or amino acid residues, wherein the sequence may be compared to a reference sequence of at least 20 contiguous nucleotides or amino acids and wherein the portions of the sequence in the comparison window may comprise additions or deletions (i.e., gaps) of 20% or less as compared to a reference sequence (which does not comprise additions or deletions) for optimal alignment of the two sequences. The comparison window can be longer than 20 contiguous residues, and optionally include 30, 40, 50, 100 or more residues.

In the context of the numbering for a given amino acid or polynucleotide sequence, "corresponding to," "reference to" or "relative to" refers to the numbering of the residues of a specified reference when the given amino acid or polynucleotide sequence is compared to the reference sequence. In other words, the residue number or residue position of a given sequence is designated with respect to the reference sequence, rather than by the actual numerical position of the residue within the given amino acid or polynucleotide sequence. For example, a given amino acid sequence such as an engineered aldolase can be aligned to a reference sequence by introducing gaps to optimize residue matches between the two sequences. In these cases, although there are gaps, the numbering of the residue in a given amino acid or polynucleotide sequence is made with respect to the reference sequence to which they have been aligned.

"Amino acid difference" or "residue difference" refers to the difference in amino acid residues at a position of a polypeptide sequence relative to the amino acid residue at a corresponding position in the reference sequence. The positions of amino acid differences are generally referred to herein as "Xn", where n refers to the corresponding position in the reference sequence on which the residue differences are based. For example, "a residue difference at position X39 as compared to SEQ ID NO: 2" refers to the difference in amino acid residues at the polypeptide position corresponding to position 39 of SEQ ID NO: 2. Thus, if the reference polypeptide of SEQ ID NO: 2 has a proline at position 39, then "a residue difference at position X39 as compared to SEQ ID NO: 2" refers to an amino acid substitution of any residue other than proline at the position of the polypeptide corresponding to position 39 of SEQ ID NO: 2. In most of the examples herein, the specific amino acid residue difference at the position is indicated as "XnY", wherein "Xn" specified to the corresponding position as described above, and "Y" is the single letter identifier of the amino acid found in the engineered polypeptide (i.e., a different residue than in the reference polypeptide). In some examples (e.g., in Table 1), the present disclosure also provides specific amino acid differences denoted by the conventional notation "AnB", where A is a single letter identifier of a residue in the reference sequence, "n" is the number of residue position in the reference sequence, and B is the single letter identifier for the residue substitution in the sequence of the engineered polypeptide. In some examples, an engineered polypeptide of this disclosure may comprise one or more amino acid residue differences relative to a reference sequence, which is indicated by a list of specific positions at which residue differences are present relative to a reference sequence. In some embodiments, more than one amino acid residue can be used in a specific residue position of an engineered polypeptide, the various amino acid residues that can be used are separated by a "/" (e.g., X39L/X39A).

"Deletion" refers to the modification of a polypeptide by removing one or more amino acids from a reference polypeptide. Deletions can include the removal of one or more amino acids, two or more amino acids, five or more amino acids, ten or more amino acids, fifteen or more amino acids, or twenty or more amino acids, up to 10% of the total number of amino acids of the enzyme, or up to 20% of the total number of amino acids making up the reference enzyme while retaining the enzymatic activity of the engineered aldolase and/or retaining the improved properties of the engineered aldolase. Deletion may involve the internal portion and/or the terminal portion of the polypeptide. In various embodiments, deletions may include a contiguous segment or may be discontinuous.

"Insertion" refers to the modification of a polypeptide by adding one or more amino acids from a reference polypeptide. In some embodiments, the improved engineered aldolase comprises insertions of one or more amino acids to a naturally-occurring aldolase polypeptide as well as insertions of one or more amino acids to other engineered aldolase polypeptides. It can be inserted in the internal portions of the polypeptide or inserted to the carboxyl or amino terminus. As used herein, insertions include fusion proteins known in the art. The insertion can be a contiguous segment of amino acids or separated by one or more amino acids in naturally-occurring or engineered polypeptides.

"Fragment" as used herein refers to a polypeptide having an amino terminal and/or carboxyl terminal deletion, but where the remaining amino acid sequence is identical to the corresponding position in the sequence. Fragments may be at least 10 amino acids long, at least 20 amino acids long, at least 50 amino acids long or longer, and up to 70%, 80%, 90%, 95%, 98% and 99% of the full-length aldolase polypeptide.

An "isolated polypeptide" refers to a polypeptide that is substantially separated from other substances with which it is naturally associated, such as proteins, lipids, and polynucleotides. The term comprises polypeptides that have been removed or purified from their naturally occurring environment or expression system (e.g., in host cells or in vitro synthesis). Engineered aldolase polypeptides may be present in the cell, in the cell culture medium, or prepared in various forms, such as lysates or isolated preparations. As such, in some embodiments, the engineered aldolase polypeptide may be an isolated polypeptide.

"Chiral center" refers to a carbon atom connecting four different groups.

"Stereoselectivity" refers to the preferential formation of one stereoisomer over the other in a chemical or enzymatic reaction. Stereoselectivity can be partial, with the formation of one stereoisomer is favored over the other; or it may be complete where only one stereoisomer is formed. When the stereoisomers are enantiomers, the stereoselectivity is referred to as enantioselectivity. It is often reported as "enantiomeric excess" (ee for short). When the stereoisomers are diastereomers, the stereoselectivity is referred to as diastereoselectivity. It is often reported as "diastereomeric excess" (de for short). The fraction, typically a percentage, is generally reported in the art as optionally reported as the diastereomeric excess (i.e., de) derived therefrom according to the following formula: [major diastereomer—minor diastereomer]/[major diastereomer+minor diastereomer]. In some instances, only two diastereomers were detected in the product formed by the engineered aldolase polypeptides of the present disclosure: (2S, 3R)-2-amino-3-hydroxy-3-(4-nitrophenyl) propanoic acid (i.e., A2) and (2S, 3S)-2-amino- 3-hydroxy-3-(4-nitrophenyl) propanoic acid (i.e., A3), the de value for A2 in the product is calculated as follows: [A2−A3]/[A2+A3].

"Stereoisomers," "stereoisomeric forms," and similar expressions are used interchangeably herein to refer to all isomers resulting from a difference in orientation of atoms in their space only. It includes enantiomers and compounds that have more than one chiral center and are not mirror images of one another (i.e., diastereomers).

"Improved enzyme properties" refers to an enzyme property that is better or more desirable for a specific purpose as compared to a reference aldolase such as a wild-type aldolase or another improved engineered aldolase. Improved enzyme properties are exhibited by engineered aldolase polypeptides in this disclosure. Enzyme properties that are expected to be improved include, but are not limited to, enzyme activity (which can be expressed as a percentage of substrate conversion), thermal stability, solvent stability, pH activity characteristics, cofactor requirements, tolerance to inhibitors (e.g., substrate or product inhibition), stereospecificity and stereoselectivity (including enantioselectivity or diastereoselectivity).

"Conversion" refers to the enzymatic transformation of a substrate to the corresponding product. "Percent conversion" or "conversion" refers to the percentage of substrate that is converted to product within a period of time under the specified conditions. Thus, "enzymatic activity" or "activity" of an aldolase polypeptide can be expressed as the "percent conversion" of the substrate to the product.

"Thermostable" means that an aldolase polypeptide that retains similar activity (e.g., greater than 50%) after being exposed to an elevated temperature (e.g., 30-80° C.) for a period of time (0.5-24 h).

"Solvent-stable" refers to an aldolase polypeptide that maintains similar activity (for example more than 50% to 80%) after exposure to varying solvent (ethanol, isopropanol, dimethylsulfoxide (DMSO), tetrahydrofuran, 2-Methyltetrahydrofuran, acetone, toluene, butyl acetate, methyl tert-butyl ether, etc.) for a period of time (e.g., 0.5-24 hours).

"Suitable reaction conditions" refer to those conditions (e.g., enzyme loading, substrate loading, cofactor loading, temperature, pH, buffer, co-solvent, etc.) in the biocatalytic reaction system, under which the aldolase polypeptide of the present disclosure can convert a substrate to a desired product compound. Exemplary "suitable reaction conditions" are provided in the present disclosure and illustrated by examples.

"Hydrocarbyl" refers to a straight or branched hydrocarbon group. The number of subscripts following the symbol "C" specifies the number of carbon atoms that a particular group may contain. For example, "$C_1$-$C_8$" refers to a straight or branched chain hydrocarbyl group having 1 to 8 carbon atoms. Hydrocarbyl groups may optionally be substituted with one or more substituent groups. "Aryl" means a monovalent aromatic hydrocarbon radical of 6 to about 20 carbon atoms. "Heteroaryl" and "heteroaromatic" refer to an aryl group in which one or more of the carbon atoms of the parent aromatic ring system is/are replaced by a heteroatom (O, N, or S). "Substituted", when used to modify a specified group or radical, means that one or more hydrogen atoms of the specified group or radical are each replaced, independently of one another, by identical or different substituents. "Substituted hydrocarbyl, aryl, or heteroaryl" refers to a hydrocarbyl, aryl, or heteroaryl group in which one or more hydrogen atoms are replaced by other substituents. "Optional" or "optionally" means that the described event or circumstance may or may not occur; for example, "optionally substituted aryl" refers to an aryl group that may or may not be substituted. This description includes both substituted aryl groups and unsubstituted aryl groups.

As used herein, "compound" refers to any compound encompassed by the structural formulas and/or chemical names indicated with the compounds disclosed herein. Compounds may be identified by their chemical structure and/or chemical name. When the chemical structure and chemical name conflict, the chemical structure determines the identity of the compound. Unless specifically stated or indicated otherwise, the chemical structures described herein encompass all possible isomeric forms of the described compounds.

2.2 Engineered aldolase

Table 1 below illustrates the engineered aldolase polypeptides developed by the present invention. Each row gives the polynucleotide sequence number and amino acid sequence number of a particular engineered aldolase polypeptide, as well as the residue difference compared to SEQ ID No: 2. The level of activity or stereoselectivity of each exemplified engineered aldolase polypeptide is indicated as "+", with the specific meanings given in Table 2.

TABLE 1

| Poly-nucleotide SEQ ID No | Amino acid SEQ ID No | Residue difference relative to SEQ ID NO:2 | Activity or Stereo-selectivity |
|---|---|---|---|
| 1 | 2 | — | |
| 3 | 4 | N17G; | + |
| 5 | 6 | N17E; | + |
| 7 | 8 | P39L; | + |
| 9 | 10 | G41Y; | + |
| 11 | 12 | D43P; | + |
| 13 | 14 | D43Y; | + |
| 15 | 16 | D16E; E44D; P91H; R132S; S244I; M247Y; G316K; Y318G; H319Y; D320K; | + |
| 17 | 18 | D16E; L45I; P91H; R132S; S244I; M247Y; G316K; Y318G; H319Y; D320K; | + |
| 19 | 20 | D16E; A47H; P91H; R132S; S244I; M247Y; G316K; Y318G; H319Y; D320K; | + |
| 21 | 22 | D16E; G38D; P91H; R132S; G176P; T227P; S244I; M247Y; G285P; G316K; Y318G; H319Y; D320K; | + |
| 23 | 24 | D16E; L45I; P91S; R132S; S244I; M247Y; G316K; Y318G; H319Y; D320K; | ++ |

TABLE 1-continued

| Poly-nucleotide SEQ ID No | Amino acid SEQ ID No | Residue difference relative to SEQ ID NO:2 | Activity or Stereo-selectivity |
|---|---|---|---|
| 25 | 26 | D16E; L45I; P91H; R132S; S244I; M247Y; A305T; G316K; Y318G; H319Y; D320K; | ++ |
| 27 | 28 | D16E; L45I; P91H; R132S; S244I; M247Y; G316S; Y318G; H319Y; D320K; | ++ |
| 29 | 30 | D16E; L45I; P91H; R132S; S244I; M247Y; G316K; Y318G; H319V; D320K; | ++ |
| 31 | 32 | D16E; L45I; Q48L; P91H; R132S; D168N; S244I; M247Y; G316K; Y318G; H319Y; D320K; | ++ |
| 33 | 34 | D16E; L45I; V49S; P91H; R132S; S244I; M247Y; E294K; G316K; Y318G; H319Y; D320K; | ++ |
| 35 | 36 | D16E; L45I; P91H; R132S; K134Q; S244I; M247Y; G316K; Y318G; H319Y; D320K; | ++ |
| 37 | 38 | D16E; A26V; L45I; P91H; R132S; S244I; M247Y; G316K; Y318G; H319Y; D320K; | ++ |
| 39 | 40 | D16E; A26L; L45I; P91H; R132S; E164R; S244I; M247H; L302M; A305P; G316K; Y318G; H319Y; D320K; | ++ |
| 41 | 42 | D16E; A26L; E44D; L45I; P91H; R132S; E164R; S244I; M247H; G316K; Y318G; H319Y; D320K; | ++ |
| 43 | 44 | D16E; T42M; L45I; P91H; R132S; S244I; M247H; L302M; A305P; G316K; Y318G; H319Y; D320E; | ++ |
| 45 | 46 | D16E; E44D; L45I; P91H; R132S; E164R; S244I; M247Y; L302M; G316K; Y318G; H319Y; D320E; | ++ |
| 47 | 48 | D16E; A26L; E44D; L45I; P91H; R132S; E164R; S244I; M247Y; L302M; G316K; Y318G; H319Y; D320K; | ++ |
| 49 | 50 | D16E; A26L; L45I; P91H; R132S; E164R; S244I; M247H; L302M; G316K; Y318G; H319Y; D320E; | ++ |
| 51 | 52 | D16E; A26L; L45I; P91H; R132S; E164R; S244I; M247Y; G316K; Y318G; H319Y; D320K; | ++ |
| 53 | 54 | D16E; A26L; L45I; P91H; R132S; S244I; M247Y; L302M; A305P; G316K; Y318G; H319Y; D320E; | ++ |
| 55 | 56 | D16E; A26L; L45I; P91H; R132S; E164R; S244I; M247H; L302M; G316K; Y318G; H319Y; D320K; | ++ |
| 57 | 58 | D16E; A26L; T42M; E44D; L45I; P91H; R132S; E164R; S244I; M247Y; L302M; G316K; Y318G; H319Y; D320E; | ++ |
| 59 | 60 | D16E; A26L; T42M; E44D; L45I; P91H; R132S; E164R; S244I; M247H; G316K; Y318G; H319Y; D320K; | ++ |
| 61 | 62 | D16E; A26L; T42M; E44D; L45I; P91H; R132S; E164R; S244I; M247Y; L302M; G316K; Y318G; H319Y; D320K; | ++ |
| 63 | 64 | D16E; A26L; E44D; L45I; P91H; R132S; S244I; M247H; L302M; G316K; Y318G; H319Y; D320K; | ++ |
| 65 | 66 | D16E; L45I; P91H; R132S; S244I; M247H; L302M; A305P; G316K; Y318G; H319Y; D320E; | ++ |
| 67 | 68 | D16E; A26L; L45I; P91H; R132S; E164R; S244I; M247Y; L302M; G316K; Y318G; H319Y; D320K; D352Y; | ++ |
| 69 | 70 | D16E; T42M; L45I; P91H; R132S; E164R; S244I; M247H; L302M; G316K; Y318G; H319Y; D320E; | ++ |
| 71 | 72 | D16E; A26L; L45I; T46H; P91H; R132S; S244I; M247H; L302M; A305P; G316K; Y318G; H319Y; D320E; | ++ |
| 73 | 74 | D16E; A26L; E44D; L45I; P91H; R132S; S244I; M247Y; L302M; A305P; G316K; Y318G; H319Y; D320E; | ++ |
| 75 | 76 | D16E; A26L; L45I; P91H; R132S; S244I; M247H; L302M; A305P; G316K; Y318G; H319Y; D320E; | ++ |
| 77 | 78 | D16E; T42M; E44D; L45I; P91H; R132S; E164R; S244I; M247H; L302M; A305P; G316K; Y318G; H319Y; D320K; | ++ |
| 79 | 80 | D16E; E44D; L45I; P91H; R132S; E164R; S244I; M247H; L302M; G316K; Y318G; H319Y; D320E; | ++ |
| 81 | 82 | D16E; A26L; T42M; E44D; L45I; P91H; R132S; E164R; S182A; R237T; S244I; M247Y; L302M; G316K; Y318G; H319Y; D320K; | ++ |
| 83 | 84 | D16E; A26L; E44D; L45I; P91H; R132S; E164R; S244I; M247H; L302M; G316K; Y318L; H319Y; D320E; | ++ |
| 85 | 86 | D16E; G38P; L45I; P91H; R132S; S244I; M247Y; G316K; Y318G; H319Y; D320K; | ++ |
| 87 | 88 | D16E; A26L; T42M; E44D; L45I; P91H; R132S; E164R; S244I; M247H; L302M; A305P; G316K; Y318G; H319Y; D320E; | +++ |
| 89 | 90 | D16E; A26L; T42M; L45I; P91H; R132S; E164R; S244I; M247H; L302M; A305P; G316K; Y318G; H319Y; D320E; | +++ |
| 91 | 92 | D16E; A26L; T42M; L45I; P91L; R132S; S244I; M247H; L302M; A305P; G316K; Y318G; H319Y; D320E; | +++ |
| 93 | 94 | D16E; T42M; L45I; P91K; R132S; S244I; M247H; L302M; A305P; G316K; Y318G; H319Y; D320E; | +++ |
| 95 | 96 | D16E; A19W; T42M; L45I; P91H; R132S; S244I; M247H; L302M; A305P; G316K; Y318G; H319Y; D320E; | +++ |
| 97 | 98 | D16E; A19N; T42M; L45I; P91H; R132S; S244I; M247H; L302M; A305P; G316K; Y318G; H319Y; D320E; | +++ |

TABLE 1-continued

| Poly-nucleotide SEQ ID No | Amino acid SEQ ID No | Residue difference relative to SEQ ID NO:2 | Activity or Stereo-selectivity |
|---|---|---|---|
| 99 | 100 | D16E; H32V; T42M; L45I; P91H; R132S; S244I; M247H; L302M; A305P; G316K; Y318G; H319Y; D320E; | +++ |
| 101 | 102 | D16E; S33N; T42M; L45I; P91H; R132S; S244I; M247H; L302M; A305P; G316K; Y318G; H319Y; D320E; | +++ |
| 103 | 104 | D16E; T42M; L45I; P91H; P118R; R132S; S244I; M247H; L302M; A305P; G316K; Y318G; H319Y; D320E; | +++ |
| 105 | 106 | D16E; T42M; L45I; P91H; R132S; V154G; S244I; M247H; L302M; A305P; G316K; Y318G; H319Y; D320E; | +++ |
| 107 | 108 | D16E; T42M; L45I; P91H; R132S; A218C; S244I; M247H; L302M; A305P; G316K; Y318G; H319Y; D320E; | +++ |
| 109 | 110 | D16E; T42M; L45I; P91H; R132S; L217W; S244I; M247H; L302M; A305P; G316K; Y318G; H319Y; D320E; | +++ |
| 111 | 112 | D16E; T42M; L45I; P91H; R132S; V216C; S244I; M247H; L302M; A305P; G316K; Y318G; H319Y; D320E; | +++ |
| 113 | 114 | D16E; T42M; L45I; P91H; R132S; S244I; M247H; G292K; L302M; A305P; G316K; Y318G; H319Y; D320E; | +++ |
| 115 | 116 | D16E; T42M; L45I; P91H; R132S; S244I; M247H; E294M; L302M; A305P; G316K; Y318G; H319Y; D320E; | +++ |
| 117 | 118 | D16E; T42M; L45I; P91H; R132S; S244I; M247H; G291F; L302M; A305P; G316K; Y318G; H319Y; D320E; | +++ |
| 119 | 120 | D16E; T42M; L45I; P91H; R132S; S244I; M247H; G291V; L302M; A305P; G316K; Y318G; H319Y; D320E; | +++ |
| 121 | 122 | D16E; T42M; L45I; P91H; R132S; L191H; S244I; M247H; L302M; A305P; G316K; Y318G; H319Y; D320E; | +++ |
| 123 | 124 | D16E; G38S; T42M; L45I; P91H; R132S; S244I; M247H; L302M; A305P; G316K; Y318G; H319Y; D320E; | +++ |
| 125 | 126 | D16E; T42M; L45I; P91H; R132S; S244I; M247H; E2881; L302M; A305P; G316K; Y318G; H319Y; D320E; | +++ |
| 127 | 128 | D16E; T42M; L45I; P91H; R132S; S244I; M247H; L302M; A305P; G316K; Y318G; H319Y; D320E; D352Q; | +++ |
| 129 | 130 | D16E; G38E; T42M; L45I; P91H; R132S; S244I; M247H; L302M; A305P; G316K; Y318G; H319Y; D320E; | +++ |
| 131 | 132 | D16E; T42M; L45I; P91H; R132S; S244I; M247H; G285S; L302M; A305P; G316K; Y318G; H319Y; D320E; | +++ |
| 133 | 134 | D16E; T42M; L45I; P91H; R132S; S244I; M247H; G285K; L302M; A305P; G316K; Y318G; H319Y; D320E; | +++ |
| 135 | 136 | D16E; T42M; L45I; P91H; R132S; S244I; M247H; L284K; L302M; A305P; G316K; Y318G; H319Y; D320E; | +++ |
| 137 | 138 | D16E; T42M; L45I; P91H; R132S; S244I; M247H; L284F; L302M; A305P; G316K; Y318G; H319Y; D320E; | +++ |
| 139 | 140 | D16E; T42M; L45I; P91H; R132S; S244I; M247H; E282R; L302M; A305P; G316K; Y318G; H319Y; D320E; | +++ |
| 141 | 142 | D16E; T42M; L45I; P91H; R132S; V189S; S244I; M247H; L302M; A305P; G316K; Y318G; H319Y; D320E; | +++ |
| 143 | 144 | D16E; T42M; L45I; P91H; R132S; S244I; M247H; A295G; L302M; A305P; G316K; Y318G; H319Y; D320E; | +++ |
| 145 | 146 | D16E; T42M; L45I; P91H; R132S; S244I; M247H; L302M; A305P; G316V; Y318G; H319Y; D320E; | +++ |
| 147 | 148 | D16E; T42M; L45I; P91H; R132S; S244I; M247H; L302M; A305P; G316K; Y318G; H319Y; D320E; P324L; | +++ |
| 149 | 150 | D16E; L45I; P91H; R132S; A185T; S244I; M247Y; G316K; Y318G; H319Y; D320K; | +++ |
| 151 | 152 | D16E; A19N; T42M; L45I; P91H; R132S; V154S; S244I; M247H; G291W; L302M; A305P; G316K; Y318G; H319Y; D320E; | ++++ |
| 153 | 154 | D16E; A19N; S33N; T42M; L45I; P91H; R132S; V154S; V216C; L217W; S244I; M247H; L302M; A305P; G316K; Y318G; H319Y; D320E; | ++++ |
| 155 | 156 | D16E; A19N; S33N; T42M; L45I; P91L; R132S; V154A; V216C; L217W; S244I; M247H; L302M; A305P; G316K; Y318G; H319Y; D320E; | ++++ |
| 157 | 158 | D16E; A19N; S33N; T42M; L45I; P91H; R132S; V154S; A218C; S244I; M247H; L302M; A305P; G316K; Y318G; H319Y; D320E; | ++++ |
| 159 | 160 | D16E; A19N; H32V; S33N; T42M; L45I; P91H; R132S; V154S; L217W; A218C; S244I; M247H; L302M; A305P; G316K; Y318G; H319Y; D320E; | ++++ |
| 161 | 162 | D16E; A19N; H32V; S33N; T42M; L45I; P91H; R132S; V154S; V216C; L217W; S244I; M247H; L302M; A305P; G316K; Y318G; H319Y; D320E; | ++++ |
| 163 | 164 | D16E; A19N; A26L; T42M; L45I; P91H; R132S; V216C; S244I; M247H; L302M; A305P; G316K; Y318G; H319Y; D320E; | ++++ |
| 165 | 166 | D16E; A19N; H32V; S33N; T42M; L45I; P91H; R132S; V154A; S244I; M247H; L302M; A305P; G316K; Y318G; H319Y; D320E; | ++++ |
| 167 | 168 | D16E; A19N; A26L; H32V; S33N; T42M; L45I; P91L; R132S; V154S; V216C; L217W; S244I; M247H; L302M; A305P; G316K; Y318G; H319Y; D320E; | ++++ |
| 169 | 170 | D16E; A19N; S33N; G38E; T42M; L45I; P91H; R132S; S244I; M247H; G291W; L302M; A305P; G316K; Y318G; H319Y; D320E; | ++++ |
| 171 | 172 | D16E; A19N; H32V; T42M; L45I; P91H; R132S; S244I; M247H; G291W; L302M; A305P; G316K; Y318G; H319Y; D320E; | ++++ |

TABLE 1-continued

| Poly-nucleotide SEQ ID No | Amino acid SEQ ID No | Residue difference relative to SEQ ID NO:2 | Activity or Stereo-selectivity |
|---|---|---|---|
| 173 | 174 | D16E; A19N; T42M; L45I; P91H; R132S; V154S; V216C; L217W; S244I; M247H; L302M; A305P; G316K; Y318G; H319Y; D320E; | ++++ |
| 175 | 176 | D16E; A19N; H32V; G38A; T42M; L45I; P91H; R132S; S244I; M247H; G291Y; E294M; L302M; A305P; G316K; Y318G; H319Y; D320E; | ++++ |
| 177 | 178 | D16E; A19N; H32V; G38E; T42M; L45I; P91H; R132S; S244I; M247H; L262I; G291Y; E294M; L302M; A305P; G316K; Y318G; H319Y; D320E; | ++++ |
| 179 | 180 | D16E; A19N; S33N; G38S; T42M; L45I; P91H; R132S; S244I; M247H; G291Y; E294M; L302M; A305P; G316K; Y318G; H319Y; D320E; | ++++ |
| 181 | 182 | D16E; A19N; S33N; G38A; T42M; L45I; P91H; R132S; S244I; M247H; E294M; L302M; A305P; G316K; Y318G; H319Y; D320E; | ++++ |
| 183 | 184 | D16E; A19N; H32V; G38S; T42M; L45I; P91H; R132S; S244I; M247H; L262I; G291W; G292V; T293P; E294K; A295Q; L302M; A305P; G316K; Y318G; H319Y; D320E; | ++++ |
| 185 | 186 | D16E; A19N; A37T; G38A; P39A; T42M; L45I; P91H; R132S; S244I; M247H; L302M; A305P; G316K; Y318G; H319Y; D320E; | ++++ |
| 187 | 188 | D16E; A19N; A37M; G38P; P39A; T42M; L45I; P91H; R132S; S244I; M247H; L302M; A305P; G316K; Y318G; H319Y; D320E; | ++++ |
| 189 | 190 | D16E; A19N; A37K; G38A; P39A; T42M; L45I; P91H; R132S; S244I; M247H; L302M; A305P; G316K; Y318G; H319Y; D320E; | ++++ |
| 191 | 192 | D16E; A19N; G38S; T42M; L45I; P91H; R132S; A218S; S244I; M247H; E288T; G291W; L302M; A305P; G316K; Y318G; H319Y; D320E; | +++++ |
| 193 | 194 | D16E; A19N; G38S; T42M; L45I; P91H; R132S; A218C; S244I; M247H; L262I; G291W; G292K; L302M; A305P; G316K; Y318G; H319Y; D320E; | +++++ |
| 195 | 196 | D16E; A19N; T42M; L45I; P91H; R132S; V154F; S244I; M247H; L302M; A305P; G316R; Y318G; H319Y; D320E; D352Q; | +++++ |
| 197 | 198 | D16E; A19N; T42M; L45I; P91H; R132S; V154R; S234R; S244V; M247H; L302M; A305P; G316V; Y318G; H319Y; D320E; D352A; | +++++ |
| 199 | 200 | D16E; A19N; T42M; L45I; P91H; R132S; V154A; S234R; S244V; M247H; L302M; A305P; G316V; Y318G; H319Y; D320E; D352Q; | +++++ |
| 201 | 202 | D16E; A19N; T42M; L45I; P91H; R132S; V154R; S234R; S244I; M247H; L302M; A305P; G316V; Y318G; H319Y; D320E; D352Q; | +++++ |
| 203 | 204 | D16E; A19N; H32V; G38E; T42M; L45I; P91H; R132S; S244I; M247H; L262I; E294M; L302M; A305P; G316K; Y318G; H319Y; D320E; | +++++ |
| 205 | 206 | D16E; A19N; H32V; G38S; P39A; T42M; L45I; P91H; R132S; S244I; M247H; L262I; L302M; A305P; G316K; Y318G; H319Y; D320E; | +++++ |
| 207 | 208 | D16E; A19N; T42M; L45I; P91H; A92W; R132S; S244I; M247H; E282R; L284A; G285K; L302M; A305P; G316K; Y318G; H319Y; D320E; | +++++ |
| 209 | 210 | D16E; A19N; T42M; L45I; P91N; A92W; P118I; R132S; S244I; M247H; E282Y; L284A; G285K; L302M; A305P; G316K; Y318G; H319Y; D320E; | +++++ |
| 211 | 212 | D16E; A19N; T42M; L45I; P91N; P118I; R132S; S244I; M247H; E282K; L284A; G285P; L302M; A305P; G316K; Y318G; H319Y; D320E; | +++++ |
| 213 | 214 | D16E; A19N; T42M; L45I; P91N; P118R; R132S; S244I; M247H; E282Y; L284A; G285P; L302M; A305P; G316K; Y318G; H319Y; D320E; | +++++ |
| 215 | 216 | D16E; A19N; T42M; L45I; P91H; A92W; R132S; S244I; M247H; L284A; G285K; L302M; A305P; G316K; Y318G; H319Y; D320E; | +++++ |
| 217 | 218 | D16E; A19N; T42M; L45I; P91H; R132S; S244I; M247H; E282R; L284A; L302M; A305P; G316K; Y318G; H319Y; D320E; | +++++ |
| 219 | 220 | D16E; A19N; T42M; L45I; P91N; A92W; P118R; R132S; S244I; M247H; E282R; L284A; G285K; L302M; A305P; G316K; Y318G; H319Y; D320E; | +++++ |
| 221 | 222 | D16E; A19N; T42M; L45I; P91N; A92W; R132S; S244I; M247H; E282Y; G285K; L302M; A305P; G316K; Y318G; H319Y; D320E; | +++++ |
| 223 | 224 | D16E; A19N; T42M; L45I; P91H; A92W; R132S; S244I; M247H; E282K; L284A; G285P; L302M; A305P; G316K; Y318G; H319Y; D320E; | +++++ |
| 225 | 226 | D16E; A19N; T42M; L45I; P91H; A92W; P118G; R132S; S244I; M247H; E282Y; L284V; G285P; L302M; A305P; G316K; Y318G; H319Y; D320E; | +++++ |
| 227 | 228 | D16E; A19N; T42M; L45I; P91H; A92W; R132S; S244I; M247H; E282Y; L284A; G285P; L302M; A305P; G316K; Y318G; H319Y; D320E; | +++++ |
| 229 | 230 | D16E; A19N; G38S; T42M; L45I; P91H; R132S; A218S; S244I; M247H; L262I; G291W; G292K; L302M; A305P; G316K; Y318G; H319Y; D320E; | +++++ |

TABLE 2

| Activity or Stereoselectivity | Description | Reaction condition |
|---|---|---|
| + | Conversion of substrate A1 ≥10%, de for A2 in product ≥50%, reaction time ≤8 hours | Loading of enzyme powder 4 g/L, loading of substrate A1 40 g/L, loading of glycine 178 g/L, 50 μM PLP, 25% (v/v) Ethanol, 30° C. |

TABLE 2-continued

| Activity or Stereoselectivity | Description | Reaction condition |
|---|---|---|
| ++ | Conversion of substrate A1 ≥50%, de for A2 in product ≥60%, reaction time ≤8 hours | Loading of enzyme powder 4 g/L, loading of substrate A1 40 g/L, loading of glycine 178 g/L, 50 μM PLP, 40% (v/v) Ethanol, 35° C. |

TABLE 2-continued

| Activity or Stereoselectivity | Description | Reaction condition |
|---|---|---|
| +++ | Conversion of substrate A1 ≥70%, de for A2 in product ≥70%, reaction time ≤8 hours | Loading of enzyme powder 4 g/L, loading of substrate A1 40 g/L, loading of glycine 178 g/L, 50 μM PLP, 40% (v/v) Ethanol, 40° C. |
| ++++ | Conversion of substrate A1 ≥80%, de for A2 in product ≥80%, reaction time ≤8 hours | Loading of enzyme powder 6 g/L, loading of substrate A1 100 g/L, loading of glycine 178 g/L, 50 μM PLP, 40% (v/v) Ethanol, 45° C. |
| +++++ | Conversion of substrate A1 ≥80%, de for A2 in product ≥90%, reaction time ≤8 hours | Loading of enzyme powder 9 g/L, loading of substrate A1 200 g/L, loading of glycine 178 g/L, 50 μM PLP, 40% (v/v) Ethanol, 45° C. |

The amino acid sequences listed in Table 1 (i.e., even sequence identifiers of SEQ ID NO: 2 to 230) each contain 357 amino acid residues. SEQ ID NO: 232, 234, or 236 has a different number of deletion or substitution of amino acid residues as compared to SEQ ID No: 2. The engineered aldolase polypeptides represented by SEQ ID NO: 232, 234, 236 exhibit higher stereoselectivity and/or activity than SEQ ID No: 2 under the reaction conditions of +, ++, +++, ++++ or +++++ as shown in Table 2.

2.3 Polynucleotides, control sequences, expression vectors and host cells that can be used to produce engineered aldolase polypeptides In another aspect, this disclosure provides polynucleotides encoding engineered polypeptides having aldolase activity described herein. The polynucleotides can be linked to one or more heterologous regulatory sequences that control gene expression to produce recombinant polynucleotides that are capable of expressing the engineered polypeptides. Expression constructs comprising a heterologous polynucleotide encoding an engineered aldolase may be introduced into a suitable host cell to express the corresponding engineered aldolase polypeptide.

As apparent to one skilled in the art, the availability of protein sequences and knowledge of codons corresponding to a variety of amino acids provide an illustration of all possible polynucleotides that encode the protein sequence of interest. The degeneracy of the genetic code, in which the same amino acid is encoded by selectable or synonymous codons, allows for the production of an extremely large number of polynucleotides, all of which encode the engineered aldolase polypeptides disclosed herein. Thus, upon determination of a particular amino acid sequence, one skilled in the art can generate any number of different polynucleotides by merely modifying one or more codons in a manner that does not alter the amino acid sequence of the protein. In this regard, this disclosure specifically contemplates each and every possible alteration of a polynucleotide that can be made by selecting a combination based on possible codon selections, for any of the polypeptides disclosed herein, comprising those amino acid sequences of exemplary engineered polypeptides listed in Table 1, and any of the polypeptides disclosed as even sequence identifiers of SEQ ID NOS: 4 to 236 in the Sequence Listing incorporated by reference, all of which are believed to be particularly public.

In various embodiments, the codons are preferably selected to accommodate the host cell in which the recombinant protein is produced. For example, codons preferred for bacteria are used to express genes in bacteria; codons preferred for yeast are used to express genes in yeast; and codons preferred for mammals are used for gene expression in mammalian cells.

In some embodiments, the polynucleotides encode polypeptides comprising amino acid sequences that are at least about 80%, 85%, 86%, 87%, 88%, 89%, 90%, 91%, 92%, 93%, 94%, 95%, 96%, 97%, 98%, 99% or more identical to a reference sequence that is an even sequence identifier of SEQ ID NO: 4-236. Wherein the polypeptides have aldolase activity and one or more of the improved properties described herein, for example, the ability to convert compound A1 to compound A2 with increased stereoselectivity compared to the polypeptide of SEQ ID NO: 2.

In some embodiments, the polynucleotides encode engineered aldolase polypeptides comprising amino acid sequences having a percentage of identity described above and having one or more amino acid residue differences as compared to SEQ ID NO: 2. In some embodiments, the present disclosure provides engineered polypeptides having aldolase activity, wherein the engineered polypeptides comprise a combination that has at least 80% sequence identity to the reference sequence of SEQ ID NO: 2 with residue differences that is selected from the following positions: X16, X17, X19, X26, X32, X33, X37, X38, X39, X41, X42, X43, X44, X45, X46, X47, X48, X49, X91, X92, X118, X132, X134, X154, X164, X168, X176, X182, X185, X189, X191, X216, X217, X218, X227, X234, X237, X244, X247, X262, X282, X284, X285, X288, X291, X292, X293, X294, X295, X302, X305, X316, X318, X319, X320, X324, X352.

In some embodiments, the polynucleotides encoding the engineered aldolase polypeptides comprises sequences having odd sequence identifier of SEQ ID NO: 3-235.

In some embodiments, the polynucleotides encode polypeptides as described herein; but at the nucleotide level, the polynucleotides have about 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity to reference polynucleotides encoding engineered aldolase polypeptides as described herein. In some embodiments, the reference polynucleotides are selected from the sequences having the odd sequence identifiers of SEQ ID NOs: 3-235.

The isolated polynucleotides encoding engineered aldolase polypeptides can be manipulated to enable the expression of the engineered polypeptides in a variety of ways, which comprises further modification of the sequences by codon optimization to improve expression, insertion into suitable expression elements with or without additional control sequences, and transformation into a host cell suitable for expression and production of the engineered polypeptides.

Depending on the expression vector, manipulation of the isolated polynucleotide prior to insertion of the isolated polynucleotide into the vector may be desirable or necessary. Techniques for modifying polynucleotides and nucleic acid sequences using recombinant DNA methods are well known in the art. Guidance is provided below: Sambrook et al., 2001, Molecular Cloning: A Laboratory Manual, Third Edition, Cold Spring Harbor Laboratory Press; and Current Protocols in Molecular Biology, Ausubel. F. Eds., Greene Pub. Associates, 1998, 2010 Year update.

In another aspect, this disclosure also relates to recombinant expression vectors, depending on the type of host they are to be introduced into, including a polynucleotide encoding an engineered aldolase polypeptide or variant thereof, and one or more expression regulatory regions, such as promoters and terminators, origin of replication and the like. Alternatively, the nucleic acid sequence of the present disclosure can be expressed by inserting the nucleic acid sequence or the nucleic acid construct comprising the sequence into an appropriate expression vector. In generating the expression vector, the coding sequence is located in the vector such that the coding sequence is linked to a suitable control sequence for expression.

The recombinant expression vector can be any vector (e.g., a plasmid or virus) that can be conveniently used in recombinant DNA procedures and can result in the expression of a polynucleotide sequence. The choice of vector will generally depend on the compatibility of the vector with the host cell to be introduced into. The vector can be linear or closed circular plasmid. The expression vector may be an autonomously replicating vector, i.e., a vector that exists as an extrachromosomal entity whose replication is independent of chromosomal replication such as plasmids, extrachromosomal elements, minichromosomes, or artificial chromosomes. The vector may contain any tools for ensuring self-copying. Alternatively, the vector may be a vector that, when introduced into a host cell, integrates into the genome and replicates with the chromosome into which it is integrated. Moreover, a single vector or plasmid or two or more vectors or plasmids that together comprise the total DNA to be introduced into the genome of the host cell may be used.

Many expression vectors useful to the embodiments of the present disclosure are commercially available. An exemplary expression vector can be prepared by inserting a polynucleotide encoding an engineered aldolase polypeptide to plasmid pACYC-Duet-1 (Novagen).

In another aspect, this disclosure provides host cells comprising polynucleotides encoding engineered aldolase polypeptides of the present disclosure. The polynucleotide is linked to one or more control sequences for expression of aldolase polypeptides in a host cell. Host cells for expression of polypeptides encoded by the expression vectors of the present disclosure are well known in the art, including, but not limited to, bacterial cells such as *E. coli, Arthrobacter* KNK168, *Streptomyces*, and *Salmonella typhimurium* cells; fungal cells such as yeast cells (e.g., *Saccharomyces cerevisiae* or *Pichia pastoris*); insect cells such as *Drosophila* S2 and *Spodoptera* Sf9 cells; animal cells such as CHO, COS, BHK, 293 and Bowes melanoma cells; and plant cells. An exemplary host cell is *E. coli* BL21 (DE3). The above host cells may be wild-type or may be engineered cells through genomic edition, such as knockout of the wild-type aldolase gene carried in the host cell's genome. Suitable media and growth conditions for the above host cells are well known in the art.

Polynucleotides used to express engineered aldolases can be introduced into cells by a variety of methods known in the art. Techniques comprise, among others, electroporation, bio-particle bombardment, liposome-mediated transfection, calcium chloride transfection, and protoplast fusion. Different methods of introducing polynucleotides into cells are obvious to those skilled in the art.

2.4 Process of producing an engineered aldolase polypeptide

Engineered aldolase can be obtained by subjecting a polynucleotide encoding an aldolase to mutagenesis and/or directed evolution. An exemplary directional evolution technique can be found in "Biocatalysis for the Pharmaceutical Industry: Discovery, Development, and Manufacturing" (2009 John Wiley & Sons Asia (Pte) Ltd. ISBN: 978-0-470-82314-9).

When the sequence of an engineered polypeptide is known, the encoding polynucleotide may be prepared by standard solid-phase methods according to known synthetic methods. In some embodiments, fragments of up to about 100 bases can be synthesized separately and then ligated (e.g., by enzymatic or chemical ligation methods or polymerase-mediated methods) to form any desired contiguous sequence. For example, the polynucleotides and oligonucleotides of the present disclosure can be prepared by chemical synthesis using, for example, the classic phosphoramidite methods described by Beaucage et al., 1981, Tet Lett 22: 1859-69, or Matthes et al. People, 1984, EMBO J. 3: 801-05, as typically practiced in automated synthesis methods. According to the phosphoramidite method, oligonucleotides are synthesized, purified, annealed, ligated, and cloned into a suitable vector, for example, in an automated DNA synthesizer. In addition, essentially any nucleic acid is available from any of a variety of commercial sources.

In some embodiments, the present disclosure also provides a process for preparing or producing an engineered aldolase polypeptide that is capable of converting Compound A1 to Compound A2 under suitable reaction conditions, wherein the process comprises culturing a host cell capable of expressing a polynucleotide encoding an engineered polypeptide under culture conditions suitable for the expression of the polypeptide. In some embodiments, the process of preparing a polypeptide further comprises isolating the polypeptide. Engineered polypeptides may be expressed in suitable cells and isolated (or recovered) from the host cell and/or culture medium using any one or more of the well-known techniques for protein purification, the techniques for protein purification include, among others, lysozyme treatment, sonication, filtration, salting out, ultracentrifugation and chromatography.

2.5 Methods of using an engineered aldolase and compounds prepared therewith

In another aspect, the engineered aldolase polypeptides described herein can asymmetrically condense aldehyde substrates and amino acid substrates. The present disclosure also provides process of preparing a wide range of compounds (I) or structural analogs thereof using an engineered aldolase polypeptide disclosed herein. In some embodiments, engineered aldolase polypeptides can be used in a process of preparing a compound of structural formula (I):

(I)

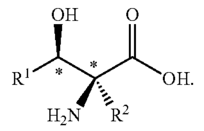

the β-hydroxy-α-amino acid product of formula (I) has the indicated stereochemical configuration at the chiral center marked with an *; the β-hydroxy-α-amino acid product of formula (I) is in diastereomeric excess over the other isomers, where $R^1$ is optionally substituted or unsubstituted aryl or heteroaryl, or optionally substituted or unsubstituted $C_1$-$C_8$ alkyl; $R^2$ is —H, —$CH_2OH$, —$CH_2SH$, —$CH_2SCH_3$, or optionally substituted or unsubstituted $C_1$-$C_4$ hydrocarbyl. The process herein comprises that, under reaction conditions suitable for converting the aldehyde substrate and the amino acid substrate to β-hydroxy-α-amino acid product, the aldehyde substrate of formula (II) and the amino acid substrate of formula (III)

(II)

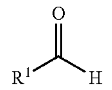

(III)

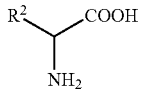

are contacted with an aldolase polypeptide, wherein the aldolase polypeptide is an engineered aldolase polypeptide described herein. In some embodiments, the engineered aldolase polypeptides have at least 80%, 85%, 86%, 87%, 88%, 89%, 90%, 91%, 92%, 93%, 94%, 95%, 96%, 97%, 98%, 99% or more of sequence identity with SEQ ID NO:2, and are capable of condensing the aldehyde substrate of formula (II) and the amino acid substrate of formula (III) to form β-Hydroxy-a-amino acid product of formula (I) with a higher conversion and/or higher stereoselectivity than SEQ ID NO: 2.

In some embodiments, the β-hydroxy-α-amino acid product of formula (I) is present in a diastereomeric excess of at least 60%, 65%, 70%, 75%, 80%, 85%, 90%, 91%, 92%, 93%, 94%, 95%, 96%, 97%, 98%, 99% or greater.

As noted above, aldolase polypeptides useful in the process of the present disclosure may be characterized according to the ability of condensation of p-nitrobenzaldehyde and glycine to (2S, 3R)-2-amino-3-hydroxy-3-(4-nitrophenyl) propanoic acid. Thus, in any of the embodiments of the process disclosed herein, the process may be carried out, wherein the aldolase polypeptides are capable of condensing p-nitrobenzaldehyde and glycine to (2S, 3R)-2-amino-3-hydroxy-3-(4-nitrophenyl) propanoic acid with a higher conversion and/or higher stereoselectivity than SEQ ID NO: 2, and have at least 80%, 85%, 86%, 87%, 88%, 89%, 90%, 91%, 92%, 93%, 94%, 95%, 96%, 97%, 98%, 99% or more of sequence identity with SEQ ID NO:2.

In some embodiments of the above process, $R^1$ is optionally substituted or unsubstituted $C_1$-$C_8$ alkyl. In some embodiments, $R^1$ is optionally substituted or unsubstituted phenyl. In some embodiments, $R^1$ is optionally substituted or unsubstituted pyridyl. In some embodiments, $R^1$ is optionally substituted or unsubstituted aryl or heteroaryl. In some embodiments, $R^1$ is optionally substituted or unsubstituted phenyl, and substitution occurs at either (ortho, meta or para) of the phenyl ring or any two of the substitutions occurring simultaneously on the phenyl ring, the substituents are selected from the group consisting of $C_1$-$C_4$ hydrocarbyl, halogen (e.g., —F, —Cl, —Br and —I), —$NO_2$, —NO, $SO_2R'$ or —SOR', —SR', —NR'R', —OR', —$CO_2R'$ or —COR', —C(O)NR', —$SO_2NH_2$ or —$SONH_2$, —CN, $CF_3$, wherein each R' is independently selected from —H or ($C_1$-$C_4$) alkyl. In some embodiments, ($C_1$-$C_4$) alkyl is a halogen-substituted hydrocarbon.

In some embodiments of the above process, $R^2$ is —H, —$CH_3$, —$CH_2CH_3$, —CH $(CH_3)_2$, —$CH_2OH$, —$CH_2SH$, or —$CH_2SCH_3$.

In some embodiments, the β-hydroxy-α-amino acid product of formula (I) is present in a diastereomeric excess of at least 60%, 65%, 70%, 75%, 80%, 85%, 90%, 91%, 92%, 93%, 94%, 95%, 96%, 97%, 98%, 99% or greater.

In some embodiments of this process, the β-hydroxy-α-amino acid product of formula (I) is (2S, 3R)-(+)-2-amino-3-hydroxy-2,4-methylpentanoic acid:

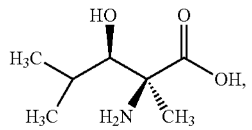

and the amino acid substrate of formula (III) is L-alanine, the aldehyde substrate of formula (II) is isobutyraldehyde:

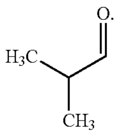

In some embodiments of this process, the β-hydroxy-α-amino acid product of formula (I) is (2S, 3R)-(+)-2-amino-3-hydroxy-4-methylpentanoic acid:

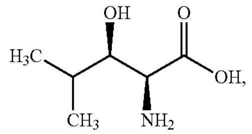

and the amino acid substrate of formula (III) is glycine, the aldehyde substrate of formula (II) is isobutyraldehyde:

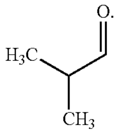

In some embodiments of this process, the β-hydroxy-α-amino acid product of formula (I) is (2S, 3R)-2-amino-3-hydroxydecanoic acid:

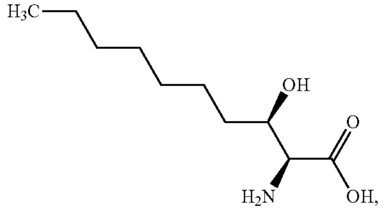

and the amino acid substrate of formula (III) is glycine, the aldehyde substrate of formula (II) is n-octanal:

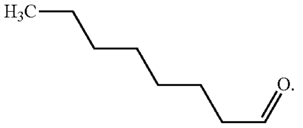

In some embodiments of this process, the β-hydroxy-α-amino acid product of formula (I) is (2S, 3R, 4E)-2-amino-3-hydroxy-4-hexenoic acid:

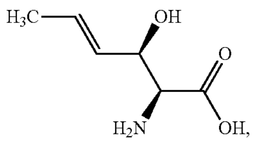

and the amino acid substrate of formula (III) is glycine, the aldehyde substrate of formula (II) is crotonaldehyde:

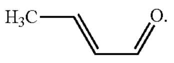

In some embodiments of this process, the β-hydroxy-α-amino acid product of formula (I) is (2S, 3S)-2-amino-3-[(4S) 3-dioxolan-4-yl]-3-hydroxypropanoic acid:

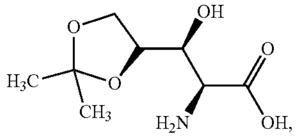

and the amino acid substrate of formula (III) is glycine, the aldehyde substrate of formula (II) is (4S)-2,2-dimethyl-1,3-dioxolane-4-carbaldehyde:

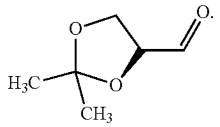

In some embodiments of this process, the β-hydroxy-α-amino acid product of formula (I) is (2S, 3S)-2-amino-3-hydroxy-3-(1H-imidazol-2-yl) propanoic acid:

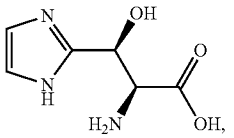 [SMILES: N[C@H](C(=O)O)[C@H](O)c1ncc[nH]1]

and the amino acid substrate of formula (III) is glycine, the aldehyde substrate of formula (II) is 1H-imidazole-2-carboxaldehyde:

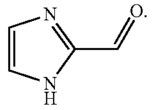

In some embodiments of this process, the β-hydroxy-α-amino acid product of formula (I) is (2S, 3R)-2-amino-3-hydroxy-3-(pyridin-3-yl) propanoic acid:

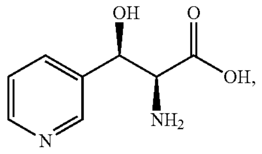 [SMILES: N[C@H](C(=O)O)[C@H](O)c1cccnc1]

and the amino acid substrate of formula (III) is glycine, the aldehyde substrate of formula (II) is pyridine carboxaldehyde:

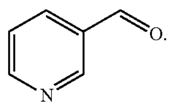

In some embodiments of this process, the β-hydroxy-α-amino acid product of formula (I) is (2S, 3R)-2-amino-3-hydroxy-5-phenylpentanoic acid:

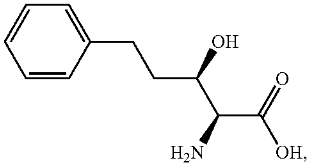 [SMILES: N[C@H](C(=O)O)[C@H](O)CCc1ccccc1]

and the amino acid substrate of formula (III) is glycine, the aldehyde substrate of formula (II) is 3-phenylpropionaldehyde:

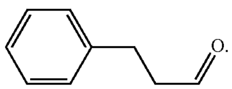

In some embodiments of this process, the β-hydroxy-α-amino acid product of formula (I) is (2S, 3R)-2-amino-5-(benzyloxy)-3-hydroxyvaleric acid:

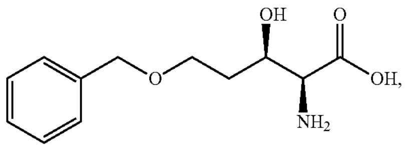 [SMILES: N[C@H](C(=O)O)[C@H](O)CCOCc1ccccc1]

and the amino acid substrate of formula (III) is glycine, the aldehyde substrate of formula (II) is 3-(benzyloxy) propanal:

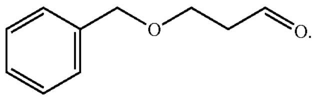 [SMILES: O=CCCOCc1ccccc1]

In some embodiments of this process, the β-hydroxy-α-amino acid product of formula (I) is (2S, 3R)-2-amino-3-(1,3-1,3-benzodioxol-5-yl)-3-hydroxypropanoic acid:

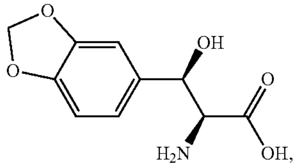 [SMILES: N[C@H](C(=O)O)[C@H](O)c1ccc2c(c1)OCO2]

and the amino acid substrate of formula (III) is glycine, the aldehyde substrate of formula (II) is methylenedioxybenzene-5-carbaldehyde:

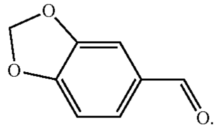 [SMILES: O=Cc1ccc2c(c1)OCO2]

In some embodiments of this process, the β-hydroxy-α-amino acid product of formula (I) is (2S, 3R)-2-amino-4-(2-amino-6-hydroxy-9H-purin-9-Yl)-3-hydroxybutyrate:

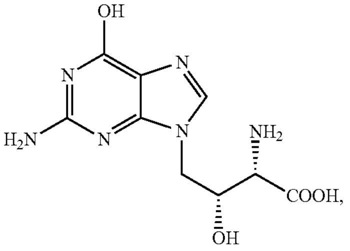 [SMILES: Nc1nc(O)c2ncn(C[C@@H](O)[C@H](N)C(=O)O)c2n1]

and the amino acid substrate of formula (III) is glycine, the aldehyde substrate of formula (II) is (2-amino-6-hydroxy-9H-purin-9-yl) acetaldehyde:

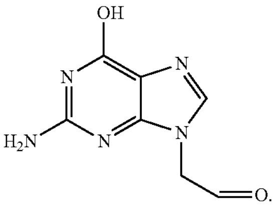 [SMILES: Nc1nc(O)c2ncn(CC=O)c2n1]

In some embodiments, the β-hydroxy-α-amino acid product of Formula (I) produced in the above process is present in a diastereomeric excess of at least 60%, 65%, 70%, 75%, 80%, 85%, 90%, 91%, 92%, 93%, 94%, 95%, 96%, 97%, 98%, 99% or more.

In some embodiments, the β-hydroxy-α-amino acid product of structural formula (I) is:

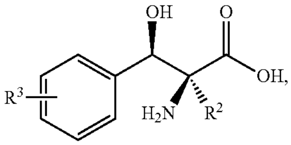

wherein $R^3$ is $C_1$-$C_4$ hydrocarbyl, —H, halogen (such as —F, —Cl, —Br and —I), —$NO_2$, —NO, —$SO_2R'$ or —SOR', —SR', —NR'R', —OR', —$CO_2R'$ or —COR', —C(O)NR', —$SO_2NH_2$ or —$SONH_2$, —CN, $CF_3$, wherein each R' is independently selected from —H or ($C_1$-$C_4$) hydrocarbyl; $R^3$ may also be

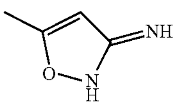

or

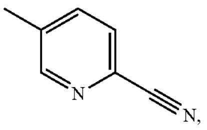

$R^2$ is —H, —$CH_3$, —$CH_2CH_3$, —$CH(CH_3)_2$, —$CH_2OH$, —$CH_2SH$ or —$CH_2SCH_3$, the aldehyde substrate of formula (II) is:

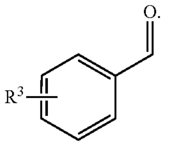

In some embodiments, $R^3$ is in the para position of the phenyl ring. In some embodiments, $R^3$ is in the meta position of the phenyl ring. In some embodiments, $R^3$ is ortho to the phenyl ring. In some embodiments, $R^3$ is both para and meta to the phenyl ring. In some embodiments, $R^3$ is both para and ortho to the phenyl ring. In some embodiments, $R^3$ is both meta and ortho to the phenyl ring. In some embodiments, the β-hydroxy-α-amino acid product of Formula (I) produced in the above process is present in a diastereomeric excess of at least 60%, 65%, 70%, 75%, 80%, 85%, 90%, 91%, 92%, 93%, 94%, 95%, 96%, 97%, 98% or 99% or more.

In some embodiments of this process, the β-hydroxy-α-amino acid product of formula (I) is:

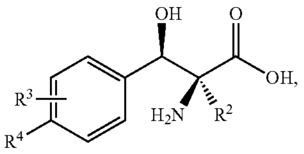

Wherein $R^4$ is $R^3$ as defined above, $R^3$ and $R^2$ are as defined above, the aldehyde substrate of formula (II) is:

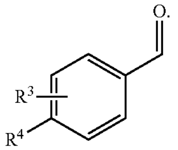

In some embodiments, $R^3$ is in the meta position of the phenyl ring. In some embodiments, $R^3$ is ortho to the phenyl ring. In some embodiments, the β-hydroxy-α-amino acid product of Formula (I) produced in the above process is present in a diastereomeric excess of at least 60%, 65%, 70%, 75%, 80%, 85%, 90%, 91%, 92%, 93%, 94%, 95%, 96%, 97%, 98%, 99% or more.

In some embodiments of this process, the β-hydroxy-α-amino acid product of formula (I) is (2S, 3R)-2-amino-3-hydroxy-3-benzoic acid:

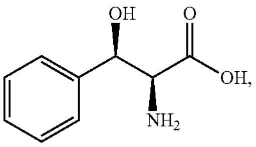 [SMILES: N[C@H](C(=O)O)[C@H](O)c1ccccc1]

and the amino acid substrate of formula (III) is glycine, the aldehyde substrate of formula (II) is benzaldehyde:

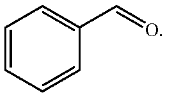

In some embodiments of this process, the β-hydroxy-α-amino acid product of formula (I) is (2S, 3R)-2-amino-3-hydroxy-3-(4-methylphenyl) propanoic acid:

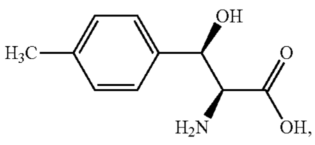

and the amino acid substrate of formula (III) is glycine, the aldehyde substrate of formula (II) is 4-methylbenzaldehyde:

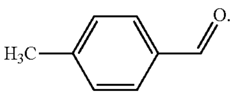

In some embodiments of this process, the β-hydroxy-α-amino acid product of structural formula (I) is (2S, 3R)-2-amino-3-(2-chlorophenyl)-3-hydroxypropanoic acid:

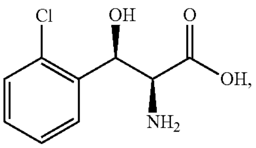 [SMILES: N[C@H](C(=O)O)[C@H](O)c1ccccc1Cl]

and the amino acid substrate of formula (III) is glycine, the aldehyde substrate of formula (II) is 2-chlorobenzaldehyde:

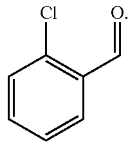

In some embodiments of this process, the β-hydroxy-α-amino acid product of formula (I) is (2S, 3R)-2-amino-3-(3,4-dihydroxybenzene)-3-hydroxypropanoic acid:

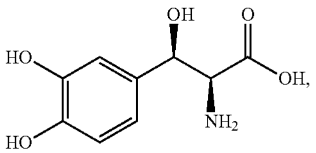

and the amino acid substrate of formula (III) is glycine and the aldehyde substrate of formula (II) is 3,4-dihydroxybenzaldehyde:

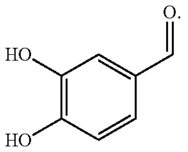

In some embodiments of this process, the β-hydroxy-α-amino acid product of formula (I) is (2S, 3R)-2-amino-3-hydroxy-3-(4-hydroxyphenyl) propanoic acid:

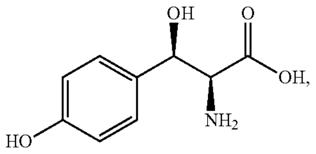

and the amino acid substrate of formula (III) is glycine, the aldehyde substrate of formula (II) is 4-hydroxybenzaldehyde:

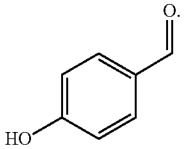

In some embodiments of this process, the β-hydroxy-α-amino acid product of formula (I) is (2S, 3R)-2-amino-3-hydroxy-3-(3-nitrophenyl) propanoic acid:

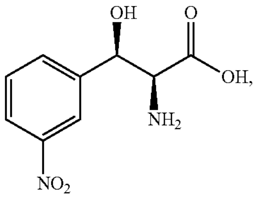 [SMILES: N[C@H](C(=O)O)[C@H](O)c1cccc([N+](=O)[O-])c1]

and the amino acid substrate of formula (III) is glycine, the aldehyde substrate of formula (II) is 3-nitrobenzaldehyde:

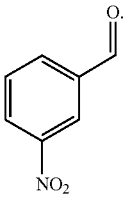

In some embodiments of this process, the β-hydroxy-α-amino acid product of formula (I) is (2S, 3R)-2-amino-3-(4-fluoro-3-nitrophenyl)-3-hydroxypropanoic acid:

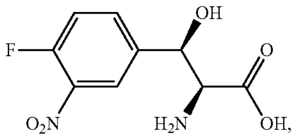

and the amino acid substrate of formula (III) is glycine and the aldehyde substrate of formula (II) is 4-fluoro-3-nitrobenzaldehyde:

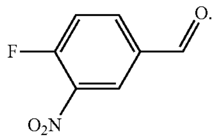 [SMILES: O=Cc1ccc(F)c([N+](=O)[O-])c1]

In some embodiments of this process, the β-hydroxy-α-amino acid product of formula (I) is (2S, 3R)-2-amino-3-hydroxy-2-methyl-3-(3-nitrophenyl) propanoic acid:

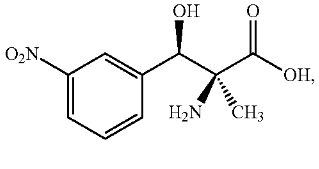 [SMILES: C[C@@](N)(C(=O)O)[C@H](O)c1cccc([N+](=O)[O-])c1]

and the amino acid substrate of formula (III) is L-alanine, the aldehyde substrate of formula (II) is 3-nitrobenzaldehyde:

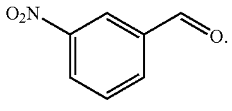 [SMILES: O=Cc1cccc([N+](=O)[O-])c1]

In some embodiments of this process, the β-hydroxy-α-amino acid product of formula (I) is (2S, 3R)-2-amino-3-hydroxy-3-(2-nitrophenyl) propanoic acid:

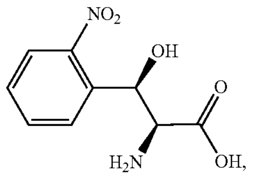 [SMILES: N[C@H](C(=O)O)[C@H](O)c1ccccc1[N+](=O)[O-]]

and the amino acid substrate of formula (III) is glycine, the aldehyde substrate of formula (II) is 2-nitrobenzaldehyde:

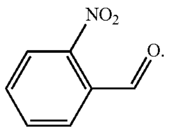 [SMILES: O=Cc1ccccc1[N+](=O)[O-]]

In some embodiments of this process, the β-hydroxy-α-amino acid product of formula (I) is (2S, 3R)-3-[p-(methyl sulfonyl) phenyl]3-hydroxy-2-amino-propanoic acid:

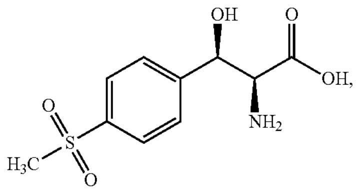 [SMILES: CS(=O)(=O)c1ccc([C@@H](O)[C@H](N)C(=O)O)cc1]

and the amino acid substrate of formula (III) is glycine, the aldehyde substrate of formula (II) is p-methyl sulfone benzaldehyde:

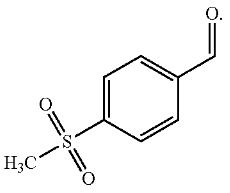

In some embodiments of this process, the β-hydroxy-α-amino acid product of formula (I) is (2S, 3R)-2-amino-3-hydroxy-3-(4-mercaptophenyl) propanoic acid:

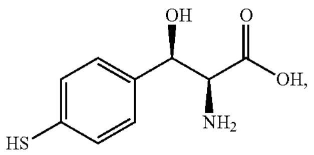 [SMILES: N[C@H](C(=O)O)[C@H](O)c1ccc(S)cc1]

and the amino acid substrate of formula (III) is glycine, the aldehyde substrate of formula (II) is 4-mercaptobenzaldehyde:

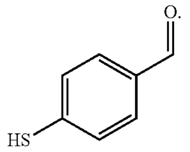

In some embodiments of this process, the β-hydroxy-α-amino acid product of formula (I) is (2S, 3R)-2-amino-3-hydroxy-3-(4-mercaptomethylbenzene) propanoic acid:

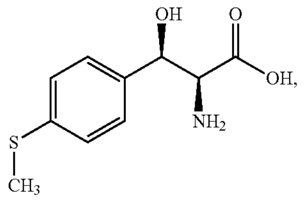

and the amino acid substrate of formula (III) is glycine, the aldehyde substrate of formula (II) is 4-mercaptomethylbenzaldehyde:

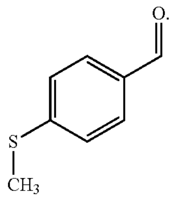

In some embodiments, the β-hydroxy-α-amino acid product of Formula (I) produced in the above process is present in a diastereomeric excess of at least 60%, 65%, 70%, 75%, 80%, 85%, 90%, 91%, 92%, 93%, 94%, 95%, 96%, 97%, 98%, 99% or more.

In some embodiments, the improved engineered aldolase polypeptide can be used in the preparation of a diastereomeric excess of the compound of formula A2 (2S, 3R)-2-amino-3-hydroxy-3-(4-nitrophenyl) propanoic acid:

A2

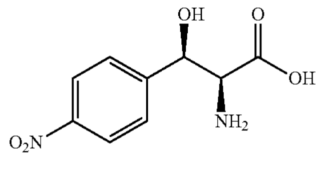

In these embodiments, the process comprises that, in a suitable organic solvent, in the presence of glycine, under reaction conditions suitable for converting the compound of formula A1 to a compound of formula A2, the compound of formula A1 is contacted with the engineered aldolase polypeptides disclosed herein.

A1

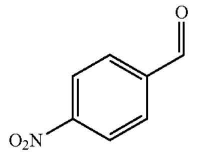

In some embodiments of the above process, the compound of Formula (I) or the compound of Formula A2 is present in a diastereomeric excess of at least 60%, 65%, 70%, 75%, 80%, 85%, 90%, 91%, 92%, 93% 94%, 95%, 96%, 97%, 98%, 99% or greater.

Engineered aldolase polypeptides that can be used in the above process comprise amino acid sequences selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236.

As described herein and exemplified in the examples, the present disclosure contemplates a range of suitable reaction conditions that may be used in the process herein, including but not limited to pH, temperature, buffers, solvent systems, substrate loadings, mixtures of product diastereomers, polypeptide loading, cofactor loading, pressure, and reaction time. Additional suitable reaction conditions for performing a method of biocatalytically converting substrate compounds to a product compound using engineered aldolase polypeptides described herein can be readily optimized by routine experimentation, which including but not limited to that the engineered aldolase polypeptide is contacted with substrate compounds under experimental reaction conditions of varying concentration, pH, temperature, solvent conditions, and the product compound is detected, for example, using the methods described in the Examples provided herein.

As described above, engineered polypeptides having aldolase activity for use in the process of the present disclosure generally comprises amino acid sequences that have at least 80%, 85%, 86%, 87%, 88%, 89%, 90%, 91%, 92%, 93%, 94%, 95%, 96%, 97%, 98% or 99% sequence identity to the reference amino acid sequence selected from any one of the even numbered sequences of SEQ ID NO: 4 to 236.

The substrate compounds in the reaction mixture can be varied, taking into consideration of, for example, the amount of the desired product compound, the effect of the substrate concentration on the enzyme activity, the stability of the enzyme under the reaction conditions, and the percent conversion of substrate to product. In some embodiments of the process, the suitable reaction conditions include at least about 0.5 to about 400 g/L, about 1 to about 400 g/L, about 5 to about 400 g/L, about 10 to about 400 g/L, or about 50 to about 400 g/L of loading of substrate (II) or substrate A1.

In some embodiments, suitable reaction conditions include at least about 0.5 g/L, at least about 1 g/L, at least about 5 g/L, at least about 10 g/L, at least about 15 g/L, at least about 20 g/L, at least about 100 g/L, at least about 150 g/L, at least about 200 g/L, at least about 250 g/L, at least about 300 g/L, at least about 350 g/L, at least about 400 g/L or even more of loading of substrate (II) or substrate A1. The values for the substrate loading provided herein are based on the molecular weight of compound (II) or A1, however it is also contemplated that the equivalent molar amounts of various hydrates and salts of compound (II) or A1 may also be used in the process.

In the process described herein, the engineered aldolase polypeptides use an amino acid and an aldehyde compound to form a product compound. In some embodiments, the amino acids in the reaction conditions include compounds selected from glycine, D,L-alanine, D,L-serine, D,L-cysteine, D,L-leucine, D,L-isoleucine, D,L-methionine, D,L-threonine or D,L-valine. In some embodiments, the amino acid is glycine. In some embodiments, suitable reaction conditions include amino acids present in a loading of at least about 1 times of the molar loading of substrate (II). In some embodiments, glycine is present at a loading of 1, 2, 3, 4, 5, 6, 7, 8, 9 or 10 times of the molar loading of substrate (II).

Suitable reaction conditions for the process generally also include the presence of a cofactor in the reaction mixture. Because the engineered aldolases typically use members of the vitamin B6 family, the reaction conditions may include one or more compounds selected from pyridoxal-5'-phosphate (also known as pyridoxal-phosphate, PLP, P5P), pyridoxine(PN), Pyridoxal(PL), pyridoxamine(PM), and their phosphorylated counterparts; pyridoxine phosphate (PNP), and pyridoxamine phosphate (PMP). In some embodiments, suitable reaction conditions may include a cofactor selected from the group consisting of PLP, PN, PL, PM, PNP and PMP, at a concentration of about 0.1 g/L to about 10 g/L, about 0.2 g/L to about 5 g/L, about 0.5 g/L to about 2.5 g/L. In some embodiments, the cofactor is PLP. Accordingly, in some embodiments, suitable reaction conditions may include cofactor PLP at a concentration of about 0.1 g/L to about 10 g/L, about 0.2 g/L to about 5 g/L, about 0.5 g/L to about 2.5 g/L. In some embodiments, the reaction conditions include about 10 g/L or less, about 5 g/L or less, about 2.5 g/L or less, about 1.0 g/L or less, about 0.5 g/L or Less, or a PLP concentration of about 0.2 g/L or less.

In some embodiments of the process (e.g., where whole cells or lysates are used), the cofactor is present naturally in the cell extract and does not need to be supplemented. In some embodiments of the process (e.g., using partially purified, or purified aldolase), the process may further include the step of adding cofactor to the enzymatic reaction mixture. In some embodiments, cofactor is added either at the beginning of the reaction and/or additional cofactor is added during the reaction.

In the embodiments of the reaction, the reaction conditions may include a suitable pH. As noted above, the desired pH or desired pH range can be maintained by using an acid or base, a suitable buffer, or a combination of buffer and added acid or base. The pH of the reaction mixture can be controlled before and/or during the reaction. In some embodiments, suitable reaction conditions include a solution pH of about 4 to about 8, a pH of about 5 to about 7, a pH of about 6 to about 7. In some embodiments, the reaction conditions include a solution pH of about 4, 4.5, 5, 5.5, 6, 6.5, 7, 7.5 or 8.

In embodiments of the processes herein, suitable temperatures can be used for the reaction conditions, taking into consideration of, for example, the increase in reaction rate at higher temperatures, the activity of the enzyme for sufficient duration of the reaction. Accordingly, in some embodiments, suitable reaction conditions include a temperature of about 10° C. to about 60° C., about 25° C. to about 50° C., about 25° C. to about 40° C., or about 25° C. to about 30° C. In some embodiments, suitable reaction temperatures include a temperature of about 25° C., 30° C., 35° C., 40° C., 45° C., 50° C., 55° C., or 60° C. In some embodiments, the temperature during the enzymatic reaction can be maintained at a certain temperature throughout the reaction. In some embodiments, the temperature during the enzymatic reaction may be adjusted over a temperature profile during the course of the reaction.

The processes of using the engineered aldolases are generally carried out in a solvent. Suitable solvents include water, aqueous buffer solutions, organic solvents, and/or co-solvent systems, which generally include aqueous solvents and organic solvents. The aqueous solutions (water or aqueous co-solvent systems) can be pH-buffered or unbuffered. In some embodiments, the processes of using an engineered aldolase polypeptide are generally carried out in an aqueous co-solvent system comprising an organic solvent (e.g., methanol, ethanol, propanol, isopropanol (IPA), dimethyl sulfoxide (DMSO), dimethylformamide (DMF), isopropyl acetate, ethyl acetate, butyl acetate, 1-octanol, heptane, octane, methyl tert-butyl ether (MTBE), Toluene, etc.), ionic liquids (for example, 1-ethyl 4-methylimidazolium tetrafluoroborate, 1-butyl-3-methylimidazolium tetrafluoroborate, 1-butyl-3-methylimidazolium hexafluorophosphate, and the like). The organic solvent component of the aqueous co-solvent system may be miscible with the aqueous component, providing a single liquid phase, or may be partially miscible or immiscible with the aqueous component, providing two liquid phases. Exemplary aqueous co-solvent system comprises water and one or more organic solvents. In general, the organic solvent component of the aqueous co-solvent system is selected such that it does not completely inactivate the aldolase. Suitable co-solvent system can be readily identified by measuring the enzymatic activity of a particular engineered aldolase with a defined substrate of interest in the candidate solvent system, utilizing enzymatic activity assays, such as those described herein. In some embodiments of the process, suitable reaction conditions include an aqueous co-solvent comprising ethanol at a concentration of about 1% to about 100% (v/v), about 1% to about 60% (v/v), about 2% to about 60% (v/v), about 5% to about 60% (v/v), from about 10% to about 60% (v/v), from about 10% to about 50% (v/v), or about 10% to about 40% (v/v). In some embodiments of the process, suitable reaction conditions include an aqueous co-solvent comprising ethanol at a concentration of at least about 1%, 5%, 10%, 15%, 20%, 25%, 30%, 35%, 40%, 45%, 50%, 55%, or 60% (v/v).

Suitable reaction conditions can include a combination of reaction parameters that provide for the biocatalytic conversion of the substrate compounds to its corresponding product compound. Accordingly, in some embodiments of the process, the combination of reaction parameters comprises: (a) substrate A1 loading of about 10 g/L to about 200 g/L; (b) glycine loading is about 3 to 10 times the molar amount of substrate A1; (C) engineered polypeptide concentration of about 0.5 g/L to 10 g/L; (d) PLP cofactor concentration of about 0.1 mM to 10 mM; (e) DMSO or ethanol concentration of about 20% (v/v) to about 60% (v/v); (f) pH of about 4.0 to 8.0; and (g) temperature of about 10° C. to 60° C.

Exemplary reaction conditions include the assay conditions provided in Table 2 and Example 3.

In carrying out the reaction described herein, the engineered aldolase polypeptide may be added to the reaction mixture in the partially purified or purified forms, whole cells transformed with the gene encoding the engineered aldolase polypeptide, and/or as cell extracts and/or lysates of such cells. Whole cells transformed with the gene encoding the engineered aldolase or cell extracts, lysates thereof, and isolated enzymes can be used in a wide variety of different forms, including solids (e.g., lyophilized, spray dried, or the like) or semisolid (e.g., a crude paste). The cell extract or cell lysate may be partially purified by precipitation (e.g., ammonium sulfate, polyethyleneimine, heat treatment or the like), followed by desalting procedures (e.g., ultrafiltration, dialysis, and the like) prior to lyophilization. Any of the enzyme preparations can be stabilized by crosslinking using known crosslinking agents, such as glutaraldehyde, or immobilization to a solid phase material (such as a resin).

In some embodiments of the reactions described herein, the reaction is performed under suitable reaction conditions described herein, wherein the engineered aldolase polypeptide is immobilized to a solid support. Solid supports useful for immobilizing the engineered aldolase enzyme for carrying out the reaction include but are not limited to beads or resins such as polymethacrylates with epoxy functional groups, polymethacrylates with amino epoxy functional groups, polymethacrylates, styrene/DVB copolymer or polymethacrylates with octadecyl functional groups. Exemplary solid supports include, but are not limited to, chitosan beads, Eupergit C, and SEPABEADs (Mitsubishi), including the following different types of SEPABEAD: EC-EP, EC-HFA/S, EXA252, EXE119 and EXE120.

In some embodiments, wherein an engineered polypeptide is expressed in the form of a secreted polypeptide, a culture medium containing the secreted polypeptide can be used in the process herein.

In some embodiments, the solid reactants (e.g., enzymes, salts, etc.) can be provided to the reaction in a variety of different forms, including powders (e.g., lyophilized, spray dried, etc.), solutions, emulsions, suspensions and the like. The reactants can be readily lyophilized or spray-dried using methods and instrumentation known to one skilled in the art. For example, the protein solution can be frozen at −80° C. in small aliquots, and then added to the pre-chilled lyophilization chamber, followed by the application of a vacuum.

In some embodiments, the order of addition of reactants is not critical. The reactants may be added together to the solvent at the same time (e.g., monophasic solvent, a biphasic aqueous co-solvent system, etc.), or alternatively, some reactants may be added separately, and some may be added together at different time points. For example, the cofactor, aldolase, and substrates may be added first to the solvent. For improved mixing efficiency when using aqueous co-solvent systems, aldolase and cofactors may be added and mixed into the aqueous phase first. The organic phase can then be added and mixed in, followed by addition of the substrates. Alternatively, the substrates can be premixed in the organic phase prior to addition to the aqueous phase.

Different features and embodiments of the present disclosure are exemplified in the following representative examples, which are intended to be illustrative and not restrictive.

3. EXAMPLES

The following examples further illustrate the present invention, but the present invention is not limited thereto. In the following examples, experimental methods with conditions not specified, were conducted at the commonly used conditions or according to the supplier's' suggestion.

Example 1: Gene Cloning and Construction of Expression Vectors

The amino acid sequence of the wild-type aldolase from *Pseudomonas putida* can be retrieved from NCBI, and the corresponding nucleic acids were then synthesized by a vendor using conventional techniques in the art and cloned into the expression vector pACYC-Duet-1. The recombinant expression plasmid was transformed into *E. coli* BL21 (DE3) competent cells under the conditions of 42° C. and thermal shock for 90 seconds. The transformation solution was plated on LB agar plates containing chloramphenicol which was then incubated overnight at 37° C. Recombinant transformants were obtained.

Example 2: Recombinant Expression of Aldolase Polypeptides

The resulting transformant such as recombinant *E. coli* BL21 (DE3) from example 1 was inoculated into LB medium containing chloramphenicol (peptone 10 g/L, yeast extract 5 g/L, NaCl 10 g/L, pH 7.0) which was then cultured in a shaking incubator at 30° C., 250 rpm overnight. The overnight culture was subcultured into a 1 L flask containing 250 mL of TB medium (tryptone 12 g/L, yeast extract 24 g/L, glycerol 4 mL/L, PBS) at 30° C., 250 rpm in a shaking incubator. When the $OD_{600}$ of subculture broth reached 0.6~0.8, IPTG was added to induce the expression of recombinant aldolase at a final concentration of 0.1 mmol/L. After expression overnight, the culture was centrifuged to get resting cells. The pelleted resting cells were suspended in a pH 7.4 buffer, and then sonicated in an ice bath to get cell lysate., The supernatant of cell lysate was collected by centrifugation as a crude enzyme solution of the recombinant aldolase, and the supernatant was further freeze-dried using a lyophilizer to obtain crude enzyme powder.

According to the recombinant expression process using shaking flasks as mentioned above, a miniaturized expression process in 96-well plate was performed by proportionally reducing the scale. The crude enzyme solution was obtained through chemical lysis rather than ultrasonication.

Example 3: Reaction Conditions and Analytical Methods for Measuring Activity and Stereoselectivity of Aldolase Polypeptides p-nitrobenzaldehyde was added at a final concentration of 7.5 g/L in a 96-well plate, where p-nitrobenzaldehyde was dissolved in ethanol (EtOH) prior to its addition. The final concentration of ethanol in the system was 40% (v/v), while glycine was added at 10 times the molar amount of p-nitrobenzaldehyde (i.e., 37.4/L), and pyridoxal phosphate (PLP) was added at the final concentration of 0.05 mmol/L, and finally the crude enzyme solution was added. The total volume of the reaction was 200 μl. After the reaction was run for 4 hours, the reaction was quenched with 50% acetonitrile to inactivate aldolase polypeptides. The quenched reaction was centrifuged and resulting supernatant was diluted and then subjected to HPLC analysis to determine the substrate conversion and the de value for product A2.

Enzymatic reaction was scaled up to 5 mL of total reaction volume on the basis of the above 96-well microplate reaction. The loading of p-nitrobenzaldehyde was 40 g/L, the loading of glycine was 199.2 g/L, the final concentration of PLP was 0.05 mmol/L, concentration of ethanol in the system was 30% (v/v) and crude enzyme powder loading was 4 g/L.

The analytical method for the determination of the conversion and the de value of the product was as follows: the reaction solution was centrifuged and the supernatant was diluted with 50% acetonitrile to a product concentration of less than 1 g/L. 10 μl of this diluted sample was injected into an Agilent 1260 HPLC to analyze the conversion. The column was Phenomenex Chirex 3126 (D)-penicillamine 150*4.6 mm, mobile phase was 3 mM copper sulfate: methanol=90: 10, at a flow rate of 1 mL per minute, at a column temperature of 50° C., and the detection wavelength was 235 nm. The retention time of (2S, 3R)-2-amino-3-hydroxy-3-(4-nitrophenyl) propanoic acid was 22.53 min; the retention time of (2R, 3R)-2-amino-3-hydroxy-3-(4-nitrophenyl) propanoic acid was 24.17 minutes; the retention time of p-nitrobenzaldehyde was 28.65 minutes; the retention time of (2S, 3S)-2-amino-3-hydroxy-3-(4-nitrophenyl) propanoic acid and (2R, 3S)-2-amino-3-hydroxy-3-(4-nitrophenyl) propanoic acid was 64.19 minutes. The total analysis time was 70 minutes.

Example 4: Construction of Aldolase Mutant Library

Quikchange kit (supplier: Agilent) was preferably used here. The sequence design of the mutagenesis primers was performed according to the instructions of the kit. The PCR system consisted of 10 μl of 5× Buffer, 1 μl of 10 mM dNTP, 1 μl of plasmid DNA template (50 ng/μl), 0.75 μl (10 uM) each of the upstream and downstream primers, 0.5 μl of high fidelity enzyme and 36 μl of ddH2O, The PCR primer has a NNK codon at the mutation position.

PCR amplification steps: (1) 98° C. pre-denaturation 3 min; (2) 98° C. denaturation 10s; (3) annealing and extension 3 min at 72° C.; steps of (2)~(3) repeated 25 times; (5) extension 10 min at 72° C.; (6) cooling to 4° C., 2 μl of DpnI was added to the PCR product and the plasmid template was eliminated by overnight digestion at 37° C. The digested PCR product was transformed into *E. coli* BL21 (DE3) competent cells and plated on LB agar plates containing chloramphenicol to obtain a site-saturation mutagenesis library.

Example 5: High-Throughput Screening of Aldolase Mutant Libraries

Mutant colonies were picked from the LB agar plates, inoculated into 200 μl of LB medium (containing chloramphenicol) in a 96-well shallow plate and cultured overnight at 30° C. 20 μl of the above culture was used to inoculate 400 μl of TB medium (including chloramphenicol) in a deep-well plate. When $OD_{600}$ of deep-well culture reached 0.6~0.8, and IPTG was added to induce expression at a final concentration of 1 mM, and the expression undertook at 30° C. overnight. Once the overnight expression was done, the culture was centrifuged at 4000 rpm for 10 minutes to obtain cell pellets to which 200 μl of a chemical lysis reagent (1 g/L lysozyme, 0.5 g/L PMBS) was added to break the cells. Then cell lysate was centrifuged at 4000 rpm for 10 minutes, and subsequently 60 μl of supernatant per well were transferred into a deep well plate containing the reaction solution described in Example 3. The reaction was shaken at 30~50° C. for desired time, and finally quenched with 50% acetonitrile. Samples were taken for analysis.

Example 6: Fermentation Process for the Expression of Engineered Aldolase

A single microbial colony of *E. coli* containing a plasmid bearing the target aldolase gene was inoculated into a 50 mL LB broth containing 30 μg/mL chloramphenicol (5.0 g/L Yeast Extract, 10 g/L Tryptone, 10 g/L sodium chloride). Cells were incubated overnight (at least 16 hours) with shaking at 250 rpm in a 30° C. shaker. When the OD600 of the culture reached 1.6 to 2.2, the culture was used to inoculate medium in fermentor.

A 5 L fermentor containing 2.0 L of growth medium was sterilized in a 121° C. autoclave for 30 minutes. The fermentor was inoculated with the abovementioned culture. Temperature of fermentor was maintained at 37° C. The growth medium in fermentor was agitated at 200-800 rpm and air was supplied to the fermentation vessel at 2-8 L/min to maintain the dissolved oxygen level at 30% saturation or greater. The culture was maintained at pH 7.0 by addition of 25-28% v/v ammonium hydroxide. Cell growth was maintained by feeding a feed solution containing 500 g/L of dextrose glucose monohydrate, 12 g/L ammonium chloride, and 5 g/L magnesium sulfate heptahydrate. After the $OD_{600}$ of culture reached 25±5, the temperature of fermentor was decreased and maintained at 30° C., and the expression of aldolase polypeptides was induced by the addition of isopropyl-β-D-thiogalactopyranoside (IPTG) to a final concentration of 1 mM. Fermentation process then continued for additional 18 hours. After the fermentation process was complete, cells were harvested using a Thermo Multifuge X3R centrifuge at 8000 rpm for 10 minutes at 4° C. Harvested cells were used directly in the downstream recovery process or stored frozen at −20° C.

6 g of cell pellet was resuspended in 30 mL of 100 mM potassium phosphate buffer containing 250 μM pyridoxal 5'-phosphate (PLP), pH 7.5 at 4° C. The cells were then homogenized into cell lysate using a homogenizer. The cell lysate was clarified using a Thermo Multifuge X3R centrifuge at 8000 rpm for 10 minutes at 4° C. The clarified supernatant was dispensed into a shallow container, frozen at −20° C. and lyophilized to a enzyme powder. The aldolase enzyme powder was stored frozen at −20° C.

Example 7: Asymmetric Synthesis of (2s, 3r)-2-amino-3-hydroxy-3-(4-nitrophenyl) Propanoic Acid from Aldehydes and Amino Acids Catalyzed by Aldolase Polypeptides Taking a total volume of 1.0 L as an example, the following items were added to the reaction vessel: 178 g of glycine, 30 g of p-nitrobenzaldehyde, 942 mL of a 25% (v/v) aqueous ethanol solution, 4 g of enzyme powder of SEQ ID NO: 6, 5 mL of PLP stock solution (10 mM). The reaction temperature was set at 30° C. and the stirring speed was 400 rpm. After 8 hours of reaction, the total conversion of the substrate was ≥20% and de ≥95% for the product A2. Supernatant was obtained by filtration of the reaction, and the supernatant was concentrated to precipitate a solid crude product. The crude solid was washed with 300 mL of pure water for 30 minutes by stirring at 25° C. Filtration was applied, and the filter cake was vacuum dried to obtain pure product (2S, 3R)-2-amino-3-hydroxy-3-(4-nitrophenyl) propanoic acid (chemical purity 99.5%, de ≥99%).

Example 8: Preparation of D-(−)-threo-2-amino-1-(4-nitrophenyl)-1,3-propanediol From (2S, 3R)-2-amino-3-hydroxy-3-(4-nitrophenyl) Propanoic Acid 1000 mL of anhydrous methanol was added to a reaction vessel with ice bath, and it was stirred for 1 hour. The temperature of the reaction vessel was maintained at 5° C., and within 1 hour, 128 mL of thionyl chloride was slowly added dropwise into the reaction vessel. After the addition of thionyl chloride was completed, the reaction mixture was stirred in an ice bath for 1 hour. Then 100 g of (2S, 3R)-2-amino-3-hydroxy-3-(4-nitrophenyl) propanoic acid was added into the reaction, followed by raising reaction temperature to 25° C. and stirring for 3 hours. Then the reaction temperature was slowly raised to 65° C. (reflux). Reflux reaction was carried out for about 24 hours. After etherification was complete, $SO_2$, HCl, and methanol were removed by depressurization at 40° C. until no liquid flew out. Then 1000 mL ice water were added to cool down the reaction. At the same time, KOH solution was added dropwise to adjust the pH of reaction to about 8.0, and the reaction was stirred for 1 hour. Finally, the reaction was filtered, and the filtered cake was washed with water. 80 g of a white solid substance was obtained after drying the filter cake which was the ester product.

In order to obtain D-(−)-threo-2-amino-1-(4-nitrophenyl)-1,3-propanediol by reducing the ester product, 1200 mL THF, 75 g ester product were added into a reaction vessel, and it was stirred for 30 min. Then 12 g NaBH4 slowly added into the reaction which was stirred for 1 hour and then heated to reflux (50-55° C.). Subsequently, 160 mL methanol were slowly added dropwise into the reaction within 30 min, followed by stirring for 3 hours to finish the reaction. Concentrated hydrochloric acid were used to adjust the pH of finished reaction to ≤2, and it was stirred overnight. The reaction was filtered, and THF and methanol were removed from the filtrate under reduced pressure. 500 mL of pure water were then added to the filtrate, and KOH were added to adjust pH ≥10. The filtrate was kept at 4° C. for crystallization to occur. The crystallized substance was recovered by filtration, and filter cake was dried to get about 55 g D-(−)-threo-2-amino-1-(4-nitrophenyl)-1,3-propanediol.

Example 9 Asymmetric Synthesis of (2S, 3R)-3-[p-(Methyl sulfonyl) phenyl]-3-hydroxy-2-amino-propanoic Acid Catalyzed by Aldolase Polypeptides

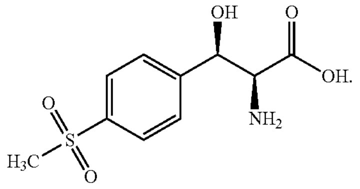 [SMILES: CS(=O)(=O)c1ccc([C@@H](O)[C@H](N)C(=O)O)cc1]

Taking a total volume of 1.0 L as an example, the following items were added to the reaction vessel: 178 g of glycine, 40 g of p-methylsulfonylbenzaldehyde, 958 mL of a 40% (v/v) aqueous ethanol solution, 4 g of the enzyme powder of SEQ ID NO: 18, 5 mL of PLP stock solution (10 mM). The reaction temperature was set at 30° C. and the stirring speed was 400 rpm. After 6 hours of reaction, the conversion of p-methylsulfonylbenzaldehyde was ≥40%. The de for product (2S, 3R)-3-[p-(methylsulfonyl) phenyl]-hydroxy-2-amino-propanoic acid was ≥90%.

Example 10 Asymmetric Synthesis of (2S, 3R)-2-amino-3-(3,4-dihydroxybenzene)-3-hydroxypropanoic Acid Catalyzed by Aldolase Polypeptides

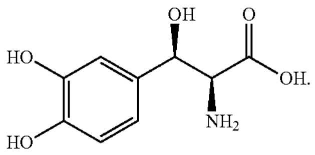 [SMILES: N[C@H](C(=O)O)[C@H](O)c1ccc(O)c(O)c1]

Taking a total reaction volume of 1.0 L for example, the following items were added to the reaction vessel: 55 g of glycine, 10 g of 3,4-dihydroxybenzaldehyde, 960 mL of deionized water, 10 g of enzyme powder of SEQ ID NO: 44, 5 mL of PLP stock solution (10 mM). The reaction temperature was set at 30° C., stirring speed was 400 rpm. After 2 hours of reaction, the total conversion of the substrate 3,4-dihydroxybenzaldehyde was ≥40%.

It should be understood that after reading the above contents of the present invention, those skilled in the art may make various modifications or changes to the present invention. And these equivalent forms also fall within the scope of the appended claims of the present invention.

The invention claimed is:

1. An engineered aldolase polypeptide that condenses p-nitrobenzaldehyde with glycine to produce (2S, 3R)-2-amino-3-hydroxy-3-(4-nitrophenyl) propanoic acid, said engineered aldolase polypeptide comprising an amino acid sequence having at least one amino acid substitution relative to SEQ ID NO:2, said at least one substitution selected from the group consisting of L45I, P91H, and combinations thereof, further wherein said amino acid sequence is selected from the group consisting of SEQ ID NOs: 16, 18, 20,22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, and 230.

2. The aldolase polypeptide of claim 1, wherein said engineered aldolase polypeptide condenses p-nitrobenzaldehyde with glycine to produce (2S, 3R)-2- amino-3-hydroxy-3-(4-nitrophenyl) propanoic acid in a diastereomeric excess of at least 60% under suitable reaction conditions include about 40 g/L p-nitrobenzaldehyde, about 178 g/L glycine, about 50 μm pyridoxal 5'-phosphate (PLP), and about 25% (v/v) ethanol, at about 30° C.

3. An engineered polypeptide, which is a polypeptide having aldolase activity, which comprises an amino acid sequence having at least 85% sequence identity to one of the amino acid sequences set forth in of SEQ ID NOs: 16, 18, 20,22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, or 230 and having L45I and/or P91 H amino acid substitution.

4. A polypeptide immobilized on a solid material by a chemical bond or a physical adsorption method, wherein the polypeptide comprises the engineered aldolase polypeptide according to claim 1.

5. An aldolase catalyst obtained by culturing host cells comprising an expression vector comprising a polynucleotide encoding the engineered aldolase polypeptide of claim 1, wherein said aldolase catalyst comprises cells or culture fluid containing the aldolase polypeptides, or an article processed therewith, further wherein the article refers to an extract obtained from the culture of transformant cell, an isolated product obtained by isolating or purifying an aldolase from the extract, or an immobilized product obtained by immobilizing transformant cell, an extract thereof, or isolated product of the extract.

6. A process of preparing a β-hydroxy-α-amino acid of formula (I):

(I)

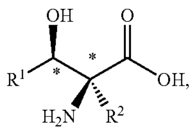

wherein the β-hydroxy-α-amino acid of formula (I) has the indicated stereochemical configuration at the chiral center marked with an *;

further wherein:

$R^1$ is selected from among optionally substituted or unsubstituted aryl or heteroaryl and optionally substituted or unsubstituted $C_1$-$C_8$ hydrocarbyl;

$R^2$ is selected from among —H, —$CH_2OH$,—$CH_2SH$,—$CH_2SCH_3$, and optionally substituted or unsubstituted $C_1$-$C_4$ hydrocarbyl;

wherein the process comprises the steps of:

(a) contacting an aldehyde substrate of formula (II) and an amino acid substrate of formula (III)

(II)

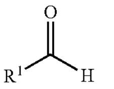

(III)

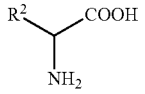

with the engineered polypeptide of claim 1, under suitable reaction conditions; and (b) converting the aldehyde substrate and the amino acid substrate to produce the β-hydroxy-α-amino acid, further wherein the β-hydroxy-α-amino acid of formula (I) is obtained in diastereomeric excess.

7. The process of claim 6, wherein the β-hydroxy-α-amino acid of formula (I) is:

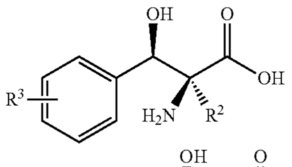

or

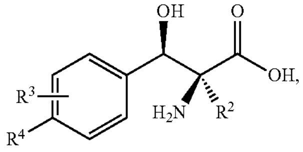

further wherein $R^2$ is —H, —$CH_3$, —$CH_2CH_3$, —$CH(CH_3)_2$, —$CH_2OH$,—$CH_2SH$ or —$CH_2SCH_3$;

$R^3$ is a $C_1$-$C_4$ hydrocarbyl, —H, a halogen selected from among —F, —Cl, —Br and —I, —$NO_2$, —NO, —$SO_2R'$, —SOR', —SR', —NR'R', —OR', —$CO_2R'$, —COR', —C(O)NR', —$SO_2NH_2$, —$SONH_2$, —CN, or —$CF_3$, wherein each R' is independently selected from —H or ($C_1$-$C_4$) hydrocarbyl;

$R^3$ can also be

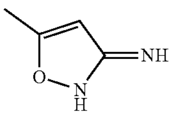

or

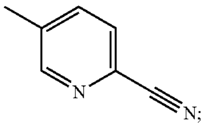

$R^4$ is a $C_1$-$C_4$ hydrocarbyl, —H, a halogen selected from among —F, —Cl, —Br and —I, —$NO_2$, —NO, —$SO_2R$, —SOR, —SR', —NR'R'-OR', —$CO_2R'$, —COR', —C(O)NR', —$SO_2NH_2$, —$SONH_2$, —CN, or —$CF_3$, wherein each R' is independently selected From —H or ($C_1$-$C_4$) hydrocarbyl; and the aldehyde substrate of formula (II) is:

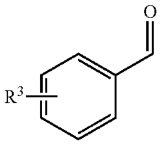

or

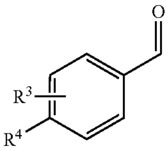

.

8. The process of claim 7, wherein $R^3$ is:

in the para position of the phenyl ring;

in the meta position of the phenyl ring;

in the ortho position of the phenyl ring;

in both the para position and the meta position of the phenyl ring;

in both the para position and the ortho position of the phenyl ring; or in both the meta position and the ortho position of the phenyl ring.

9. The process of claim 6, wherein the β-hydroxy-α-amino acid of formula (I) is selected from among:

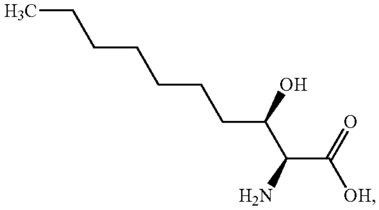

,

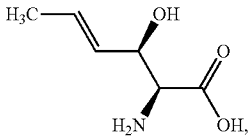

,

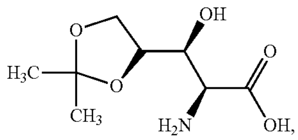

,

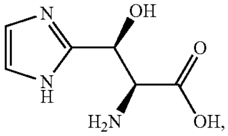

,

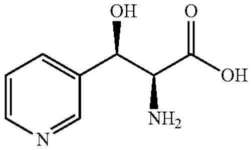

,

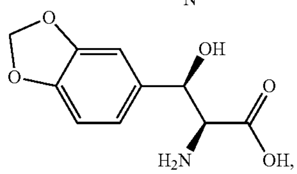

,

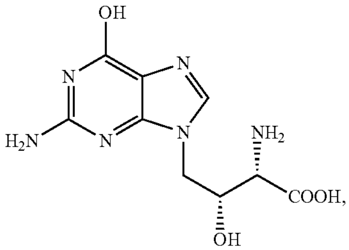

,

-continued

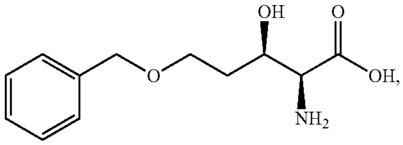

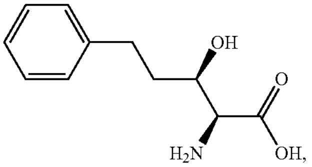

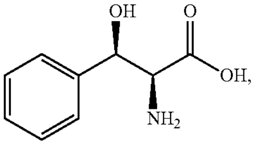

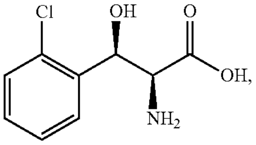

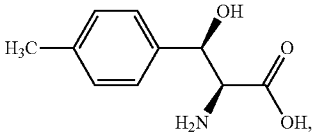

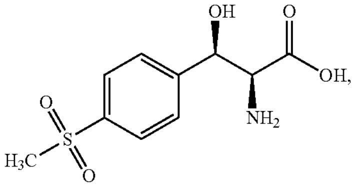

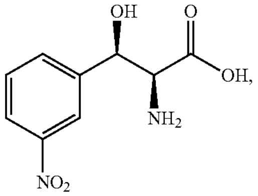

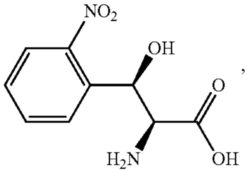

,

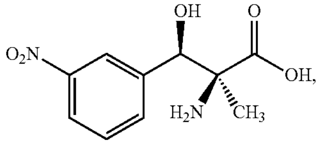

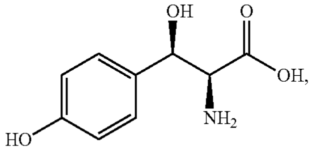

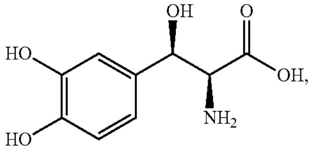

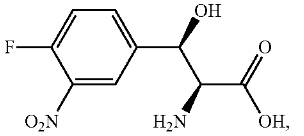

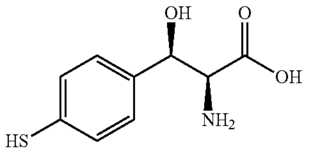

or

-continued

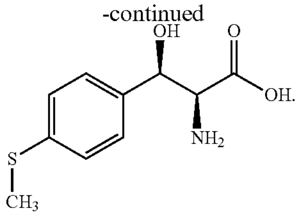

10. A process for preparing a compound of formula A2 (2S, 3R)-2-amino-3-hydroxy-3-(4-nitrophenyl) propionic acid:

A2

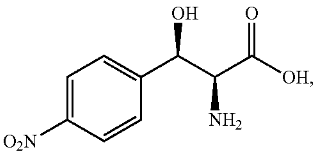

wherein the process comprises the steps of:

(a) contacting p-nitrobenzaldehyde of formula A1

A1

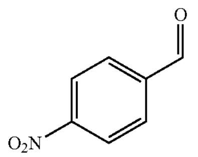

with an engineered aldolase polypeptide of claim 1 in the presence of glycine, in a suitable -solvent, under suitable reaction conditions; and (b) converting the compound of formula A1 to the compound of formula A2.

11. The process of claim 6, wherein the β-hydroxy-α-amino acid product is present in diastereomeric excess of at least 60%.

12. The process of claim 6, wherein the reaction is carried out in a solvent comprising water, methanol, ethanol, propanol, isopropanol, isopropyl acetate, dimethylsulfoxide (DMSO) or dimethylformamide (DMF).

13. The process of claim 6, wherein the reaction conditions include a temperature of 10° C. to 60° C.

14. The process of claim 6, wherein the reaction conditions include pH 4.0 to pH 8.0.

15. The process of claim 6, wherein the aldehyde substrate is present at a loading of 5 g/L to 400 g/L.

16. The engineered aldolase polypeptide of claim 1, wherein said (2S, 3R)-2-amino-3-hydroxy-3-(4-nitrophenyl) propanoic acid is produced in a diastereomeric excess of at least 80%.

17. The engineered aldolase polypeptide of claim 1, wherein said (2S, 3R)-2-amino-3-hydroxy-3-(4-nitrophenyl) propanoic acid is produced in a diastereomeric excess of 95% or more.

18. An aldolase catalyst obtained by culturing host cells comprising an expression vector comprising a polynucleotide encoding the engineered aldolase polypeptide of claim 3, wherein said aldolase catalyst comprises cells or culture fluid containing the aldolase polypeptides, or an article processed therewith, further wherein the article refers to an extract obtained from the culture of transformant cell, an isolated product obtained by isolating or purifying an aldolase from the extract, or an immobilized product obtained by immobilizing transformant cell, an extract thereof, or isolated product of the extract.

19. The aldolase polypeptide of claim 1, wherein said engineered aldolase polypeptide comprises the amino acid sequence set forth in SEQ ID NO: 18.

* * * * *

SEQUENCE LISTING

<160> NUMBER OF SEQ ID NOS: 236

<210> SEQ ID NO 1
<211> LENGTH: 1071
<212> TYPE: DNA
<213> ORGANISM: Artificial Sequence
<220> FEATURE:
<223> OTHER INFORMATION: Engineered sequence

<400> SEQUENCE: 1
atgaacggtg aaacctcgcg tccgccggcg ctgggtttta gctctgataa tattgctggt 60
gcaagcccgg aagtcgcaca ggcactggtg aaacatagtt ccggccaagc gggtccgtat 120

-continued

```
ggcaccgatg aactgacggc ccaggtgaaa cgtaaatttt gcgaaatctt cgaacgcgac    180

gtcgaagtgt tcctggttcc gaccggtacg gcagcaaacg cactgtgtct gtccgcaatg    240

accccgccgt ggggtaatat ttactgccat ccggcgtccc acatcaacaa tgatgaatgt    300

ggtgcgccgg aatttttctc aaacggcgcc aaactgatga ccgttgatgg tccggcagct    360

aaactggaca ttgtccgtct gcgcgaacgt acgcgcgaaa aagtgggtga tgttcatacc    420

acgcagccgg catgcgtctc tattacccaa gctacggaag tgggcagtat ctataccctg    480

gatgaaattg aagccatcgg tgacgtgtgc aaatcatcga gcctgggtct gcacatggat    540

ggctctcgtt ttgctaatgc gctggtgtcc ctgggctgtt caccggcaga aatgacctgg    600

aaagccggtg ttgacgcact gagttttggt gcgacgaaaa acggcgttct ggcggccgaa    660

gcaattgtcc tgttcaatac ctcgctggct acggaaatga gctatcgtcg caaacgtgcc    720

ggccacctgt ctagtaaaat gcgctttctg agcgctcaga tcgatgcgta cctgaccgat    780

gacctgtggc tgcgtaacgc ccgcaaagca aatgcagctg cgcagcgtct ggcccaaggt    840

ctggaaggcc tgggcggtgt tgaagtcctg ggcggtaccg aagcaaacat tctgttctgt    900

cgcctggatt ctgccatgat cgacgcactg ctgaaagctg gctttggttt ctaccatgat    960

cgttggggtc cgaacgtggt tcgctttgtt accagcttcg ctaccacggc ggaagatgtg   1020

gaccacctgc tgaatcaggt tcgcctggcc gcagaccgta cgcaagaacg c            1071
```

```
<210> SEQ ID NO 2
<211> LENGTH: 357
<212> TYPE: PRT
<213> ORGANISM: Pseudomonas putida

<400> SEQUENCE: 2

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His Pro Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Arg Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205
```

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ser Ser Lys Met Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Gly Phe Tyr His Asp
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355

<210> SEQ ID NO 3
<211> LENGTH: 1071
<212> TYPE: DNA
<213> ORGANISM: Artificial sequence
<220> FEATURE:
<223> OTHER INFORMATION: Engineered sequence

<400> SEQUENCE: 3
atgaacggtg aaacctcgcg tccgccggcg ctgggtttta gctctgatgg gattgctggt 60
gcaagcccgg aagtcgcaca ggcactggtg aaacatagtt ccggccaagc gggtccgtat 120
ggcaccgatg aactgacggc ccaggtgaaa cgtaaatttt gcgaaatctt cgaacgcgac 180
gtcgaagtgt tcctggttcc gaccggtacg gcagcaaacg cactgtgtct gtccgcaatg 240
accccgccgt ggggtaatat ttactgccat ccggcgtccc acatcaacaa tgatgaatgt 300
ggtgcgccgg aatttttctc aaacggcgcc aaactgatga ccgttgatgg tccggcagct 360
aaactggaca ttgtccgtct gcgcgaacgt acgcgcgaaa aagtgggtga tgttcatacc 420
acgcagccgg catgcgtctc tattacccaa gctacggaag tgggcagtat ctataccctg 480
gatgaaattg aagccatcgg tgacgtgtgc aaatcatcga gcctgggtct gcacatggat 540
ggctctcgtt ttgctaatgc gctggtgtcc ctgggctgtt caccggcaga aatgacctgg 600
aaagccggtg ttgacgcact gagttttggt gcgacgaaaa acggcgttct ggcggccgaa 660
gcaattgtcc tgttcaatac ctcgctggct acggaaatga gctatcgtcg caaacgtgcc 720
ggccacctgt ctagtaaaat gcgctttctg agcgctcaga tcgatgcgta cctgaccgat 780
gacctgtggc tgcgtaacgc ccgcaaagca aatgcagctg cgcagcgtct ggcccaaggt 840
ctggaaggcc tgggcggtgt tgaagtcctg ggcggtaccg aagcaaacat tctgttctgt 900
cgcctggatt ctgccatgat cgacgcactg ctgaaagctg gctttggttt ctaccatgat 960
cgttggggtc cgaacgtggt tcgctttgtt accagcttcg ctaccacggc ggaagatgtg 1020
gaccacctgc tgaatcaggt tcgcctggcc gcagaccgta cgcaagaacg c 1071

<210> SEQ ID NO 4
<211> LENGTH: 357

<212> TYPE: PRT
<213> ORGANISM: Artificial sequence
<220> FEATURE:
<223> OTHER INFORMATION: Engineered sequence

<400> SEQUENCE: 4

```
Met Asn Gly Glu Thr Ser Arg Pro Pro Ala Leu Gly Phe Ser Ser Asp
1               5                   10                  15

Gly Ile Ala Gly Ala Ser Pro Glu Val Ala Gln Ala Leu Val Lys His
            20                  25                  30

Ser Ser Gly Gln Ala Gly Pro Tyr Gly Thr Asp Glu Leu Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His Pro Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Arg Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ser Ser Lys Met Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Gly Phe Tyr His Asp
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 5
<211> LENGTH: 1071

<212> TYPE: DNA
<213> ORGANISM: Artificial sequence
<220> FEATURE:
<223> OTHER INFORMATION: Engineered sequence

<400> SEQUENCE: 5
atgaacggtg aaacctcgcg tccgccggcg ctgggtttta gctctgatga gattgctggt 60
gcaagcccgg aagtcgcaca ggcactggtg aaacatagtt ccggccaagc gggtccgtat 120
ggcaccgatg aactgacggc ccaggtgaaa cgtaaatttt gcgaaatctt cgaacgcgac 180
gtcgaagtgt tcctggttcc gaccggtacg gcagcaaacg cactgtgtct gtccgcaatg 240
accccgccgt ggggtaatat ttactgccat ccggcgtccc acatcaacaa tgatgaatgt 300
ggtgcgccgg aatttttctc aaacggcgcc aaactgatga ccgttgatgg tccggcagct 360
aaactggaca ttgtccgtct gcgcgaacgt acgcgcgaaa aagtgggtga tgttcatacc 420
acgcagccgg catgcgtctc tattacccaa gctacggaag tgggcagtat ctataccctg 480
gatgaaattg aagccatcgg tgacgtgtgc aaatcatcga gcctgggtct gcacatggat 540
ggctctcgtt ttgctaatgc gctggtgtcc ctgggctgtt caccggcaga aatgacctgg 600
aaagccggtg ttgacgcact gagttttggt gcgacgaaaa acggcgttct ggcggccgaa 660
gcaattgtcc tgttcaatac ctcgctggct acggaaatga gctatcgtcg caaacgtgcc 720
ggccacctgt ctagtaaaat gcgctttctg agcgctcaga tcgatgcgta cctgaccgat 780
gacctgtggc tgcgtaacgc ccgcaaagca aatgcagctg cgcagcgtct ggcccaaggt 840
ctggaaggcc tgggcggtgt tgaagtcctg ggcggtaccg aagcaaacat tctgttctgt 900
cgcctggatt ctgccatgat cgacgcactg ctgaaagctg gctttggttt ctaccatgat 960
cgttggggtc cgaacgtggt tcgctttgtt accagcttcg ctaccacggc ggaagatgtg 1020
gaccacctgc tgaatcaggt tcgcctggcc gcagaccgta cgcaagaacg c 1071

<210> SEQ ID NO 6
<211> LENGTH: 357
<212> TYPE: PRT
<213> ORGANISM: Artificial sequence
<220> FEATURE:
<223> OTHER INFORMATION: Engineered sequence

<400> SEQUENCE: 6

Met Asn Gly Glu Thr Ser Arg Pro Pro Ala Leu Gly Phe Ser Ser Asp
1 5 10 15

Glu Ile Ala Gly Ala Ser Pro Glu Val Ala Gln Ala Leu Val Lys His
20 25 30

Ser Ser Gly Gln Ala Gly Pro Tyr Gly Thr Asp Glu Leu Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His Pro Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Arg Glu Lys Val Gly Asp Val His Thr Thr Gln Pro Ala
130 135 140

```
Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ser Ser Lys Met Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Gly Phe Tyr His Asp
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 7
<211> LENGTH: 1071
<212> TYPE: DNA
<213> ORGANISM: Artificial sequence
<220> FEATURE:
<223> OTHER INFORMATION: Engineered sequence

<400> SEQUENCE: 7

```
atgaacggtg aaacctcgcg tccgccggcg ctgggtttta gctctgataa tattgctggt     60

gcaagcccgg aagtcgcaca ggcactggtg aaacatagtt ccggccaagc gggtctgtat    120

ggcaccgatg aactgacggc ccaggtgaaa cgtaaatttt gcgaaatctt cgaacgcgac    180

gtcgaagtgt tcctggttcc gaccggtacg gcagcaaacg cactgtgtct gtccgcaatg    240

accccgccgt ggggtaatat ttactgccat ccggcgtccc acatcaacaa tgatgaatgt    300

ggtgcgccgg aatttttctc aaacggcgcc aaactgatga ccgttgatgg tccggcagct    360

aaactggaca ttgtccgtct gcgcgaacgt acgcgcgaaa aagtgggtga tgttcatacc    420

acgcagccgg catgcgtctc tattacccaa gctacggaag tgggcagtat ctataccctg    480

gatgaaattg aagccatcgg tgacgtgtgc aaatcatcga gcctgggtct gcacatggat    540

ggctctcgtt ttgctaatgc gctggtgtcc ctgggctgtt caccggcaga aatgacctgg    600

aaagccggtg ttgacgcact gagttttggt gcgacgaaaa acggcgttct ggcggccgaa    660

gcaattgtcc tgttcaatac ctcgctggct acggaaatga gctatcgtcg caaacgtgcc    720

ggccacctgt ctagtaaaat gcgctttctg agcgctcaga tcgatgcgta cctgaccgat    780
```

-continued

```
gacctgtggc tgcgtaacgc ccgcaaagca aatgcagctg cgcagcgtct ggcccaaggt    840

ctggaaggcc tgggcggtgt tgaagtcctg ggcggtaccg aagcaaacat tctgttctgt    900

cgcctggatt ctgccatgat cgacgcactg ctgaaagctg gctttggttt ctaccatgat    960

cgttggggtc cgaacgtggt tcgctttgtt accagcttcg ctaccacggc ggaagatgtg   1020

gaccacctgc tgaatcaggt tcgcctggcc gcagaccgta cgcaagaacg c            1071


<210> SEQ ID NO 8
<211> LENGTH: 357
<212> TYPE: PRT
<213> ORGANISM: Artificial sequence
<220> FEATURE:
<223> OTHER INFORMATION: Engineered sequence

<400> SEQUENCE: 8

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Leu Tyr Gly Thr Asp Glu Leu Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His Pro Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Arg Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ser Ser Lys Met Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Gly Phe Tyr His Asp
305                 310                 315                 320
```

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 9
<211> LENGTH: 1071
<212> TYPE: DNA
<213> ORGANISM: Artificial sequence
<220> FEATURE:
<223> OTHER INFORMATION: Engineered sequence

<400> SEQUENCE: 9
atgaacggtg aaacctcgcg tccgccggcg ctgggtttta gctctgataa tattgctggt 60
gcaagcccgg aagtcgcaca ggcactggtg aaacatagtt ccggccaagc gggtccgtat 120
tataccgatg aactgacggc ccaggtgaaa cgtaaatttt gcgaaatctt cgaacgcgac 180
gtcgaagtgt tcctggttcc gaccggtacg gcagcaaacg cactgtgtct gtccgcaatg 240
accccgccgt ggggtaatat ttactgccat ccggcgtccc acatcaacaa tgatgaatgt 300
ggtgcgccgg aatttttctc aaacggcgcc aaactgatga ccgttgatgg tccggcagct 360
aaactggaca ttgtccgtct gcgcgaacgt acgcgcgaaa aagtgggtga tgttcatacc 420
acgcagccgg catgcgtctc tattacccaa gctacggaag tgggcagtat ctataccctg 480
gatgaaattg aagccatcgg tgacgtgtgc aaatcatcga gcctgggtct gcacatggat 540
ggctctcgtt ttgctaatgc gctggtgtcc ctgggctgtt caccggcaga aatgacctgg 600
aaagccggtg ttgacgcact gagttttggt gcgacgaaaa acggcgttct ggcggccgaa 660
gcaattgtcc tgttcaatac ctcgctggct acggaaatga gctatcgtcg caaacgtgcc 720
ggccacctgt ctagtaaaat gcgctttctg agcgctcaga tcgatgcgta cctgaccgat 780
gacctgtggc tgcgtaacgc ccgcaaagca aatgcagctg cgcagcgtct ggcccaaggt 840
ctggaaggcc tgggcggtgt tgaagtcctg ggcggtaccg aagcaaacat tctgttctgt 900
cgcctggatt ctgccatgat cgacgcactg ctgaaagctg gctttggttt ctaccatgat 960
cgttggggtc cgaacgtggt tcgctttgtt accagcttcg ctaccacggc ggaagatgtg 1020
gaccacctgc tgaatcaggt tcgcctggcc gcagaccgta cgcaagaacg c 1071

<210> SEQ ID NO 10
<211> LENGTH: 357
<212> TYPE: PRT
<213> ORGANISM: Artificial sequence
<220> FEATURE:
<223> OTHER INFORMATION: Engineered sequence

<400> SEQUENCE: 10

Met Asn Gly Glu Thr Ser Arg Pro Pro Ala Leu Gly Phe Ser Ser Asp
1 5 10 15

Asn Ile Ala Gly Ala Ser Pro Glu Val Ala Gln Ala Leu Val Lys His
20 25 30

Ser Ser Gly Gln Ala Gly Pro Tyr Tyr Thr Asp Glu Leu Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met

```
65                  70                  75                  80

Thr Pro Pro Trp Gly Asn Ile Tyr Cys His Pro Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Arg Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ser Ser Lys Met Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Gly Phe Tyr His Asp
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 11
<211> LENGTH: 1071
<212> TYPE: DNA
<213> ORGANISM: Artificial sequence
<220> FEATURE:
<223> OTHER INFORMATION: Engineered sequence

<400> SEQUENCE: 11

```
atgaacggtg aaacctcgcg tccgccggcg ctgggtttta gctctgataa tattgctggt      60

gcaagcccgg aagtcgcaca ggcactggtg aaacatagtt ccggccaagc gggtccgtat     120

ggcacccctg aactgacggc ccaggtgaaa cgtaaatttt gcgaaatctt cgaacgcgac     180

gtcgaagtgt tcctggttcc gaccggtacg gcagcaaacg cactgtgtct gtccgcaatg     240

accccgccgt ggggtaatat ttactgccat ccggcgtccc acatcaacaa tgatgaatgt     300

ggtgcgccgg aatttttctc aaacggcgcc aaactgatga ccgttgatgg tccggcagct     360

aaactggaca ttgtccgtct gcgcgaacgt acgcgcgaaa aagtgggtga tgttcatacc     420
```

```
acgcagccgg catgcgtctc tattacccaa gctacggaag tgggcagtat ctataccctg    480

gatgaaattg aagccatcgg tgacgtgtgc aaatcatcga gcctgggtct gcacatggat    540

ggctctcgtt ttgctaatgc gctggtgtcc ctgggctgtt caccggcaga aatgacctgg    600

aaagccggtg ttgacgcact gagttttggt gcgacgaaaa acggcgttct ggcggccgaa    660

gcaattgtcc tgttcaatac ctcgctggct acggaaatga gctatcgtcg caaacgtgcc    720

ggccacctgt ctagtaaaat gcgctttctg agcgctcaga tcgatgcgta cctgaccgat    780

gacctgtggc tgcgtaacgc ccgcaaagca aatgcagctg cgcagcgtct ggcccaaggt    840

ctggaaggcc tgggcggtgt tgaagtcctg ggcggtaccg aagcaaacat tctgttctgt    900

cgcctggatt ctgccatgat cgacgcactg ctgaaagctg gctttggttt ctaccatgat    960

cgttggggtc cgaacgtggt tcgctttgtt accagcttcg ctaccacggc ggaagatgtg   1020

gaccacctgc tgaatcaggt tcgcctggcc gcagaccgta cgcaagaacg c            1071


<210> SEQ ID NO 12
<211> LENGTH: 357
<212> TYPE: PRT
<213> ORGANISM: Artificial sequence
<220> FEATURE:
<223> OTHER INFORMATION: Engineered sequence

<400> SEQUENCE: 12

Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Pro Glu Leu Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His Pro Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Arg Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ser Ser Lys Met Arg Phe Leu Ser Ala Gln Ile Asp Ala
```

```
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Gly Phe Tyr His Asp
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 13
<211> LENGTH: 1071
<212> TYPE: DNA
<213> ORGANISM: Artificial sequence
<220> FEATURE:
<223> OTHER INFORMATION: Engineered sequence

<400> SEQUENCE: 13

atgaacggtg aaacctcgcg tccgccggcg ctgggtttta gctctgataa tattgctggt      60

gcaagcccgg aagtcgcaca ggcactggtg aaacatagtt ccggccaagc gggtccgtat     120

ggcacctatg aactgacggc ccaggtgaaa cgtaaatttt gcgaaatctt cgaacgcgac     180

gtcgaagtgt tcctggttcc gaccggtacg gcagcaaacg cactgtgtct gtccgcaatg     240

accccgccgt ggggtaatat ttactgccat ccggcgtccc acatcaacaa tgatgaatgt     300

ggtgcgccgg aatttttctc aaacggcgcc aaactgatga ccgttgatgg tccggcagct     360

aaactggaca ttgtccgtct gcgcgaacgt acgcgcgaaa aagtgggtga tgttcatacc     420

acgcagccgg catgcgtctc tattacccaa gctacggaag tgggcagtat ctataccctg     480

gatgaaattg aagccatcgg tgacgtgtgc aaatcatcga gcctgggtct gcacatggat     540

ggctctcgtt ttgctaatgc gctggtgtcc ctgggctgtt caccggcaga aatgacctgg     600

aaagccggtg ttgacgcact gagttttggt gcgacgaaaa acggcgttct ggcggccgaa     660

gcaattgtcc tgttcaatac ctcgctggct acggaaatga gctatcgtcg caaacgtgcc     720

ggccacctgt ctagtaaaat gcgctttctg agcgctcaga tcgatgcgta cctgaccgat     780

gacctgtggc tgcgtaacgc ccgcaaagca aatgcagctg cgcagcgtct ggcccaaggt     840

ctggaaggcc tgggcggtgt tgaagtcctg ggcggtaccg aagcaaacat tctgttctgt     900

cgcctggatt ctgccatgat cgacgcactg ctgaaagctg gctttggttt ctaccatgat     960

cgttggggtc cgaacgtggt tcgctttgtt accagcttcg ctaccacggc ggaagatgtg    1020

gaccacctgc tgaatcaggt tcgcctggcc gcagaccgta cgcaagaacg c             1071


<210> SEQ ID NO 14
<211> LENGTH: 357
<212> TYPE: PRT
<213> ORGANISM: Artificial sequence
<220> FEATURE:
<223> OTHER INFORMATION: Engineered sequence

<400> SEQUENCE: 14
```

-continued

```
Met Asn Gly Glu Thr Ser Arg Pro Pro Ala Leu Gly Phe Ser Ser Asp
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Tyr Glu Leu Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His Pro Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Arg Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ser Ser Lys Met Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Gly Phe Tyr His Asp
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 15
<211> LENGTH: 1071
<212> TYPE: DNA
<213> ORGANISM: Artificial sequence
<220> FEATURE:
<223> OTHER INFORMATION: Engineered sequence

<400> SEQUENCE: 15

-continued

```
atgaacggtg aaacctcgcg tccgccggcg ctgggtttta gctctgaaaa tattgctggt     60
gcaagcccgg aagtcgcaca ggcactcgtt aagcacagtt cgggccaggc gggtccctat    120
ggtaccgatg atctgactgc tcaagttaaa cgtaaatttt gcgaaatctt cgaacgcgac    180
gtcgaagtgt tcctggttcc gaccggtacg gcagcaaacg cactgtgtct gtccgcaatg    240
accccgccgt ggggtaatat ttactgccat cacgcgtccc acatcaacaa tgatgaatgt    300
ggtgcgccgg aatttttctc aaacggcgcc aaactgatga ccgttgatgg tccggcagct    360
aaactggaca ttgtccgtct gcgcgaacgt acgtccgaaa aagtgggtga tgttcatacg    420
acgcagccgg catgcgtctc tattacccaa gctacggaag tgggcagtat ctataccctg    480
gatgaaattg aagccatcgg tgacgtgtgc aaatcatcga gcctgggtct gcacatggat    540
ggctctcgtt ttgctaatgc gctggtgtcc ctgggctgtt caccggcaga aatgacctgg    600
aaagccggtg ttgacgcact gagttttggt gcgacgaaaa acggcgttct ggcggccgaa    660
gcaattgtcc tgttcaatac ctcgctggct acggaaatga gctatcgtcg caaacgtgcc    720
ggccacctga tcagtaaata ccgctttctg agcgctcaga tcgatgcgta cctgaccgat    780
gacctgtggc tgcgtaacgc ccgcaaagca aatgcagctg cgcagcgtct ggcccaaggt    840
ctggaaggcc tgggcggtgt tgaagtcctg ggcggtaccg aagcaaacat tctgttctgt    900
cgcctggatt ctgccatgat cgacgcactg ctgaaagctg gctttaaatt cgggtacaag    960
cgttggggtc cgaacgtggt tcgctttgtt accagcttcg ctaccacggc ggaagatgtg   1020
gaccacctgc tgaatcaggt tcgcctggcc gcagaccgta cgcaagaacg c            1071
```

<210> SEQ ID NO 16
<211> LENGTH: 357
<212> TYPE: PRT
<213> ORGANISM: Artificial sequence
<220> FEATURE:
<223> OTHER INFORMATION: Engineered sequence

<400> SEQUENCE: 16

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Asp Leu Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175
```

-continued

```
Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 17
<211> LENGTH: 1071
<212> TYPE: DNA
<213> ORGANISM: Artificial sequence
<220> FEATURE:
<223> OTHER INFORMATION: Engineered sequence

<400> SEQUENCE: 17

```
atgaacggtg aaacctcgcg tccgccggcg ctgggtttta gctctgaaaa tattgctggt      60

gcaagcccgg aagtcgcaca ggcactcgtt aagcacagtt cgggccaggc gggtccctat     120

ggtaccgatg aaattactgc tcaagttaaa cgtaaatttt gcgaaatctt cgaacgcgac     180

gtcgaagtgt tcctggttcc gaccggtacg gcagcaaacg cactgtgtct gtccgcaatg     240

accccgccgt ggggtaatat ttactgccat cacgcgtccc acatcaacaa tgatgaatgt     300

ggtgcgccgg aatttttctc aaacggcgcc aaactgatga ccgttgatgg tccggcagct     360

aaactggaca ttgtccgtct gcgcgaacgt acgtccgaaa aagtgggtga tgttcatacg     420

acgcagccgg catgcgtctc tattacccaa gctacggaag tgggcagtat ctataccctg     480

gatgaaattg aagccatcgg tgacgtgtgc aaatcatcga gcctgggtct gcacatggat     540

ggctctcgtt ttgctaatgc gctggtgtcc ctgggctgtt caccggcaga aatgacctgg     600

aaagccggtg ttgacgcact gagttttggt gcgacgaaaa acggcgttct ggcggccgaa     660

gcaattgtcc tgttcaatac ctcgctggct acggaaatga gctatcgtcg caaacgtgcc     720

ggccacctga tcagtaaata ccgctttctg agcgctcaga tcgatgcgta cctgaccgat     780

gacctgtggc tgcgtaacgc ccgcaaagca aatgcagctg cgcagcgtct ggcccaaggt     840

ctggaaggcc tgggcggtgt tgaagtcctg ggcggtaccg aagcaaacat tctgttctgt     900

cgcctggatt ctgccatgat cgacgcactg ctgaaagctg gctttaaatt cgggtacaag     960

cgttggggtc cgaacgtggt tcgctttgtt accagcttcg ctaccacggc ggaagatgtg    1020
```

gaccacctgc tgaatcaggt tcgcctggcc gcagaccgta cgcaagaacg c 1071

<210> SEQ ID NO 18
<211> LENGTH: 357
<212> TYPE: PRT
<213> ORGANISM: Artificial sequence
<220> FEATURE:
<223> OTHER INFORMATION: Engineered sequence

<400> SEQUENCE: 18

Met Asn Gly Glu Thr Ser Arg Pro Pro Ala Leu Gly Phe Ser Ser Glu
1 5 10 15

Asn Ile Ala Gly Ala Ser Pro Glu Val Ala Gln Ala Leu Val Lys His
20 25 30

Ser Ser Gly Gln Ala Gly Pro Tyr Gly Thr Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Ala Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys Tyr Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Gly Gly Thr Glu Ala Asn Ile Leu Phe Cys Arg Leu Asp Ser
290 295 300

Ala Met Ile Asp Ala Leu Leu Lys Ala Gly Phe Lys Phe Gly Tyr Lys
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

-continued

Arg Thr Gln Glu Arg
355

<210> SEQ ID NO 19
<211> LENGTH: 1071
<212> TYPE: DNA
<213> ORGANISM: Artificial sequence
<220> FEATURE:
<223> OTHER INFORMATION: Engineered sequence

<400> SEQUENCE: 19
atgaacggtg aaacctcgcg tccgccggcg ctgggtttta gctctgaaaa tattgctggt 60
gcaagcccgg aagtcgcaca ggcactcgtt aagcacagtt cgggccaggc gggtccctat 120
ggcaccgatg aactgactca tcaagttaaa cgtaaatttt gcgaaatctt cgaacgcgac 180
gtcgaagtgt tcctggttcc gaccggtacg gcagcaaacg cactgtgtct gtccgcaatg 240
accccgccgt ggggtaatat ttactgccat cacgcgtccc acatcaacaa tgatgaatgt 300
ggtgcgccgg aatttttctc aaacggcgcc aaactgatga ccgttgatgg tccggcagct 360
aaactggaca ttgtccgtct gcgcgaacgt acgtccgaaa aagtgggtga tgttcatacg 420
acgcagccgg catgcgtctc tattacccaa gctacggaag tgggcagtat ctataccctg 480
gatgaaattg aagccatcgg tgacgtgtgc aaatcatcga gcctgggtct gcacatggat 540
ggctctcgtt ttgctaatgc gctggtgtcc ctgggctgtt caccggcaga aatgacctgg 600
aaagccggtg ttgacgcact gagttttggt gcgacgaaaa acggcgttct ggcggccgaa 660
gcaattgtcc tgttcaatac ctcgctggct acggaaatga gctatcgtcg caaacgtgcc 720
ggccacctga tcagtaaata ccgctttctg agcgctcaga tcgatgcgta cctgaccgat 780
gacctgtggc tgcgtaacgc ccgcaaagca aatgcagctg cgcagcgtct ggcccaaggt 840
ctggaaggcc tgggcggtgt tgaagtcctg ggcggtaccg aagcaaacat tctgttctgt 900
cgcctggatt ctgccatgat cgacgcactg ctgaaagctg gctttaaatt cgggtacaag 960
cgttggggtc cgaacgtggt tcgctttgtt accagcttcg ctaccacggc ggaagatgtg 1020
gaccacctgc tgaatcaggt tcgcctggcc gcagaccgta cgcaagaacg c 1071

<210> SEQ ID NO 20
<211> LENGTH: 357
<212> TYPE: PRT
<213> ORGANISM: Artificial sequence
<220> FEATURE:
<223> OTHER INFORMATION: Engineered sequence

<400> SEQUENCE: 20

Met Asn Gly Glu Thr Ser Arg Pro Pro Ala Leu Gly Phe Ser Ser Glu
1 5 10 15

Asn Ile Ala Gly Ala Ser Pro Glu Val Ala Gln Ala Leu Val Lys His
20 25 30

Ser Ser Gly Gln Ala Gly Pro Tyr Gly Thr Asp Glu Leu Thr His Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

```
Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355

<210> SEQ ID NO 21
<211> LENGTH: 1071
<212> TYPE: DNA
<213> ORGANISM: Artificial sequence
<220> FEATURE:
<223> OTHER INFORMATION: Engineered sequence

<400> SEQUENCE: 21

atgaatggtg aaaccagtcg tccgccggca ctgggtttta gcagcgaaaa cattgcaggc      60

gcaagtccgg aagttgcaca agcactggtt aaacatagct ctggtcaagc agatccgtac     120

ggtaccgatg aactgaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccagccgg cttgcgttag tattacccag gcaaccgaag ttggtagcat ctataccctg     480

gacgaaatcg aagcgattgg cgacgtctgc aaaagtagta gtctgccgct gcatatggac     540

ggtagtcgtt ttgcgaacgc actggttagt ctgggttgtt ctccggcaga aatgacctgg     600
```

-continued

```
aaagcaggtg ttgacgcact gagttttggc gcaaccaaaa acggcgttct ggctgcagaa    660

gcaattgttc tgtttaaccc gagcctggcc accgaaatga gctatcgtcg taaacgcgca    720

ggtcatctga ttagcaaata ccgtttcctg agcgcacaga ttgacgcata tctgaccgac    780

gatctgtggc tgcgtaacgc acgtaaagca aacgcagcag cacaacgtct ggcacaaggt    840

ctggaaggtc tgccgggcgt tgaagttctg ggcggtaccg aagcaaacat tctgttctgc    900

cgtctggatt ctgcgatgat tgacgcactg ctgaaagcgg gctttaaatt tggctataaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071


<210> SEQ ID NO 22
<211> LENGTH: 357
<212> TYPE: PRT
<213> ORGANISM: Artificial sequence
<220> FEATURE:
<223> OTHER INFORMATION: Engineered sequence

<400> SEQUENCE: 22

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Asp Pro Tyr Gly Thr Asp Glu Leu Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Pro
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Pro Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Pro Gly Val Glu
        275                 280                 285
```

Val Leu Gly Gly Thr Glu Ala Asn Ile Leu Phe Cys Arg Leu Asp Ser
290 295 300

Ala Met Ile Asp Ala Leu Leu Lys Ala Gly Phe Lys Phe Gly Tyr Lys
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 23
<211> LENGTH: 1071
<212> TYPE: DNA
<213> ORGANISM: Artificial sequence
<220> FEATURE:
<223> OTHER INFORMATION: Engineered sequence

<400> SEQUENCE: 23
atgaacggtg aaacctcgcg tccgccggcg ctgggtttta gctctgaaaa tattgctggt 60
gcaagcccgg aagtcgcaca ggcactcgtt aagcacagtt cgggccaggc gggtccctat 120
ggtaccgatg aaattactgc tcaagttaaa cgtaaatttt gcgaaatctt cgaacgcgac 180
gtcgaagtgt tcctggttcc gaccggtacg gcagcaaacg cactgtgtct gtccgcaatg 240
accccgccgt ggggtaatat ttactgccat tcggcgtccc acatcaacaa tgatgaatgt 300
ggtgcgccgg aatttttctc aaacggcgcc aaactgatga ccgttgatgg tccggcagct 360
aaactggaca ttgtccgtct gcgcgaacgt acgtccgaaa aagtgggtga tgttcatacg 420
acgcagccgg catgcgtctc tattacccaa gctacggaag tgggcagtat ctataccctg 480
gatgaaattg aagccatcgg tgacgtgtgc aaatcatcga gcctgggtct gcacatggat 540
ggctctcgtt ttgctaatgc gctggtgtcc ctgggctgtt caccggcaga aatgacctgg 600
aaagccggtg ttgacgcact gagttttggt gcgacgaaaa acggcgttct ggcggccgaa 660
gcaattgtcc tgttcaatac ctcgctggct acggaaatga gctatcgtcg caaacgtgcc 720
ggccacctga tcagtaaata ccgctttctg agcgctcaga tcgatgcgta cctgaccgat 780
gacctgtggc tgcgtaacgc ccgcaaagca aatgcagctg cgcagcgtct ggcccaaggt 840
ctggaaggcc tgggcggtgt tgaagtcctg ggcggtaccg aagcaaacat tctgttctgt 900
cgcctggatt ctgccatgat cgacgcactg ctgaaagctg gctttaaatt cgggtacaag 960
cgttggggtc cgaacgtggt tcgctttgtt accagcttcg ctaccacggc ggaagatgtg 1020
gaccacctgc tgaatcaggt tcgcctggcc gcagaccgta cgcaagaacg c 1071

<210> SEQ ID NO 24
<211> LENGTH: 357
<212> TYPE: PRT
<213> ORGANISM: Artificial sequence
<220> FEATURE:
<223> OTHER INFORMATION: Engineered sequence

<400> SEQUENCE: 24

Met Asn Gly Glu Thr Ser Arg Pro Pro Ala Leu Gly Phe Ser Ser Glu
1 5 10 15

Asn Ile Ala Gly Ala Ser Pro Glu Val Ala Gln Ala Leu Val Lys His
20 25 30

Ser Ser Gly Gln Ala Gly Pro Tyr Gly Thr Asp Glu Ile Thr Ala Gln

```
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His Ser Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 25
<211> LENGTH: 1071
<212> TYPE: DNA
<213> ORGANISM: Artificial sequence
<220> FEATURE:
<223> OTHER INFORMATION: Engineered sequence

<400> SEQUENCE: 25

```
atgaacggtg aaacctcgcg tccgccggcg ctgggtttta gctctgaaaa tattgctggt      60

gcaagcccgg aagtcgcaca ggcactcgtt aagcacagtt cgggccaggc gggtccctat     120

ggtaccgatg aaattactgc tcaagttaaa cgtaaatttt gcgaaatctt cgaacgcgac     180

gtcgaagtgt tcctggttcc gaccggtacg gcagcaaacg cactgtgtct gtccgcaatg     240
```

```
accccgccgt ggggtaatat ttactgccat catgcgtccc acatcaacaa tgatgaatgt    300

ggtgcgccgg aatttttctc aaacggcgcc aaactgatga ccgttgatgg tccggcagct    360

aaactggaca ttgtccgtct gcgcgaacgt acgtccgaaa aagtgggtga tgttcatacg    420

acgcagccgg catgcgtctc tattacccaa gctacggaag tgggcagtat ctataccctg    480

gatgaaattg aagccatcgg tgacgtgtgc aaatcatcga gcctgggtct gcacatggat    540

ggctctcgtt ttgctaatgc gctggtgtcc ctgggctgtt caccggcaga aatgacctgg    600

aaagccggtg ttgacgcact gagttttggt gcgacgaaaa acggcgttct ggcggccgaa    660

gcaattgtcc tgttcaatac ctcgctggct acggaaatga gctatcgtcg caaacgtgcc    720

ggccacctga tcagtaaata ccgctttctg agcgctcaga tcgatgcgta cctgaccgat    780

gacctgtggc tgcgtaacgc ccgcaaagca aatgcagctg cgcagcgtct ggcccaaggt    840

ctggaaggcc tgggcggtgt tgaagtcctg ggcggtaccg aagcaaacat tctgttctgt    900

cgcctggatt ctaccatgat cgacgcactg ctgaaagctg gctttaaatt cgggtacaag    960

cgttggggtc cgaacgtggt tcgctttgtt accagcttcg ctaccacggc ggaagatgtg   1020

gaccacctgc tgaatcaggt tcgcctggcc gcagaccgta cgcaagaacg c            1071


<210> SEQ ID NO 26
<211> LENGTH: 357
<212> TYPE: PRT
<213> ORGANISM: Artificial sequence
<220> FEATURE:
<223> OTHER INFORMATION: Engineered sequence

<400> SEQUENCE: 26

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
```

```
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Thr Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 27
<211> LENGTH: 1071
<212> TYPE: DNA
<213> ORGANISM: Artificial sequence
<220> FEATURE:
<223> OTHER INFORMATION: Engineered sequence

<400> SEQUENCE: 27

```
atgaacggtg aaacctcgcg tccgccggcg ctgggtttta gctctgaaaa tattgctggt     60

gcaagcccgg aagtcgcaca ggcactcgtt aagcacagtt cgggccaggc gggtccctat    120

ggtaccgatg aaattactgc tcaagttaaa cgtaaatttt gcgaaatctt cgaacgcgac    180

gtcgaagtgt tcctggttcc gaccggtacg gcagcaaacg cactgtgtct gtccgcaatg    240

accccgccgt ggggtaatat ttactgccat cacgcgtccc acatcaacaa tgatgaatgt    300

ggtgcgccgg aatttttctc aaacggcgcc aaactgatga ccgttgatgg tccggcagct    360

aaactggaca ttgtccgtct gcgcgaacgt acgtccgaaa aagtgggtga tgttcatacg    420

acgcagccgg catgcgtctc tattacccaa gctacggaag tgggcagtat ctataccctg    480

gatgaaattg aagccatcgg tgacgtgtgc aaatcatcga gcctgggtct gcacatggat    540

ggctctcgtt ttgctaatgc gctggtgtcc ctgggctgtt caccggcaga aatgacctgg    600

aaagccggtg ttgacgcact gagttttggt gcgacgaaaa acggcgttct ggcggccgaa    660

gcaattgtcc tgttcaatac ctcgctggct acggaaatga gctatcgtcg caaacgtgcc    720

ggccacctga tcagtaaata ccgctttctg agcgctcaga tcgatgcgta cctgaccgat    780

gacctgtggc tgcgtaacgc ccgcaaagca aatgcagctg cgcagcgtct ggcccaaggt    840

ctggaaggcc tgggcggtgt tgaagtcctg ggcggtaccg aagcaaacat tctgttctgt    900

cgcctggatt ctgccatgat cgacgcactg ctgaaagctg gcttttcttt cgggtacaag    960

cgttggggtc cgaacgtggt tcgctttgtt accagcttcg ctaccacggc ggaagatgtg   1020

gaccacctgc tgaatcaggt tcgcctggcc gcagaccgta cgcaagaacg c            1071
```

<210> SEQ ID NO 28
<211> LENGTH: 357
<212> TYPE: PRT

-continued

<213> ORGANISM: Artificial sequence
<220> FEATURE:
<223> OTHER INFORMATION: Engineered sequence

<400> SEQUENCE: 28

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Ser Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 29
<211> LENGTH: 1071
<212> TYPE: DNA

<213> ORGANISM: Artificial sequence
<220> FEATURE:
<223> OTHER INFORMATION: Engineered sequence

<400> SEQUENCE: 29

```
atgaacggtg aaacctcgcg tccgccggcg ctgggtttta gctctgaaaa tattgctggt     60
gcaagcccgg aagtcgcaca ggcactcgtt aagcacagtt cgggccaggc gggtccctat    120
ggtaccgatg aaattactgc tcaagttaaa cgtaaatttt gcgaaatctt cgaacgcgac    180
gtcgaagtgt tcctggttcc gaccggtacg gcagcaaacg cactgtgtct gtccgcaatg    240
accccgccgt ggggtaatat ttactgccat cacgcgtccc acatcaacaa tgatgaatgt    300
ggtgcgccgg aatttttctc aaacggcgcc aaactgatga ccgttgatgg tccggcagct    360
aaactggaca ttgtccgtct gcgcgaacgt acgtccgaaa aagtgggtga tgttcatacg    420
acgcagccgg catgcgtctc tattacccaa gctacggaag tgggcagtat ctataccctg    480
gatgaaattg aagccatcgg tgacgtgtgc aaatcatcga gcctgggtct gcacatggat    540
ggctctcgtt ttgctaatgc gctggtgtcc ctgggctgtt caccggcaga aatgacctgg    600
aaagccggtg ttgacgcact gagttttggt gcgacgaaaa acggcgttct ggcggccgaa    660
gcaattgtcc tgttcaatac ctcgctggct acggaaatga gctatcgtcg caaacgtgcc    720
ggccacctga tcagtaaata ccgctttctg agcgctcaga tcgatgcgta cctgaccgat    780
gacctgtggc tgcgtaacgc ccgcaaagca aatgcagctg cgcagcgtct ggcccaaggt    840
ctggaaggcc tgggcggtgt tgaagtcctg ggcggtaccg aagcaaacat tctgttctgt    900
cgcctggatt ctgccatgat cgacgcactg ctgaaagctg gctttaaatt cggggttaag    960
cgttggggtc cgaacgtggt tcgctttgtt accagcttcg ctaccacggc ggaagatgtg   1020
gaccacctgc tgaatcaggt tcgcctggcc gcagaccgta cgcaagaacg c            1071
```

<210> SEQ ID NO 30
<211> LENGTH: 357
<212> TYPE: PRT
<213> ORGANISM: Artificial sequence
<220> FEATURE:
<223> OTHER INFORMATION: Engineered sequence

<400> SEQUENCE: 30

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140
```

```
Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Lys Phe Gly Val Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 31
<211> LENGTH: 1071
<212> TYPE: DNA
<213> ORGANISM: Artificial sequence
<220> FEATURE:
<223> OTHER INFORMATION: Engineered sequence

<400> SEQUENCE: 31

```
atgaacggtg aaacctcgcg tccgccggcg ctgggtttta gctctgaaaa tattgctggt     60

gcaagcccgg aagtcgcaca ggcactcgtt aagcacagtt cgggccaggc gggtccctat    120

ggtaccgatg aaattactgc tcttgttaaa cgtaaatttt gcgaaatctt cgaacgcgac    180

gtcgaagtgt tcctggttcc gaccggtacg gcagcaaacg cactgtgtct gtccgcaatg    240

accccgccgt ggggtaatat ttactgccat cacgcgtccc acatcaacaa tgatgaatgt    300

ggtgcgccgg aatttttctc aaacggcgcc aaactgatga ccgttgatgg tccggcagct    360

aaactggaca ttgtccgtct gcgcgaacgt acgtccgaaa aagtgggtga tgttcatacg    420

acgcagccgg catgcgtctc tattacccaa gctacggaag tgggcagtat ctataccctg    480

gatgaaattg aagccatcgg taacgtgtgc aaatcatcga gcctgggtct gcacatggat    540

ggctctcgtt ttgctaatgc gctggtgtcc ctgggctgtt caccggcaga aatgacctgg    600

aaagccggtg ttgacgcact gagttttggt gcgacgaaaa acggcgttct ggcggccgaa    660

gcaattgtcc tgttcaatac ctcgctggct acggaaatga gctatcgtcg caaacgtgcc    720

ggccacctga tcagtaaata ccgctttctg agcgctcaga tcgatgcgta cctgaccgat    780

gacctgtggc tgcgtaacgc ccgcaaagca aatgcagctg cgcagcgtct ggcccaaggt    840
```

```
ctggaaggcc tgggcggtgt tgaagtcctg ggcggtaccg aagcaaacat tctgttctgt    900

cgcctggatt ctgccatgat cgacgcactg ctgaaagctg gctttaaatt cgggtacaag    960

cgttggggtc cgaacgtggt tcgctttgtt accagcttcg ctaccacggc ggaagatgtg   1020

gaccacctgc tgaatcaggt tcgcctggcc gcagaccgta cgcaagaacg c            1071


<210> SEQ ID NO 32
<211> LENGTH: 357
<212> TYPE: PRT
<213> ORGANISM: Artificial sequence
<220> FEATURE:
<223> OTHER INFORMATION: Engineered sequence

<400> SEQUENCE: 32

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Ile Thr Ala Leu
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asn Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Lys Phe Gly Tyr Lys
305                 310                 315                 320
```

```
Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 33
<211> LENGTH: 1071
<212> TYPE: DNA
<213> ORGANISM: Artificial sequence
<220> FEATURE:
<223> OTHER INFORMATION: Engineered sequence

<400> SEQUENCE: 33

atgaacggtg aaacctcgcg tccgccggcg ctgggtttta gctctgaaaa tattgctggt      60

gcaagcccgg aagtcgcaca ggcactcgtt aagcacagtt cgggccaggc gggtccctat     120

ggtaccgatg aaattactgc tcaatcgaaa cgtaaatttt gcgaaatctt cgaacgcgac     180

gtcgaagtgt tcctggttcc gaccggtacg gcagcaaacg cactgtgtct gtccgcaatg     240

accccgccgt ggggtaatat ttactgccat cacgcgtccc acatcaacaa tgatgaatgt     300

ggtgcgccgg aatttttctc aaacggcgcc aaactgatga ccgttgatgg tccggcagct     360

aaactggaca ttgtccgtct gcgcgaacgt acgtccgaaa aagtgggtga tgttcatacg     420

acgcagccgg catgcgtctc tattacccaa gctacggaag tgggcagtat ctataccctg     480

gatgaaattg aagccatcgg tgacgtgtgc aaatcatcga gcctgggtct gcacatggat     540

ggctctcgtt ttgctaatgc gctggtgtcc ctgggctgtt caccggcaga aatgacctgg     600

aaagccggtg ttgacgcact gagttttggt gcgacgaaaa acggcgttct ggcggccgaa     660

gcaattgtcc tgttcaatac ctcgctggct acggaaatga gctatcgtcg caaacgtgcc     720

ggccacctga tcagtaaata ccgctttctg agcgctcaga tcgatgcgta cctgaccgat     780

gacctgtggc tgcgtaacgc ccgcaaagca aatgcagctg cgcagcgtct ggcccaaggt     840

ctggaaggcc tgggcggtgt tgaagtcctg ggcggtacca aagcaaacat tctgttctgt     900

cgcctggatt ctgccatgat cgacgcactg ctgaaagctg gctttaaatt cgggtacaag     960

cgttggggtc cgaacgtggt tcgctttgtt accagcttcg ctaccacggc ggaagatgtg    1020

gaccacctgc tgaatcaggt tcgcctggcc gcagaccgta cgcaagaacg c             1071


<210> SEQ ID NO 34
<211> LENGTH: 357
<212> TYPE: PRT
<213> ORGANISM: Artificial sequence
<220> FEATURE:
<223> OTHER INFORMATION: Engineered sequence

<400> SEQUENCE: 34

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Ile Thr Ala Gln
        35                  40                  45

Ser Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80
```

```
Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Lys Ala Asn Ile Leu Phe Cys Arg Leu Asp Ser
    290                 295                 300

Ala Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 35
<211> LENGTH: 1071
<212> TYPE: DNA
<213> ORGANISM: Artificial sequence
<220> FEATURE:
<223> OTHER INFORMATION: Engineered sequence

<400> SEQUENCE: 35

```
atgaacggtg aaacctcgcg tccgccggcg ctgggtttta gctctgaaaa tattgctggt      60

gcaagcccgg aagtcgcaca ggcactcgtt aagcacagtt cgggccaggc gggtccctat     120

ggtaccgatg aaattactgc tcaagttaaa cgtaaatttt gcgaaatctt cgaacgcgac     180

gtcgaagtgt tcttggttcc gaccggtacg gcagcaaacg cactgtgtct gtccgcaatg     240

accccgccgt ggggtaatat ttactgccat cacgcgtccc acatcaacaa tgatgaatgt     300

ggtgcgccgg aatttttctc aaacggcgcc aaactgatga ccgttgatgg tccggcagct     360

aaactggaca ttgtccgtct gcgcgaacgt acgtccgaac aagtgggtga tgttcatacg     420
```

-continued

```
acgcagccgg catgcgtctc tattacccaa gctacggaag tgggcagtat ctataccctg    480

gatgaaattg aagccatcgg tgacgtgtgc aaatcatcga gcctgggtct gcacatggat    540

ggctctcgtt ttgctaatgc gctggtgtcc ctgggctgtt caccggcaga aatgacctgg    600

aaagccggtg ttgacgcact gagttttggt gcgacgaaaa acggcgttct ggcggccgaa    660

gcaattgtcc tgttcaatac ctcgctggct acggaaatga gctatcgtcg caaacgtgcc    720

ggccacctga tcagtaaata ccgctttctg agcgctcaga tcgatgcgta cctgaccgat    780

gacctgtggc tgcgtaacgc ccgcaaagca aatgcagctg cgcagcgtct ggcccaaggt    840

ctggaaggcc tgggcggtgt tgaagtcctg ggcggtaccg aagcaaacat tctgttctgt    900

cgcctggatt ctgccatgat cgacgcactg ctgaaagctg gctttaaatt cgggtacaag    960

cgttggggtc cgaacgtggt tcgctttgtt accagcttcg ctaccacggc ggaagatgtg   1020

gaccacctgc tgaatcaggt tcgcctggcc gcagaccgta cgcaagaacg c            1071


<210> SEQ ID NO 36
<211> LENGTH: 357
<212> TYPE: PRT
<213> ORGANISM: Artificial sequence
<220> FEATURE:
<223> OTHER INFORMATION: Engineered sequence

<400> SEQUENCE: 36

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Gln Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255
```

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Gly Gly Thr Glu Ala Asn Ile Leu Phe Cys Arg Leu Asp Ser
290 295 300

Ala Met Ile Asp Ala Leu Leu Lys Ala Gly Phe Lys Phe Gly Tyr Lys
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 37
<211> LENGTH: 1071
<212> TYPE: DNA
<213> ORGANISM: Artificial sequence
<220> FEATURE:
<223> OTHER INFORMATION: Engineered sequence

<400> SEQUENCE: 37
atgaacggtg aaacctcgcg tccgccggcg ctgggtttta gctctgaaaa tattgctggt 60
gcaagcccgg aagtcgtaca ggcactcgtt aagcacagtt cgggccaggc gggtccctat 120
ggtaccgatg aaattactgc tcaagttaaa cgtaaatttt gcgaaatctt cgaacgcgac 180
gtcgaagtgt tcctggttcc gaccggtacg gcagcaaacg cactgtgtct gtccgcaatg 240
accccgccgt ggggtaatat ttactgccat cacgcgtccc acatcaacaa tgatgaatgt 300
ggtgcgccgg aatttttctc aaacggcgcc aaactgatga ccgttgatgg tccggcagct 360
aaactggaca ttgtccgtct gcgcgaacgt acgtccgaaa aagtgggtga tgttcatacg 420
acgcagccgg catgcgtctc tattacccaa gctacggaag tgggcagtat ctataccctg 480
gatgaaattg aagccatcgg tgacgtgtgc aaatcatcga gcctgggtct gcacatggat 540
ggctctcgtt ttgctaatgc gctggtgtcc ctgggctgtt caccggcaga aatgacctgg 600
aaagccggtg ttgacgcact gagttttggt gcgacgaaaa acggcgttct ggcggccgaa 660
gcaattgtcc tgttcaatac ctcgctggct acggaaatga gctatcgtcg caaacgtgcc 720
ggccacctga tcagtaaata ccgctttctg agcgctcaga tcgatgcgta cctgaccgat 780
gacctgtggc tgcgtaacgc ccgcaaagca aatgcagctg cgcagcgtct ggcccaaggt 840
ctggaaggcc tgggcggtgt tgaagtcctg ggcggtaccg aagcaaacat tctgttctgt 900
cgcctggatt ctgcaatgat cgacgcactg ctgaaagctg gctttaaatt cgggtacaag 960
cgttggggtc cgaacgtggt tcgctttgtt accagcttcg ctaccacggc ggaagatgtg 1020
gaccacctgc tgaatcaggt tcgcctggcc gcagaccgta cgcaagaacg c 1071

<210> SEQ ID NO 38
<211> LENGTH: 357
<212> TYPE: PRT
<213> ORGANISM: Artificial sequence
<220> FEATURE:
<223> OTHER INFORMATION: Engineered sequence

<400> SEQUENCE: 38

Met Asn Gly Glu Thr Ser Arg Pro Pro Ala Leu Gly Phe Ser Ser Glu

-continued

```
1               5                   10                  15

Asn Ile Ala Gly Ala Ser Pro Glu Val Val Gln Ala Leu Val Lys His
            20                  25                  30

Ser Ser Gly Gln Ala Gly Pro Tyr Gly Thr Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 39
<211> LENGTH: 1071
<212> TYPE: DNA
<213> ORGANISM: Artificial sequence
<220> FEATURE:
<223> OTHER INFORMATION: Engineered sequence

<400> SEQUENCE: 39

atgaatggtg aaaccagtcg tccgccggca ctgggtttta gcagcgaaaa cattgcaggc     60
```

gcaagtccgg aagttctgca agcactggtt aaacatagca gcggtcaagc tggtccgtat 120
ggtaccgatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcc gtgcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttaaatt tggctataaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 40
<211> LENGTH: 357
<212> TYPE: PRT
<213> ORGANISM: Artificial sequence
<220> FEATURE:
<223> OTHER INFORMATION: Engineered sequence

<400> SEQUENCE: 40

Met Asn Gly Glu Thr Ser Arg Pro Pro Ala Leu Gly Phe Ser Ser Glu
1 5 10 15

Asn Ile Ala Gly Ala Ser Pro Glu Val Leu Gln Ala Leu Val Lys His
20 25 30

Ser Ser Gly Gln Ala Gly Pro Tyr Gly Thr Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Arg Ala Ile Gly Asp Val Cys Lys Ser Ser Ser Leu Gly
165 170 175

Leu His Met Asp Gly Ser Arg Phe Ala Asn Ala Leu Val Ser Leu Gly

```
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 41
<211> LENGTH: 1071
<212> TYPE: DNA
<213> ORGANISM: Artificial sequence
<220> FEATURE:
<223> OTHER INFORMATION: Engineered sequence

<400> SEQUENCE: 41

atgaatggtg aaaccagtcg tccgccggca ctgggtttta gcagcgaaaa cattgcaggc     60

gcaagtccgg aagttctgca agcactggtt aaacatagca gcggtcaagc tggtccgtat    120

ggtaccgatg atattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcc gtgcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtctggact ctgcgatgat tgacgcactg ctgaaagcgg gctttaaatt tggctataaa    960

cgctggggtc cgaacgttgt tcgttttgtc accagctttg caaccaccgc agaagacgtt   1020
```

gatcatctgc tgaaccaagt tcgtctggca gcagatcgta cccaagaacg t 1071

<210> SEQ ID NO 42
<211> LENGTH: 357
<212> TYPE: PRT
<213> ORGANISM: Artificial sequence
<220> FEATURE:
<223> OTHER INFORMATION: Engineered sequence

<400> SEQUENCE: 42

Met Asn Gly Glu Thr Ser Arg Pro Pro Ala Leu Gly Phe Ser Ser Glu
1 5 10 15

Asn Ile Ala Gly Ala Ser Pro Glu Val Leu Gln Ala Leu Val Lys His
20 25 30

Ser Ser Gly Gln Ala Gly Pro Tyr Gly Thr Asp Asp Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Arg Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Ala Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Gly Gly Thr Glu Ala Asn Ile Leu Phe Cys Arg Leu Asp Ser
290 295 300

Ala Met Ile Asp Ala Leu Leu Lys Ala Gly Phe Lys Phe Gly Tyr Lys
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg

355

<210> SEQ ID NO 43
<211> LENGTH: 1071
<212> TYPE: DNA
<213> ORGANISM: Artificial sequence
<220> FEATURE:
<223> OTHER INFORMATION: Engineered sequence

<400> SEQUENCE: 43
atgaatggtg aaaccagtcg tccgccggca ctgggtttta gcagcgaaaa cattgcaggc 60
gcaagtccgg aagttgcgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 44
<211> LENGTH: 357
<212> TYPE: PRT
<213> ORGANISM: Artificial sequence
<220> FEATURE:
<223> OTHER INFORMATION: Engineered sequence

<400> SEQUENCE: 44

Met Asn Gly Glu Thr Ser Arg Pro Pro Ala Leu Gly Phe Ser Ser Glu
1 5 10 15

Asn Ile Ala Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

```
Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 45
<211> LENGTH: 1071
<212> TYPE: DNA
<213> ORGANISM: Artificial sequence
<220> FEATURE:
<223> OTHER INFORMATION: Engineered sequence

<400> SEQUENCE: 45

```
atgaatggtg aaaccagtcg tccgccggca ctgggtttta gcagcgaaaa cattgcaggc      60

gcaagtccgg aagttgcgca agcactggtt aaacatagca gcggtcaagc tggtccgtat     120

ggtaccgatg atattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480

gacgaaatcc gtgcgattgg cgacgtctgc aaaagtagta gtctgggcct gcatatggac     540

ggtagtcgtt ttgcgaacgc actggttagt ctgggttgtt ctccggcaga aatgacctgg     600

aaagcaggtg ttgacgcact gagttttggc gcaaccaaaa acggcgttct ggctgcagaa     660
```

```
gcaattgttc tgtttaacac cagcctggcc accgaaatga gctatcgtcg taaacgcgca    720

ggtcatctga ttagcaaata tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctgcgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071


<210> SEQ ID NO 46
<211> LENGTH: 357
<212> TYPE: PRT
<213> ORGANISM: Artificial sequence
<220> FEATURE:
<223> OTHER INFORMATION: Engineered sequence

<400> SEQUENCE: 46

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Asp Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Arg Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285
```

-continued

```
Val Leu Gly Gly Thr Glu Ala Asn Ile Leu Phe Cys Arg Met Asp Ser
    290                 295                 300

Ala Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 47
<211> LENGTH: 1071
<212> TYPE: DNA
<213> ORGANISM: Artificial sequence
<220> FEATURE:
<223> OTHER INFORMATION: Engineered sequence

<400> SEQUENCE: 47

```
atgaatggtg aaaccagtcg tccgccggca ctgggtttta gcagcgaaaa cattgcaggc     60

gcaagtccgg aagttctgca agcactggtt aaacatagca gcggtcaagc tggtccgtat    120

ggtaccgatg atattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcc gtgcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaata tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtactg aagcaaacat tctgttctgc    900

cgtatggact ctgcgatgat tgacgcactg ctgaaagcgg gctttaaatt tggctataaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 48
<211> LENGTH: 357
<212> TYPE: PRT
<213> ORGANISM: Artificial sequence
<220> FEATURE:
<223> OTHER INFORMATION: Engineered sequence

<400> SEQUENCE: 48

```
Met Asn Gly Glu Thr Ser Arg Pro Pro Ala Leu Gly Phe Ser Ser Glu
1               5                   10                  15

Asn Ile Ala Gly Ala Ser Pro Glu Val Leu Gln Ala Leu Val Lys His
            20                  25                  30

Ser Ser Gly Gln Ala Gly Pro Tyr Gly Thr Asp Asp Ile Thr Ala Gln
        35                  40                  45
```

```
Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Arg Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Ala Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 49
<211> LENGTH: 1071
<212> TYPE: DNA
<213> ORGANISM: Artificial sequence
<220> FEATURE:
<223> OTHER INFORMATION: Engineered sequence

<400> SEQUENCE: 49

```
atgaatggtg aaaccagtcg tccgccggca ctgggtttta gcagcgaaaa cattgcaggc      60

gcaagtccgg aagttctgca agcactggtt aaacatagca gcggtcaagc tggtccgtat     120

ggtaccgatg aaattaccgc gcaggttaaa cgtaaattct gcgagatctt cgagcgcgac     180

gttgaagttt ttctggttcc gaccggtacc gctgctaacg cactgtgtct gtctgcaatg     240
```

-continued

```
accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcc gtgcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctgcgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

```
<210> SEQ ID NO 50
<211> LENGTH: 357
<212> TYPE: PRT
<213> ORGANISM: Artificial sequence
<220> FEATURE:
<223> OTHER INFORMATION: Engineered sequence

<400> SEQUENCE: 50

Met Asn Gly Glu Thr Ser Arg Pro Pro Ala Leu Gly Phe Ser Ser Glu
1               5                   10                  15

Asn Ile Ala Gly Ala Ser Pro Glu Val Leu Gln Ala Leu Val Lys His
            20                  25                  30

Ser Ser Gly Gln Ala Gly Pro Tyr Gly Thr Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Arg Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220
```

```
Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Ala Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 51
<211> LENGTH: 1071
<212> TYPE: DNA
<213> ORGANISM: Artificial sequence
<220> FEATURE:
<223> OTHER INFORMATION: Engineered sequence

<400> SEQUENCE: 51

```
atgaatggtg aaaccagtcg tccgccggca ctgggtttta gcagcgaaaa cattgcaggc     60

gcaagtccgg aagttctgca agcactggtt aaacatagca gcggtcaagc tggtccgtat    120

ggtaccgatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcc gtgcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaata tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtctggact ctgcgatgat tgacgcactg ctgaaagcgg gctttaaatt tggctataaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 52
<211> LENGTH: 357
<212> TYPE: PRT
<213> ORGANISM: Artificial sequence

```
<220> FEATURE:
<223> OTHER INFORMATION: Engineered sequence

<400> SEQUENCE: 52

Met Asn Gly Glu Thr Ser Arg Pro Pro Ala Leu Gly Phe Ser Ser Glu
1               5                   10                  15

Asn Ile Ala Gly Ala Ser Pro Glu Val Leu Gln Ala Leu Val Lys His
            20                  25                  30

Ser Ser Gly Gln Ala Gly Pro Tyr Gly Thr Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Arg Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 53
<211> LENGTH: 1071
<212> TYPE: DNA
<213> ORGANISM: Artificial sequence
```

<220> FEATURE:
<223> OTHER INFORMATION: Engineered sequence

<400> SEQUENCE: 53
atgaatggtg aaaccagtcg tccgccggca ctgggtttta gcagcgaaaa cattgcaggc 60
gcaagtccgg aagttctgca agcactggtt aaacatagca gcggtcaagc tggtccgtat 120
ggtaccgatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaata tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 54
<211> LENGTH: 357
<212> TYPE: PRT
<213> ORGANISM: Artificial sequence
<220> FEATURE:
<223> OTHER INFORMATION: Engineered sequence

<400> SEQUENCE: 54

Met Asn Gly Glu Thr Ser Arg Pro Pro Ala Leu Gly Phe Ser Ser Glu
1 5 10 15

Asn Ile Ala Gly Ala Ser Pro Glu Val Leu Gln Ala Leu Val Lys His
20 25 30

Ser Ser Gly Gln Ala Gly Pro Tyr Gly Thr Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu

```
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 55
<211> LENGTH: 1071
<212> TYPE: DNA
<213> ORGANISM: Artificial sequence
<220> FEATURE:
<223> OTHER INFORMATION: Engineered sequence

<400> SEQUENCE: 55

```
atgaatggtg aaaccagtcg tccgccggca ctgggtttta gcagcgaaaa cattgcaggc      60

gcaagtccgg aagttctgca agcactggtt aaacatagca gcggtcaagc tggtccgtat     120

ggtaccgatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480

gacgaaatcc gtgcgattgg cgacgtctgc aaaagtagta gtctgggcct gcatatggac     540

ggtagtcgtt ttgcgaacgc actggttagt ctgggttgtt ctccggcaga aatgacctgg     600

aaagcaggtg ttgacgcact gagttttggc gcaaccaaaa acggcgttct ggctgcagaa     660

gcaattgttc tgtttaacac cagcctggcc accgaaatga gctatcgtcg taaacgcgca     720

ggtcatctga ttagcaaaca tcgtttcctg agcgcacaga ttgacgcata tctgaccgac     780

gatctgtggc tgcgtaacgc acgtaaagca aacgcagcag cacaacgtct ggcacaaggt     840
```

```
ctggaaggtc tgggcggcgt tgaagttctg ggcggtaccg aagcaaacat tctgttctgc    900

cgtatggact ctgcgatgat tgacgcactg ctgaaagcgg gctttaaatt tggctataaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071


<210> SEQ ID NO 56
<211> LENGTH: 357
<212> TYPE: PRT
<213> ORGANISM: Artificial sequence
<220> FEATURE:
<223> OTHER INFORMATION: Engineered sequence

<400> SEQUENCE: 56

Met Asn Gly Glu Thr Ser Arg Pro Pro Ala Leu Gly Phe Ser Ser Glu
1               5                   10                  15

Asn Ile Ala Gly Ala Ser Pro Glu Val Leu Gln Ala Leu Val Lys His
            20                  25                  30

Ser Ser Gly Gln Ala Gly Pro Tyr Gly Thr Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Arg Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Ala Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
```

325 330 335

Ala Glu Asp Val Asp His Leu Leu Asn Gln Val Arg Leu Ala Ala Asp
340 345 350

Arg Thr Gln Glu Arg
355

<210> SEQ ID NO 57
<211> LENGTH: 1071
<212> TYPE: DNA
<213> ORGANISM: Artificial sequence
<220> FEATURE:
<223> OTHER INFORMATION: Engineered sequence

<400> SEQUENCE: 57
atgaatggtg aaaccagtcg tccgccggca ctgggtttta gcagcgaaaa cattgcaggc 60
gcaagtccgg aagttctgca agcactggtt aaacatagca gcggtcaagc tggtccgtat 120
ggtatggatg atattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcc gtgcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaata tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctgcgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 58
<211> LENGTH: 357
<212> TYPE: PRT
<213> ORGANISM: Artificial sequence
<220> FEATURE:
<223> OTHER INFORMATION: Engineered sequence

<400> SEQUENCE: 58

Met Asn Gly Glu Thr Ser Arg Pro Pro Ala Leu Gly Phe Ser Ser Glu
1 5 10 15

Asn Ile Ala Gly Ala Ser Pro Glu Val Leu Gln Ala Leu Val Lys His
20 25 30

Ser Ser Gly Gln Ala Gly Pro Tyr Gly Met Asp Asp Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

-continued

```
Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Arg Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Ala Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 59
<211> LENGTH: 1071
<212> TYPE: DNA
<213> ORGANISM: Artificial sequence
<220> FEATURE:
<223> OTHER INFORMATION: Engineered sequence

<400> SEQUENCE: 59

```
atgaatggtg aaaccagtcg tccgccggca ctgggtttta gcagcgaaaa cattgcaggc      60

gcaagtccgg aagttctgca agcactggtt aaacatagca gcggtcaagc tggtccgtat     120

ggtatggatg atattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480
```

gacgaaatcc gtgcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggt gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtctggact ctgcgatgat tgacgcactg ctgaaagcgg gctttaaatt tggctataaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 60
<211> LENGTH: 357
<212> TYPE: PRT
<213> ORGANISM: Artificial sequence
<220> FEATURE:
<223> OTHER INFORMATION: Engineered sequence

<400> SEQUENCE: 60

Met Asn Gly Glu Thr Ser Arg Pro Pro Ala Leu Gly Phe Ser Ser Glu
1               5                   10                  15

Asn Ile Ala Gly Ala Ser Pro Glu Val Leu Gln Ala Leu Val Lys His
            20                  25                  30

Ser Ser Gly Gln Ala Gly Pro Tyr Gly Met Asp Asp Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Arg Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

-continued

```
Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 61
<211> LENGTH: 1071
<212> TYPE: DNA
<213> ORGANISM: Artificial sequence
<220> FEATURE:
<223> OTHER INFORMATION: Engineered sequence

<400> SEQUENCE: 61

atgaatggtg aaaccagtcg tccgccggca ctgggtttta gcagcgaaaa cattgcaggc      60

gcaagtccgg aagttctgca agcactggtt aaacatagca gcggtcaagc tggtccgtat     120

ggtatggatg atattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480

gacgaaatcc gtgcgattgg cgacgtctgc aaaagtagta gtctgggcct gcatatggac     540

ggtagtcgtt ttgcgaacgc actggttagt ctgggttgtt ctccggcaga aatgacctgg     600

aaagcaggtg ttgacgcact gagttttggc gcaaccaaaa acggcgttct ggctgcagaa     660

gcaattgttc tgtttaacac cagcctggcc accgaaatga gctatcgtcg taaacgcgca     720

ggtcatctga ttagcaaata tcgtttcctg agcgcacaga ttgacgcata tctgaccgac     780

gatctgtggc tgcgtaacgc acgtaaagca aacgcagcag cacaacgtct ggcacaaggt     840

ctggaaggtc tgggcggcgt tgaagttctg ggcggtaccg aagcaaacat tctgttctgc     900

cgtatggact ctgcgatgat tgacgcactg ctgaaagcgg gctttaaatt tggctataaa     960

cgctggggtc cgaacgttgt tcgttttgtc accagctttg caaccaccgc agaagacgtt    1020

gatcatctgc tgaaccaagt tcgtctggca gcagatcgta cccaagaacg t             1071


<210> SEQ ID NO 62
<211> LENGTH: 357
<212> TYPE: PRT
<213> ORGANISM: Artificial sequence
<220> FEATURE:
<223> OTHER INFORMATION: Engineered sequence

<400> SEQUENCE: 62

Met Asn Gly Glu Thr Ser Arg Pro Pro Ala Leu Gly Phe Ser Ser Glu
1               5                   10                  15
```

```
Asn Ile Ala Gly Ala Ser Pro Glu Val Leu Gln Ala Leu Val Lys His
            20                  25                  30

Ser Ser Gly Gln Ala Gly Pro Tyr Gly Met Asp Asp Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Arg Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Ala Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 63
<211> LENGTH: 1071
<212> TYPE: DNA
<213> ORGANISM: Artificial sequence
<220> FEATURE:
<223> OTHER INFORMATION: Engineered sequence

<400> SEQUENCE: 63

atgaatggtg aaaccagtcg tccgccggca ctgggtttta gcagcgaaaa cattgcaggc      60
```

-continued

```
gcaagtccgg aagttctgca agcactggtt aaacatagca gcggtcaagc tggtccgtat    120
ggtaccgatg atattaccgc gcaggttaaa cgtaaattct gcgagatctt cgagcgcgac    180
gttgaagttt ttctggttcc gaccggtacc gctgctaacg cactgtgtct gtctgcaatg    240
accccgccgt ggggtaatat ttattgccac catgcaagcc atattaataa cgacgagtgc    300
ggcgcaccgg aatttttcag caacggcgcc aaactgatga ccgttgacgg tccggcagca    360
aaactggata ttgtacgtct gcgcgaacgt accagcgaaa aagttggcga cgttcatacc    420
acccaaccgg cttgcgttag tattacccag gcaaccgaag ttggtagcat ctataccctg    480
gacgaaatcg aagcgattgg cgacgtctgc aaaagtagta gtctgggcct gcatatggac    540
ggtagtcgtt ttgcgaacgc actggttagt ctgggttgtt ctccggcaga aatgacctgg    600
aaagcaggtg ttgacgcact gagttttggc gcaaccaaaa acggcgttct ggctgcagaa    660
gcaattgttc tgtttaacac cagcctggcc accgaaatga gctatcgtcg taaacgcgca    720
ggtcatctga ttagcaaaca tcgtttcctg agcgcacaga ttgacgcata tctgaccgac    780
gatctgtggc tgcgtaacgc acgtaaagca aacgcagcag cacaacgtct ggcacaaggt    840
ctggaaggtc tgggcggcgt tgaagttctg ggcggtaccg aagcaaacat tctgttctgc    900
cgtatggact ctgcgatgat tgacgcactg ctgaaagcgg gctttaaatt tggctataaa    960
cgctggggtc cgaacgttgt tcgttttgtc accagctttg caaccaccgc agaagacgtt   1020
gatcatctgc tgaaccaagt tcgtctggca gcagatcgta cccaagaacg t            1071
```

<210> SEQ ID NO 64
<211> LENGTH: 357
<212> TYPE: PRT
<213> ORGANISM: Artificial sequence
<220> FEATURE:
<223> OTHER INFORMATION: Engineered sequence

<400> SEQUENCE: 64

```
Met Asn Gly Glu Thr Ser Arg Pro Pro Ala Leu Gly Phe Ser Ser Glu
1               5                   10                  15

Asn Ile Ala Gly Ala Ser Pro Glu Val Leu Gln Ala Leu Val Lys His
            20                  25                  30

Ser Ser Gly Gln Ala Gly Pro Tyr Gly Thr Asp Asp Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190
```

-continued

```
Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Ala Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 65
<211> LENGTH: 1071
<212> TYPE: DNA
<213> ORGANISM: Artificial sequence
<220> FEATURE:
<223> OTHER INFORMATION: Engineered sequence

<400> SEQUENCE: 65

```
atgaatggtg aaaccagtcg tccgccggca ctgggtttta gcagcgaaaa cattgcaggc     60

gcaagtccgg aagttgcgca agcactggtt aaacatagca gcggtcaagc tggtccgtat    120

ggtaccgatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 66
<211> LENGTH: 357
<212> TYPE: PRT
<213> ORGANISM: Artificial sequence
<220> FEATURE:
<223> OTHER INFORMATION: Engineered sequence

<400> SEQUENCE: 66

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 67
<211> LENGTH: 1071
<212> TYPE: DNA
<213> ORGANISM: Artificial sequence
<220> FEATURE:
<223> OTHER INFORMATION: Engineered sequence

<400> SEQUENCE: 67
atgaatggtg aaaccagtcg tccgccggca ctgggtttta gcagcgaaaa cattgcaggc 60
gcaagtccgg aagttctgca agcactggtt aaacatagca gcggtcaagc tggtccgtat 120
ggtaccgatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcc gtgcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaata tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctgcgatgat tgacgcactg ctgaaagcgg gctttaaatt tggctataaa 960
cgctggggtc cgaacgttgt tcgttttgtc accagctttg caaccaccgc agaagacgtt 1020
gatcatctgc tgaaccaagt tcgtctggca gcatatcgta cccaagaacg t 1071

<210> SEQ ID NO 68
<211> LENGTH: 357
<212> TYPE: PRT
<213> ORGANISM: Artificial sequence
<220> FEATURE:
<223> OTHER INFORMATION: Engineered sequence

<400> SEQUENCE: 68

Met Asn Gly Glu Thr Ser Arg Pro Pro Ala Leu Gly Phe Ser Ser Glu
1 5 10 15

Asn Ile Ala Gly Ala Ser Pro Glu Val Leu Gln Ala Leu Val Lys His
20 25 30

Ser Ser Gly Gln Ala Gly Pro Tyr Gly Thr Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg

-continued

```
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Arg Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Ala Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Tyr
            340                 345                 350

Arg Thr Gln Glu Arg
        355


<210> SEQ ID NO 69
<211> LENGTH: 1071
<212> TYPE: DNA
<213> ORGANISM: Artificial sequence
<220> FEATURE:
<223> OTHER INFORMATION: Engineered sequence

<400> SEQUENCE: 69

atgaatggtg aaaccagtcg tccgccggca ctgggtttta gcagcgaaaa cattgcaggc      60

gcaagtccgg aagttgcgca agcactggtt aaacatagca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480

gacgaaatcc gtgcgattgg cgacgtctgc aaaagtagta gtctgggcct gcatatggac     540

ggtagtcgtt ttgcgaacgc actggttagt ctgggttgtt ctccggcaga aatgacctgg     600

aaagcaggtg ttgacgcact gagttttggc gcaaccaaaa acggcgttct ggctgcagaa     660
```

-continued

```
gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctgcgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

```
<210> SEQ ID NO 70
<211> LENGTH: 357
<212> TYPE: PRT
<213> ORGANISM: Artificial sequence
<220> FEATURE:
<223> OTHER INFORMATION: Engineered sequence

<400> SEQUENCE: 70

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Arg Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
```

-continued 290 295 300

Ala Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 71
<211> LENGTH: 1071
<212> TYPE: DNA
<213> ORGANISM: Artificial sequence
<220> FEATURE:
<223> OTHER INFORMATION: Engineered sequence

<400> SEQUENCE: 71
atgaatggtg aaaccagtcg tccgccggca ctgggtttta gcagcgaaaa cattgcaggc 60
gcaagtccgg aagttctgca agcactggtt aaacatagca gcggtcaagc tggtccgtat 120
ggtaccgatg aaattcatgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 72
<211> LENGTH: 357
<212> TYPE: PRT
<213> ORGANISM: Artificial sequence
<220> FEATURE:
<223> OTHER INFORMATION: Engineered sequence

<400> SEQUENCE: 72

Met Asn Gly Glu Thr Ser Arg Pro Pro Ala Leu Gly Phe Ser Ser Glu
1 5 10 15

Asn Ile Ala Gly Ala Ser Pro Glu Val Leu Gln Ala Leu Val Lys His
20 25 30

Ser Ser Gly Gln Ala Gly Pro Tyr Gly Thr Asp Glu Ile His Ala Gln
35 40 45

```
Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 73
<211> LENGTH: 1071
<212> TYPE: DNA
<213> ORGANISM: Artificial sequence
<220> FEATURE:
<223> OTHER INFORMATION: Engineered sequence

<400> SEQUENCE: 73

```
atgaatggtg aaaccagtcg tccgccggca ctgggtttta gcagcgaaaa cattgcaggc      60

gcaagtccgg aagttctgca agcactggtt aaacatagca gcggtcaagc tggtccgtat     120

ggtaccgatg atattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300
```

```
ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctaggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaata tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t           1071
```

```
<210> SEQ ID NO 74
<211> LENGTH: 357
<212> TYPE: PRT
<213> ORGANISM: Artificial sequence
<220> FEATURE:
<223> OTHER INFORMATION: Engineered sequence

<400> SEQUENCE: 74

Met Asn Gly Glu Thr Ser Arg Pro Pro Ala Leu Gly Phe Ser Ser Glu
1               5                   10                  15

Asn Ile Ala Gly Ala Ser Pro Glu Val Leu Gln Ala Leu Val Lys His
            20                  25                  30

Ser Ser Gly Gln Ala Gly Pro Tyr Gly Thr Asp Asp Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220
```

-continued

```
Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 75
<211> LENGTH: 1071
<212> TYPE: DNA
<213> ORGANISM: Artificial sequence
<220> FEATURE:
<223> OTHER INFORMATION: Engineered sequence

<400> SEQUENCE: 75

```
atgaatggtg aaaccagtcg tccgccggca ctgggtttta gcagcgaaaa cattgcaggc      60

gcaagtccgg aagttctgca agcactggtt aaacatagca gcggtcaagc tggtccgtat     120

ggtaccgatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480

gacgaaatcg aagcgattgg cgacgtctgc aaaagtagta gtctgggcct gcatatggac     540

ggtagtcgtt ttgcgaacgc actggttagt ctgggttgtt ctccggcaga aatgacctgg     600

aaagcaggtg ttgacgcact gagttttggc gcaaccaaaa acggcgttct ggctgcagaa     660

gcaattgttc tgtttaacac cagcctggcc accgaaatga gctatcgtcg taaacgcgca     720

ggtcatctga ttagcaaaca tcgtttcctg agcgcacaga ttgacgcata tctgaccgac     780

gatctgtggc tgcgtaacgc acgtaaagca aacgcagcag cacaacgtct ggcacaaggt     840

ctggaaggtc tgggcggcgt tgaagttctg ggcggtaccg aagcaaacat tctgttctgc     900

cgtatggact ctccgatgat tgacgcactg ctgaaagcgg gctttaaatt tggctatgaa     960

cgctggggtc cgaacgttgt tcgttttgtc accagctttg caaccaccgc agaagacgtt    1020

gatcatctgc tgaaccaagt tcgtctggca gcagatcgta cccaagaacg t             1071
```

<210> SEQ ID NO 76
<211> LENGTH: 357
<212> TYPE: PRT
<213> ORGANISM: Artificial sequence
<220> FEATURE:

<223> OTHER INFORMATION: Engineered sequence

<400> SEQUENCE: 76

```
Met Asn Gly Glu Thr Ser Arg Pro Pro Ala Leu Gly Phe Ser Ser Glu
1               5                   10                  15

Asn Ile Ala Gly Ala Ser Pro Glu Val Leu Gln Ala Leu Val Lys His
            20                  25                  30

Ser Ser Gly Gln Ala Gly Pro Tyr Gly Thr Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 77
<211> LENGTH: 1071
<212> TYPE: DNA
<213> ORGANISM: Artificial sequence
<220> FEATURE:

<223> OTHER INFORMATION: Engineered sequence

<400> SEQUENCE: 77
atgaatggtg aaaccagtcg tccgccggca ctgggtttta gcagcgaaaa cattgcaggc 60
gcaagtccgg aagttgcgca agcactggtt aaacatagca gcggtcaagc tggtccgtat 120
ggtatggatg atattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcc gtgcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttaaatt tggctataaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 78
<211> LENGTH: 357
<212> TYPE: PRT
<213> ORGANISM: Artificial sequence
<220> FEATURE:
<223> OTHER INFORMATION: Engineered sequence

<400> SEQUENCE: 78

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Met Asp Asp Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

```
Asp Glu Ile Arg Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 79
<211> LENGTH: 1071
<212> TYPE: DNA
<213> ORGANISM: Artificial sequence
<220> FEATURE:
<223> OTHER INFORMATION: Engineered sequence

<400> SEQUENCE: 79

```
atgaatggtg aaaccagtcg tccgccggca ctgggtttta gcagcgaaaa cattgcaggc      60

gcaagtccgg aagttgcgca agcactggtt aaacatagca gcggtcaagc tggtccgtat     120

ggtaccgatg atattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480

gacgaaatcc gtgcgattgg cgacgtctgc aaaagtagta gtctgggcct gcatatggac     540

ggttcgcgtt ttgcgaacgc actggttagt ctgggttgtt ctccggcaga aatgacctgg     600

aaagcaggtg ttgacgcact gagttttggc gcaaccaaaa acggcgttct ggctgcagaa     660

gcaattgttc tgtttaacac cagcctggcc accgaaatga gctatcgtcg caaacgcgca     720

ggtcatctga ttagcaaaca tcgtttcctg agcgcacaga ttgacgcata tctgaccgac     780

gatctgtggc tgcgtaacgc acgtaaagca aacgcagcag cacaacgtct ggcacaaggt     840

ctggaaggtc tgggcggcgt tgaagttctg ggcggtaccg aagcaaacat tctgttctgc     900
```

```
cgtatggact ctgcgatgat tgacgcactg ctgaaagcgg gctttaaatt tggctatgag    960

cgctggggtc cgaacgttgt tcgttttgtc accagctttg caaccaccgc agaagacgtt   1020

gatcatctgc tgaaccaagt tcgtctggca gcagatcgta cccaagaacg t            1071


<210> SEQ ID NO 80
<211> LENGTH: 357
<212> TYPE: PRT
<213> ORGANISM: Artificial sequence
<220> FEATURE:
<223> OTHER INFORMATION: Engineered sequence

<400> SEQUENCE: 80

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Asp Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Arg Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Ala Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335
```

Ala Glu Asp Val Asp His Leu Leu Asn Gln Val Arg Leu Ala Ala Asp
340 345 350

Arg Thr Gln Glu Arg
355

<210> SEQ ID NO 81
<211> LENGTH: 1071
<212> TYPE: DNA
<213> ORGANISM: Artificial sequence
<220> FEATURE:
<223> OTHER INFORMATION: Engineered sequence

<400> SEQUENCE: 81
atgaatggtg aaaccagtcg tccgccggca ctgggtttta gcagcgaaaa cattgcaggc 60
gcaagtccgg aagttctgca agcactggtt aaacatagca gcggtcaagc tggtccgtat 120
ggtatggatg atattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcc gtgcgattgg cgacgtctgc aaaagtagta gtctgggcct gcatatggac 540
ggtgcgcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtac gaaacgcgca 720
ggtcatctga ttagcaaata tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctgcgatgat tgacgcactg ctgaaagcgg gctttaaatt tggctataag 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 82
<211> LENGTH: 357
<212> TYPE: PRT
<213> ORGANISM: Artificial sequence
<220> FEATURE:
<223> OTHER INFORMATION: Engineered sequence

<400> SEQUENCE: 82

Met Asn Gly Glu Thr Ser Arg Pro Pro Ala Leu Gly Phe Ser Ser Glu
1 5 10 15

Asn Ile Ala Gly Ala Ser Pro Glu Val Leu Gln Ala Leu Val Lys His
20 25 30

Ser Ser Gly Gln Ala Gly Pro Tyr Gly Met Asp Asp Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn

-continued

```
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Arg Ala Ile Gly Asp Val Cys Lys Ser Ser Ser Leu Gly
                165                 170                 175

Leu His Met Asp Gly Ala Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Thr Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Ala Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 83
<211> LENGTH: 1071
<212> TYPE: DNA
<213> ORGANISM: Artificial sequence
<220> FEATURE:
<223> OTHER INFORMATION: Engineered sequence

<400> SEQUENCE: 83

atgaatggtg aaaccagtcg tccgccggca ctgggtttta gcagcgaaaa cattgcaggc      60

gcaagtccgg aagttctgca agcactggtt aaacatagca gcggtcaagc tggtccgtat     120

ggtaccgatg atattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480
```

-continued

```
gacgaaatcc gtgcgattgg cgacgtctgc aaaagtagta gtctgggcct gcatatggac     540

ggttcgcgtt ttgcgaacgc actggttagt ctgggttgtt ctccggcaga aatgacctgg     600

aaagcaggtg ttgacgcact gagttttggc gcaaccaaaa acggcgttct ggctgcagaa     660

gcaattgttc tgtttaacac cagcctggcc accgaaatga gctatcgtcg caaacgcgca     720

ggtcatctga ttagcaaaca tcgtttcctg agcgcacaga ttgacgcata tctgaccgac     780

gatctgtggc tgcgtaacgc acgtaaagca aacgcagcag cacaacgtct ggcacaaggt     840

ctggaaggtc tgggcggcgt tgaagttctg ggcggtaccg aagcaaacat tctgttctgc     900

cgtatggact ctgcgatgat tgacgcactg ctgaaagcgg gctttaaatt tctctatgag     960

cgctggggtc cgaacgttgt tcgttttgtc accagctttg caaccaccgc agaagacgtt    1020

gatcatctgc tgaaccaagt tcgtctggca gcagatcgta cccaagaacg t             1071
```

<210> SEQ ID NO 84
<211> LENGTH: 357
<212> TYPE: PRT
<213> ORGANISM: Artificial sequence
<220> FEATURE:
<223> OTHER INFORMATION: Engineered sequence

<400> SEQUENCE: 84

```
Met Asn Gly Glu Thr Ser Arg Pro Pro Ala Leu Gly Phe Ser Ser Glu
1               5                   10                  15

Asn Ile Ala Gly Ala Ser Pro Glu Val Leu Gln Ala Leu Val Lys His
            20                  25                  30

Ser Ser Gly Gln Ala Gly Pro Tyr Gly Thr Asp Asp Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Arg Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
```

```
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Ala Met Ile Asp Ala Leu Leu Lys Ala Gly Phe Lys Phe Leu Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 85
<211> LENGTH: 1071
<212> TYPE: DNA
<213> ORGANISM: Artificial sequence
<220> FEATURE:
<223> OTHER INFORMATION: Engineered sequence

<400> SEQUENCE: 85

atgaatggtg aaaccagccg tccgccggca ctgggtttta gcagcgaaaa cattgcaggc      60

gcaagtccgg aagttgcaca agcactggtt aaacatagca gcggtcaagc tccgccgtat     120

ggtaccgatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480

gacgaaatcg aagcgattgg cgacgtctgc aaaagtagta gtctgggcct gcatatggac     540

ggtagtcgtt ttgcgaacgc actggttagt ctgggttgtt ctccggcaga aatgacctgg     600

aaagcaggtg ttgacgcact gagttttggc gcaaccaaaa acggcgttct ggctgcagaa     660

gcaattgttc tgtttaacac cagcctggcc accgaaatga gctatcgtcg taaacgcgca     720

ggtcatctga ttagcaaata ccgtttcctg agcgcacaga ttgacgcata tctgaccgac     780

gatctgtggc tgcgtaacgc acgtaaagca aacgcagcag cacaacgtct ggcacaaggt     840

ctggaaggtc tgggcggcgt tgaagttctg ggcggcaccg aagcaaacat tctgttctgc     900

cgtctggact ctgcaatgat tgacgcactg ctgaaagcgg gctttaaatt tggctataaa     960

cgctggggtc cgaacgttgt tcgttttgtc accagctttg caaccaccgc agaagacgtt    1020

gatcatctgc tgaaccaagt tcgtctggca gcagatcgta cccaagaacg t             1071


<210> SEQ ID NO 86
<211> LENGTH: 357
<212> TYPE: PRT
<213> ORGANISM: Artificial sequence
<220> FEATURE:
<223> OTHER INFORMATION: Engineered sequence

<400> SEQUENCE: 86

Met Asn Gly Glu Thr Ser Arg Pro Pro Ala Leu Gly Phe Ser Ser Glu
1               5                   10                  15
```

-continued

```
Asn Ile Ala Gly Ala Ser Pro Glu Val Ala Gln Ala Leu Val Lys His
            20                  25                  30

Ser Ser Gly Gln Ala Pro Pro Tyr Gly Thr Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 87
<211> LENGTH: 1071
<212> TYPE: DNA
<213> ORGANISM: Artificial sequence
<220> FEATURE:
<223> OTHER INFORMATION: Engineered sequence

<400> SEQUENCE: 87

```
atgaatggtg aaaccagtcg tccgccggca ctgggtttta gcagcgaaaa cattgcaggc      60

gcaagtccgg aagttctgca agcactggtt aaacatagca gcggtcaagc tggtccgtat     120
```

-continued ggtatggatg atattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcc gtgcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 88
<211> LENGTH: 357
<212> TYPE: PRT
<213> ORGANISM: Artificial sequence
<220> FEATURE:
<223> OTHER INFORMATION: Engineered sequence

<400> SEQUENCE: 88

Met Asn Gly Glu Thr Ser Arg Pro Pro Ala Leu Gly Phe Ser Ser Glu
1 5 10 15

Asn Ile Ala Gly Ala Ser Pro Glu Val Leu Gln Ala Leu Val Lys His
20 25 30

Ser Ser Gly Gln Ala Gly Pro Tyr Gly Met Asp Asp Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Arg Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

```
Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 89
<211> LENGTH: 1071
<212> TYPE: DNA
<213> ORGANISM: Artificial sequence
<220> FEATURE:
<223> OTHER INFORMATION: Engineered sequence

<400> SEQUENCE: 89

```
atgaatggtg aaaccagtcg tccgccggca ctgggtttta gcagcgaaaa cattgcaggc     60

gcaagtccgg aagttctgca agcactggtt aaacatagca gcggtcaagc tggtccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcc gtgcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 90
<211> LENGTH: 357
<212> TYPE: PRT
<213> ORGANISM: Artificial sequence
<220> FEATURE:
<223> OTHER INFORMATION: Engineered sequence

<400> SEQUENCE: 90

```
Met Asn Gly Glu Thr Ser Arg Pro Pro Ala Leu Gly Phe Ser Ser Glu
1               5                   10                  15

Asn Ile Ala Gly Ala Ser Pro Glu Val Leu Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Arg Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 91
<211> LENGTH: 1071
<212> TYPE: DNA
<213> ORGANISM: Artificial sequence
<220> FEATURE:
<223> OTHER INFORMATION: Engineered sequence

<400> SEQUENCE: 91
atgaatggtg aaaccagtcg tccgccggca ctgggtttta gcagcgaaaa cattgcaggc 60
gcaagtccgg aagttctgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac cttgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 92
<211> LENGTH: 357
<212> TYPE: PRT
<213> ORGANISM: Artificial sequence
<220> FEATURE:
<223> OTHER INFORMATION: Engineered sequence

<400> SEQUENCE: 92

Met Asn Gly Glu Thr Ser Arg Pro Pro Ala Leu Gly Phe Ser Ser Glu
1               5                   10                  15

Asn Ile Ala Gly Ala Ser Pro Glu Val Leu Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His Leu Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

```
Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 93
<211> LENGTH: 1071
<212> TYPE: DNA
<213> ORGANISM: Artificial sequence
<220> FEATURE:
<223> OTHER INFORMATION: Engineered sequence

<400> SEQUENCE: 93

atgaatggtg aaaccagtcg tccgccggca ctgggtttta gcagcgaaaa cattgcaggc      60

gcaagtccgg aagttgcgca agcactggtt aaacatagca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac aaggcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480

gacgaaatcg aagcgattgg cgacgtctgc aaaagtagta gtctgggcct gcatatggac     540

ggtagtcgtt ttgcgaacgc actggttagt ctgggttgtt ctccggcaga aatgacctgg     600

aaagcaggtg ttgacgcact gagttttggc gcaaccaaaa acggcgttct ggctgcagaa     660

gcaattgttc tgtttaacac cagcctggcc accgaaatga gctatcgtcg taaacgcgca     720
```

ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 94
<211> LENGTH: 357
<212> TYPE: PRT
<213> ORGANISM: Artificial sequence
<220> FEATURE:
<223> OTHER INFORMATION: Engineered sequence

<400> SEQUENCE: 94

Met Asn Gly Glu Thr Ser Arg Pro Pro Ala Leu Gly Phe Ser Ser Glu
1 5 10 15

Asn Ile Ala Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His Lys Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Ala Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Gly Gly Thr Glu Ala Asn Ile Leu Phe Cys Arg Met Asp Ser
290 295 300

```
Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

```
<210> SEQ ID NO 95
<211> LENGTH: 1071
<212> TYPE: DNA
<213> ORGANISM: Artificial sequence
<220> FEATURE:
<223> OTHER INFORMATION: Engineered sequence

<400> SEQUENCE: 95

atgaatggtg aaaccagtcg tccgccggca ctgggtttta gcagcgaaaa catttggggc     60

gcaagtccgg aagttgcgca agcactggtt aaacatagca gcggtcaagc tggtccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

```
<210> SEQ ID NO 96
<211> LENGTH: 357
<212> TYPE: PRT
<213> ORGANISM: Artificial sequence
<220> FEATURE:
<223> OTHER INFORMATION: Engineered sequence

<400> SEQUENCE: 96

Met Asn Gly Glu Thr Ser Arg Pro Pro Ala Leu Gly Phe Ser Ser Glu
1               5                   10                  15

Asn Ile Trp Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
```

```
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 97
<211> LENGTH: 1071
<212> TYPE: DNA
<213> ORGANISM: Artificial sequence
<220> FEATURE:
<223> OTHER INFORMATION: Engineered sequence

<400> SEQUENCE: 97

```
atgaatggtg aaaccagtcg tccgccggca ctgggtttta gcagcgaaaa cattaatggc      60

gcaagtccgg aagttgcgca agcactggtt aaacatagca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300
```

-continued

```
ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 98
<211> LENGTH: 357
<212> TYPE: PRT
<213> ORGANISM: Artificial sequence
<220> FEATURE:
<223> OTHER INFORMATION: Engineered sequence

<400> SEQUENCE: 98

```
Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
```

-continued

```
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 99
<211> LENGTH: 1071
<212> TYPE: DNA
<213> ORGANISM: Artificial sequence
<220> FEATURE:
<223> OTHER INFORMATION: Engineered sequence

<400> SEQUENCE: 99

atgaatggtg aaaccagtcg tccgccggca ctgggtttta gcagcgaaaa cattgcaggc     60

gcaagtccgg aagttgcgca agcactggtt aaagttagca gcggtcaagc tggtccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071


<210> SEQ ID NO 100
<211> LENGTH: 357
<212> TYPE: PRT
<213> ORGANISM: Artificial sequence
<220> FEATURE:
<223> OTHER INFORMATION: Engineered sequence
```

<400> SEQUENCE: 100

Met Asn Gly Glu Thr Ser Arg Pro Pro Ala Leu Gly Phe Ser Ser Glu
1 5 10 15

Asn Ile Ala Gly Ala Ser Pro Glu Val Ala Gln Ala Leu Val Lys Val
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Ala Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Gly Gly Thr Glu Ala Asn Ile Leu Phe Cys Arg Met Asp Ser
290 295 300

Pro Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 101
<211> LENGTH: 1071
<212> TYPE: DNA
<213> ORGANISM: Artificial sequence
<220> FEATURE:
<223> OTHER INFORMATION: Engineered sequence

<400> SEQUENCE: 101

```
atgaatggtg aaaccagtcg tccgccggca ctgggtttta gcagcgaaaa cattgcaggc     60
gcaagtccgg aagttgcgca agcactggtt aaacataata gcggtcaagc tggtccgtat    120
ggtatggatg aaattaccgc gcaggttaaa cgtaaattct gcgagatctt cgagcgcgac    180
gttgaagttt ttctggttcc gaccggtacc gctgctaacg cactgtgtct gtctgcaatg    240
accccgccgt ggggtaatat ttattgccac catgcaagcc atattaataa cgacgagtgc    300
ggcgcaccgg aatttttcag caacggcgcc aaactgatga ccgttgacgg tccggcagca    360
aaactggata ttgtacgtct gcgcgaacgt accagcgaaa aagttggcga cgttcatacc    420
acccaaccgg cttgcgttag tattacccag gcaaccgaag ttggtagcat ctataccctg    480
gacgaaatcg aagcgattgg cgacgtctgc aaaagtagta gtctgggcct gcatatggac    540
ggtagtcgtt ttgcgaacgc actggttagt ctgggttgtt ctccggcaga aatgacctgg    600
aaagcaggtg ttgacgcact gagttttggc gcaaccaaaa acggcgttct ggctgcagaa    660
gcaattgttc tgtttaacac cagcctggcc accgaaatga gctatcgtcg taaacgcgca    720
ggtcatctga ttagcaaaca tcgtttcctg agcgcacaga ttgacgcata tctgaccgac    780
gatctgtggc tgcgtaacgc acgtaaagca aacgcagcag cacaacgtct ggcacaaggt    840
ctggaaggtc tgggcggcgt tgaagttctg ggcggtaccg aagcaaacat tctgttctgc    900
cgtatggact ctccgatgat tgacgcactg ctgaaagcgg gctttaaatt tggctatgaa    960
cgctggggtc cgaacgttgt tcgttttgtc accagctttg caaccaccgc agaagacgtt   1020
gatcatctgc tgaaccaagt tcgtctggca gcagatcgta cccaagaacg t            1071
```

<210> SEQ ID NO 102
<211> LENGTH: 357
<212> TYPE: PRT
<213> ORGANISM: Artificial sequence
<220> FEATURE:
<223> OTHER INFORMATION: Engineered sequence

<400> SEQUENCE: 102

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Asn Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160
```

```
Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 103
<211> LENGTH: 1071
<212> TYPE: DNA
<213> ORGANISM: Artificial sequence
<220> FEATURE:
<223> OTHER INFORMATION: Engineered sequence

<400> SEQUENCE: 103

```
atgaatggtg aaaccagtcg tccgccggca ctgggtttta gcagcgaaaa cattgcaggc      60

gcaagtccgg aagttgcgca agcactggtt aaacatagca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tcgggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480

gacgaaatcg aagcgattgg cgacgtctgc aaaagtagta gtctgggcct gcatatggac     540

ggtagtcgtt ttgcgaacgc actggttagt ctgggttgtt ctccggcaga aatgacctgg     600

aaagcaggtg ttgacgcact gagttttggc gcaaccaaaa acggcgttct ggctgcagaa     660

gcaattgttc tgtttaacac cagcctggcc accgaaatga gctatcgtcg taaacgcgca     720

ggtcatctga ttagcaaaca tcgtttcctg agcgcacaga ttgacgcata tctgaccgac     780

gatctgtggc tgcgtaacgc acgtaaagca aacgcagcag cacaacgtct ggcacaaggt     840

ctggaaggtc tgggcggcgt tgaagttctg ggcggtaccg aagcaaacat tctgttctgc     900
```

```
cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071


<210> SEQ ID NO 104
<211> LENGTH: 357
<212> TYPE: PRT
<213> ORGANISM: Artificial sequence
<220> FEATURE:
<223> OTHER INFORMATION: Engineered sequence

<400> SEQUENCE: 104

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Arg Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335
```

Ala Glu Asp Val Asp His Leu Leu Asn Gln Val Arg Leu Ala Ala Asp
340 345 350

Arg Thr Gln Glu Arg
355

<210> SEQ ID NO 105
<211> LENGTH: 1071
<212> TYPE: DNA
<213> ORGANISM: Artificial sequence
<220> FEATURE:
<223> OTHER INFORMATION: Engineered sequence

<400> SEQUENCE: 105
atgaatggtg aaaccagtcg tccgccggca ctgggtttta gcagcgaaaa cattgcaggc 60
gcaagtccgg aagttgcgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag gtggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 106
<211> LENGTH: 357
<212> TYPE: PRT
<213> ORGANISM: Artificial sequence
<220> FEATURE:
<223> OTHER INFORMATION: Engineered sequence

<400> SEQUENCE: 106

Met Asn Gly Glu Thr Ser Arg Pro Pro Ala Leu Gly Phe Ser Ser Glu
1 5 10 15

Asn Ile Ala Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Gly Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Ala Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Gly Gly Thr Glu Ala Asn Ile Leu Phe Cys Arg Met Asp Ser
290 295 300

Pro Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 107
<211> LENGTH: 1071
<212> TYPE: DNA
<213> ORGANISM: Artificial sequence
<220> FEATURE:
<223> OTHER INFORMATION: Engineered sequence

<400> SEQUENCE: 107
atgaatggtg aaaccagtcg tccgccggca ctgggtttta gcagcgaaaa cattgcaggc 60
gcaagtccgg aagttgcgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540

```
ggtagtcgtt ttgcgaacgc actggttagt ctgggttgtt ctccggcaga aatgacctgg    600

aaagcaggtg ttgacgcact gagttttggc gcaaccaaaa acggcgttct gtgtgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 108
<211> LENGTH: 357
<212> TYPE: PRT
<213> ORGANISM: Artificial sequence
<220> FEATURE:
<223> OTHER INFORMATION: Engineered sequence

<400> SEQUENCE: 108

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Cys Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270
```

Ala Ala Gln Arg Leu Ala Gln Gly Leu Glu Gly Leu Gly Gly Val Glu
275 280 285

Val Leu Gly Gly Thr Glu Ala Asn Ile Leu Phe Cys Arg Met Asp Ser
290 295 300

Pro Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 109
<211> LENGTH: 1071
<212> TYPE: DNA
<213> ORGANISM: Artificial sequence
<220> FEATURE:
<223> OTHER INFORMATION: Engineered sequence

<400> SEQUENCE: 109
atgaatggtg aaaccagtcg tccgccggca ctgggtttta gcagcgaaaa cattgcaggc 60
gcaagtccgg aagttgcgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgtttg ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 110
<211> LENGTH: 357
<212> TYPE: PRT
<213> ORGANISM: Artificial sequence
<220> FEATURE:
<223> OTHER INFORMATION: Engineered sequence

<400> SEQUENCE: 110

Met Asn Gly Glu Thr Ser Arg Pro Pro Ala Leu Gly Phe Ser Ser Glu
1 5 10 15

Asn Ile Ala Gly Ala Ser Pro Glu Val Ala Gln Ala Leu Val Lys His

```
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Trp Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 111
<211> LENGTH: 1071
<212> TYPE: DNA
<213> ORGANISM: Artificial sequence
<220> FEATURE:
<223> OTHER INFORMATION: Engineered sequence

<400> SEQUENCE: 111

```
atgaatggtg aaaccagtcg tccgccggca ctgggtttta gcagcgaaaa cattgcaggc      60

gcaagtccgg aagttgcgca agcactggtt aaacatagca gcggtcaagc tggtccgtat     120
```

```
ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggctgtct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

```
<210> SEQ ID NO 112
<211> LENGTH: 357
<212> TYPE: PRT
<213> ORGANISM: Artificial sequence
<220> FEATURE:
<223> OTHER INFORMATION: Engineered sequence

<400> SEQUENCE: 112

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
```

```
        195                 200                 205

Phe Gly Ala Thr Lys Asn Gly Cys Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 113
<211> LENGTH: 1071
<212> TYPE: DNA
<213> ORGANISM: Artificial sequence
<220> FEATURE:
<223> OTHER INFORMATION: Engineered sequence

<400> SEQUENCE: 113

atgaatggtg aaaccagtcg tccgccggca ctgggtttta gcagcgaaaa cattgcaggc     60

gcaagtccgg aagttgcgca agcactggtt aaacatagca gcggtcaagc tggtccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcaagaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

-continued

<210> SEQ ID NO 114
<211> LENGTH: 357
<212> TYPE: PRT
<213> ORGANISM: Artificial sequence
<220> FEATURE:
<223> OTHER INFORMATION: Engineered sequence

<400> SEQUENCE: 114

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Lys Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 115
<211> LENGTH: 1071
<212> TYPE: DNA
<213> ORGANISM: Artificial sequence
<220> FEATURE:
<223> OTHER INFORMATION: Engineered sequence

<400> SEQUENCE: 115
atgaatggtg aaaccagtcg tccgccggca ctgggtttta gcagcgaaaa cattgcaggc 60
gcaagtccgg aagttgcgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtacca tggcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 116
<211> LENGTH: 357
<212> TYPE: PRT
<213> ORGANISM: Artificial sequence
<220> FEATURE:
<223> OTHER INFORMATION: Engineered sequence

<400> SEQUENCE: 116

Met Asn Gly Glu Thr Ser Arg Pro Pro Ala Leu Gly Phe Ser Ser Glu
1 5 10 15

Asn Ile Ala Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

-continued

```
Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Met Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 117
<211> LENGTH: 1071
<212> TYPE: DNA
<213> ORGANISM: Artificial sequence
<220> FEATURE:
<223> OTHER INFORMATION: Engineered sequence

<400> SEQUENCE: 117

```
atgaatggtg aaaccagtcg tccgccggca ctgggtttta gcagcgaaaa cattgcaggc      60

gcaagtccgg aagttgcgca agcactggtt aaacatagca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480

gacgaaatcg aagcgattgg cgacgtctgc aaaagtagta gtctgggcct gcatatggac     540

ggtagtcgtt ttgcgaacgc actggttagt ctgggttgtt ctccggcaga aatgacctgg     600

aaagcaggtg ttgacgcact gagttttggc gcaaccaaaa acggcgttct ggctgcagaa     660

gcaattgttc tgtttaacac cagcctggcc accgaaatga gctatcgtcg taaacgcgca     720
```

ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg tttggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 118
<211> LENGTH: 357
<212> TYPE: PRT
<213> ORGANISM: Artificial sequence
<220> FEATURE:
<223> OTHER INFORMATION: Engineered sequence

<400> SEQUENCE: 118

Met Asn Gly Glu Thr Ser Arg Pro Pro Ala Leu Gly Phe Ser Ser Glu
1 5 10 15

Asn Ile Ala Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Ala Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Phe Gly Thr Glu Ala Asn Ile Leu Phe Cys Arg Met Asp Ser
290 295 300

```
Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 119
<211> LENGTH: 1071
<212> TYPE: DNA
<213> ORGANISM: Artificial sequence
<220> FEATURE:
<223> OTHER INFORMATION: Engineered sequence

<400> SEQUENCE: 119

atgaatggtg aaaccagtcg tccgccggca ctgggtttta gcagcgaaaa cattgcaggc     60

gcaagtccgg aagttgcgca agcactggtt aaacatagca gcggtcaagc tggtccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg gtgggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071


<210> SEQ ID NO 120
<211> LENGTH: 357
<212> TYPE: PRT
<213> ORGANISM: Artificial sequence
<220> FEATURE:
<223> OTHER INFORMATION: Engineered sequence

<400> SEQUENCE: 120

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60
```

```
Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Val Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 121
<211> LENGTH: 1071
<212> TYPE: DNA
<213> ORGANISM: Artificial sequence
<220> FEATURE:
<223> OTHER INFORMATION: Engineered sequence

<400> SEQUENCE: 121

```
atgaatggtg aaaccagtcg tccgccggca ctgggtttta gcagcgaaaa cattgcaggc      60

gcaagtccgg aagttgcgca agcactggtt aaacatagca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360
```

```
aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt catggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 122
<211> LENGTH: 357
<212> TYPE: PRT
<213> ORGANISM: Artificial sequence
<220> FEATURE:
<223> OTHER INFORMATION: Engineered sequence

<400> SEQUENCE: 122

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser His Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240
```

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Gly Gly Thr Glu Ala Asn Ile Leu Phe Cys Arg Met Asp Ser
290 295 300

Pro Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 123
<211> LENGTH: 1071
<212> TYPE: DNA
<213> ORGANISM: Artificial sequence
<220> FEATURE:
<223> OTHER INFORMATION: Engineered sequence

<400> SEQUENCE: 123
atgaatggtg aaaccagtcg tccgccggca ctgggtttta gcagcgaaaa cattgcaggc 60
gcaagtccgg aagttgcgca agcactggtt aaacatagca gcggtcaagc ttctccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 124
<211> LENGTH: 357
<212> TYPE: PRT
<213> ORGANISM: Artificial sequence
<220> FEATURE:
<223> OTHER INFORMATION: Engineered sequence -continued

<400> SEQUENCE: 124

Met Asn Gly Glu Thr Ser Arg Pro Pro Ala Leu Gly Phe Ser Ser Glu
1 5 10 15

Asn Ile Ala Gly Ala Ser Pro Glu Val Ala Gln Ala Leu Val Lys His
20 25 30

Ser Ser Gly Gln Ala Ser Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Ala Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Gly Gly Thr Glu Ala Asn Ile Leu Phe Cys Arg Met Asp Ser
290 295 300

Pro Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 125
<211> LENGTH: 1071
<212> TYPE: DNA
<213> ORGANISM: Artificial sequence
<220> FEATURE:
<223> OTHER INFORMATION: Engineered sequence

<400> SEQUENCE: 125

```
atgaatggtg aaaccagtcg tccgccggca ctgggtttta gcagcgaaaa cattgcaggc     60
gcaagtccgg aagttgcgca agcactggtt aaacatagca gcggtcaagc tggtccgtat    120
ggtatggatg aaattaccgc gcaggttaaa cgtaaattct gcgagatctt cgagcgcgac    180
gttgaagttt ttctggttcc gaccggtacc gctgctaacg cactgtgtct gtctgcaatg    240
accccgccgt ggggtaatat ttattgccac catgcaagcc atattaataa cgacgagtgc    300
ggcgcaccgg aatttttcag caacggcgcc aaactgatga ccgttgacgg tccggcagca    360
aaactggata ttgtacgtct gcgcgaacgt accagcgaaa aagttggcga cgttcatacc    420
acccaaccgg cttgcgttag tattacccag gcaaccgaag ttggtagcat ctataccctg    480
gacgaaatcg aagcgattgg cgacgtctgc aaaagtagta gtctgggcct gcatatggac    540
ggtagtcgtt ttgcgaacgc actggttagt ctgggttgtt ctccggcaga aatgacctgg    600
aaagcaggtg ttgacgcact gagttttggc gcaaccaaaa acggcgttct ggctgcagaa    660
gcaattgttc tgtttaacac cagcctggcc accgaaatga gctatcgtcg taaacgcgca    720
ggtcatctga ttagcaaaca tcgtttcctg agcgcacaga ttgacgcata tctgaccgac    780
gatctgtggc tgcgtaacgc acgtaaagca aacgcagcag cacaacgtct ggcacaaggt    840
ctggaaggtc tgggcggcgt tattgttctg ggcggtaccg aagcaaacat tctgttctgc    900
cgtatggact ctccgatgat tgacgcactg ctgaaagcgg gctttaaatt tggctatgaa    960
cgctggggtc cgaacgttgt tcgttttgtc accagctttg caaccaccgc agaagacgtt   1020
gatcatctgc tgaaccaagt tcgtctggca gcagatcgta cccaagaacg t            1071
```

<210> SEQ ID NO 126
<211> LENGTH: 357
<212> TYPE: PRT
<213> ORGANISM: Artificial sequence
<220> FEATURE:
<223> OTHER INFORMATION: Engineered sequence

<400> SEQUENCE: 126

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
```

-continued

```
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Ile
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 127
<211> LENGTH: 1071
<212> TYPE: DNA
<213> ORGANISM: Artificial sequence
<220> FEATURE:
<223> OTHER INFORMATION: Engineered sequence

<400> SEQUENCE: 127

```
atgaatggtg aaaccagtcg tccgccggca ctgggtttta gcagcgaaaa cattgcaggc     60

gcaagtccgg aagttgcgca agcactggtt aaacatagca gcggtcaagc tggtccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960
```

cgctggggtc cgaacgttgt tcgttttgtc accagctttg caaccaccgc agaagacgtt 1020
gatcatctgc tgaaccaagt tcgtctggca gcacagcgta cccaagaacg t 1071

<210> SEQ ID NO 128
<211> LENGTH: 357
<212> TYPE: PRT
<213> ORGANISM: Artificial sequence
<220> FEATURE:
<223> OTHER INFORMATION: Engineered sequence

<400> SEQUENCE: 128

Met Asn Gly Glu Thr Ser Arg Pro Pro Ala Leu Gly Phe Ser Ser Glu
1 5 10 15

Asn Ile Ala Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Ala Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Gly Gly Thr Glu Ala Asn Ile Leu Phe Cys Arg Met Asp Ser
290 295 300

Pro Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Gln 340 345 350

Arg Thr Gln Glu Arg
355

<210> SEQ ID NO 129
<211> LENGTH: 1071
<212> TYPE: DNA
<213> ORGANISM: Artificial sequence
<220> FEATURE:
<223> OTHER INFORMATION: Engineered sequence

<400> SEQUENCE: 129
atgaatggtg aaaccagtcg tccgccggca ctgggtttta gcagcgaaaa cattgcaggc 60
gcaagtccgg aagttgcgca agcactggtt aaacatagca gcggtcaagc tgagccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 130
<211> LENGTH: 357
<212> TYPE: PRT
<213> ORGANISM: Artificial sequence
<220> FEATURE:
<223> OTHER INFORMATION: Engineered sequence

<400> SEQUENCE: 130

Met Asn Gly Glu Thr Ser Arg Pro Pro Ala Leu Gly Phe Ser Ser Glu
1 5 10 15

Asn Ile Ala Gly Ala Ser Pro Glu Val Ala Gln Ala Leu Val Lys His
20 25 30

Ser Ser Gly Gln Ala Glu Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

-continued

```
Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 131
<211> LENGTH: 1071
<212> TYPE: DNA
<213> ORGANISM: Artificial sequence
<220> FEATURE:
<223> OTHER INFORMATION: Engineered sequence

<400> SEQUENCE: 131

```
atgaatggtg aaaccagtcg tccgccggca ctgggtttta gcagcgaaaa cattgcaggc      60

gcaagtccgg aagttgcgca agcactggtt aaacatagca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480

gacgaaatcg aagcgattgg cgacgtctgc aaaagtagta gtctgggcct gcatatggac     540
```

-continued

```
ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgagtggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 132
<211> LENGTH: 357
<212> TYPE: PRT
<213> ORGANISM: Artificial sequence
<220> FEATURE:
<223> OTHER INFORMATION: Engineered sequence

<400> SEQUENCE: 132

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270
```

Ala Ala Gln Arg Leu Ala Gln Gly Leu Glu Gly Leu Ser Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355

<210> SEQ ID NO 133
<211> LENGTH: 1071
<212> TYPE: DNA
<213> ORGANISM: Artificial sequence
<220> FEATURE:
<223> OTHER INFORMATION: Engineered sequence

<400> SEQUENCE: 133
atgaatggtg aaaccagtcg tccgccggca ctgggtttta gcagcgaaaa cattgcaggc 60
gcaagtccgg aagttgcgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgaagggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 134
<211> LENGTH: 357
<212> TYPE: PRT
<213> ORGANISM: Artificial sequence
<220> FEATURE:
<223> OTHER INFORMATION: Engineered sequence

<400> SEQUENCE: 134

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

```
Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Lys Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 135
<211> LENGTH: 1071
<212> TYPE: DNA
<213> ORGANISM: Artificial sequence
<220> FEATURE:
<223> OTHER INFORMATION: Engineered sequence

<400> SEQUENCE: 135

```
atgaatggtg aaaccagtcg tccgccggca ctgggtttta gcagcgaaaa cattgcaggc      60

gcaagtccgg aagttgcgca agcactggtt aaacatagca gcggtcaagc tggtccgtat     120

ggtatggatg aaattaccgc gcaggttaaa cgtaaattct gcgagatctt cgagcgcgac     180
```

-continued gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggta agggcggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 136
<211> LENGTH: 357
<212> TYPE: PRT
<213> ORGANISM: Artificial sequence
<220> FEATURE:
<223> OTHER INFORMATION: Engineered sequence

<400> SEQUENCE: 136

Met Asn Gly Glu Thr Ser Arg Pro Pro Ala Leu Gly Phe Ser Ser Glu
1 5 10 15

Asn Ile Ala Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

```
Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Lys Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 137
<211> LENGTH: 1071
<212> TYPE: DNA
<213> ORGANISM: Artificial sequence
<220> FEATURE:
<223> OTHER INFORMATION: Engineered sequence

<400> SEQUENCE: 137

atgaatggtg aaaccagtcg tccgccggca ctgggtttta gcagcgaaaa cattgcaggc     60

gcaagtccgg aagttgcgca agcactggtt aaacatagca gcggtcaagc tggtccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtt ttggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071


<210> SEQ ID NO 138
```

<211> LENGTH: 357
<212> TYPE: PRT
<213> ORGANISM: Artificial sequence
<220> FEATURE:
<223> OTHER INFORMATION: Engineered sequence

<400> SEQUENCE: 138

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Phe Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 139

<211> LENGTH: 1071
<212> TYPE: DNA
<213> ORGANISM: Artificial sequence
<220> FEATURE:
<223> OTHER INFORMATION: Engineered sequence

<400> SEQUENCE: 139
atgaatggtg aaaccagtcg tccgccggca ctgggtttta gcagcgaaaa cattgcaggc 60
gcaagtccgg aagttgcgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctgcggggtc tgggcggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 140
<211> LENGTH: 357
<212> TYPE: PRT
<213> ORGANISM: Artificial sequence
<220> FEATURE:
<223> OTHER INFORMATION: Engineered sequence

<400> SEQUENCE: 140

Met Asn Gly Glu Thr Ser Arg Pro Pro Ala Leu Gly Phe Ser Ser Glu
1 5 10 15

Asn Ile Ala Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala

```
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Arg Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 141
<211> LENGTH: 1071
<212> TYPE: DNA
<213> ORGANISM: Artificial sequence
<220> FEATURE:
<223> OTHER INFORMATION: Engineered sequence

<400> SEQUENCE: 141

atgaatggtg aaaccagtcg tccgccggca ctgggtttta gcagcgaaaa cattgcaggc     60

gcaagtccgg aagttgcgca agcactggtt aaacatagca gcggtcaagc tggtccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actgagtagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780
```

```
gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071


<210> SEQ ID NO 142
<211> LENGTH: 357
<212> TYPE: PRT
<213> ORGANISM: Artificial sequence
<220> FEATURE:
<223> OTHER INFORMATION: Engineered sequence

<400> SEQUENCE: 142

Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Ser Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
```

305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 143
<211> LENGTH: 1071
<212> TYPE: DNA
<213> ORGANISM: Artificial sequence
<220> FEATURE:
<223> OTHER INFORMATION: Engineered sequence

<400> SEQUENCE: 143
atgaatggtg aaaccagtcg tccgccggca ctgggtttta gcagcgaaaa cattgcaggc 60
gcaagtccgg aagttgcgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagggaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 144
<211> LENGTH: 357
<212> TYPE: PRT
<213> ORGANISM: Artificial sequence
<220> FEATURE:
<223> OTHER INFORMATION: Engineered sequence

<400> SEQUENCE: 144

Met Asn Gly Glu Thr Ser Arg Pro Pro Ala Leu Gly Phe Ser Ser Glu
1 5 10 15

Asn Ile Ala Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

-continued

```
Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Gly Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 145
<211> LENGTH: 1071
<212> TYPE: DNA
<213> ORGANISM: Artificial sequence
<220> FEATURE:
<223> OTHER INFORMATION: Engineered sequence

<400> SEQUENCE: 145

atgaatggtg aaaccagtcg tccgccggca ctgggtttta gcagcgaaaa cattgcaggc      60

gcaagtccgg aagttgcgca agcactggtt aaacatagca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360
```

```
aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttgtgtt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 146
<211> LENGTH: 357
<212> TYPE: PRT
<213> ORGANISM: Artificial sequence
<220> FEATURE:
<223> OTHER INFORMATION: Engineered sequence

<400> SEQUENCE: 146

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240
```

```
Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Val Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 147
<211> LENGTH: 1071
<212> TYPE: DNA
<213> ORGANISM: Artificial sequence
<220> FEATURE:
<223> OTHER INFORMATION: Engineered sequence

<400> SEQUENCE: 147

```
atgaatggtg aaaccagtcg tccgccggca ctgggtttta gcagcgaaaa cattgcaggc     60

gcaagtccgg aagttgcgca agcactggtt aaacatagca gcggtcaagc tggtccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc tgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 148
<211> LENGTH: 357
<212> TYPE: PRT
<213> ORGANISM: Artificial sequence
<220> FEATURE:
<223> OTHER INFORMATION: Engineered sequence

<400> SEQUENCE: 148

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Leu Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 149
<211> LENGTH: 1071
<212> TYPE: DNA
<213> ORGANISM: Artificial sequence
<220> FEATURE:
<223> OTHER INFORMATION: Engineered sequence

<400> SEQUENCE: 149

```
atgaacggtg aaacctcgcg tccgccggcg ctgggtttta gctctgaaaa tattgctggt     60

gcaagcccgg aagtcgcaca ggcactcgtt aagcacagtt cgggccaggc gggtccctat    120

ggtaccgatg aaattactgc tcaagttaaa cgtaaatttt gcgaaatctt cgaacgcgac    180

gtcgaagtgt tcctggttcc gaccggtacg gcagcaaacg cactgtgtct gtccgcaatg    240

accccgccgt ggggtaatat ttactgccat cacgcgtccc acatcaacaa tgatgaatgt    300

ggtgcgccgg aatttttctc aaacggcgcc aaactgatga ccgttgatgg tccggcagct    360

aaactggaca ttgtccgtct gcgcgaacgt acgtccgaaa aagtgggtga tgttcatacg    420

acgcagccgg catgcgtctc tattacccaa gctacggaag tgggcagtat ctataccctg    480

gatgaaattg aagccatcgg tgacgtgtgc aaatcatcga gcctgggtct gcacatggat    540

ggctctcgtt ttactaatgc gctggtgtcc ctgggctgtt caccggcaga aatgacctgg    600

aaagccggtg ttgacgcact gagttttggt gcgacgaaaa acggcgttct ggcggccgaa    660

gcaattgtcc tgttcaatac ctcgctggct acggaaatga gctatcgtcg caaacgtgcc    720

ggccacctga tcagtaaata ccgctttctg agcgctcaga tcgatgcgta cctgaccgat    780

gacctgtggc tgcgtaacgc ccgcaaagca aatgcagctg cgcagcgtct ggcccaaggt    840

ctggaaggcc tgggcggtgt tgaagtcctg ggcggtaccg aagcaaacat tctgttctgt    900

cgcctggatt ctgccatgat cgacgcactg ctgaaagctg gctttaaatt cgggtacaag    960

cgttggggtc cgaacgtggt tcgctttgtt accagcttcg ctaccacggc ggaagatgtg   1020

gaccacctgc tgaatcaggt tcgcctggcc gcagaccgta cgcaagaacg c            1071
```

<210> SEQ ID NO 150
<211> LENGTH: 357
<212> TYPE: PRT
<213> ORGANISM: Artificial sequence
<220> FEATURE:
<223> OTHER INFORMATION: Engineered sequence

<400> SEQUENCE: 150

```
Met Asn Gly Glu Thr Ser Arg Pro Pro Ala Leu Gly Phe Ser Ser Glu
1               5                   10                  15

Asn Ile Ala Gly Ala Ser Pro Glu Val Ala Gln Ala Leu Val Lys His
            20                  25                  30

Ser Ser Gly Gln Ala Gly Pro Tyr Gly Thr Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175
```

-continued

```
Leu His Met Asp Gly Ser Arg Phe Thr Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys Tyr Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Leu Asp Ser
    290                 295                 300

Ala Met Ile Asp Ala Leu Leu Lys Ala Gly Phe Lys Phe Gly Tyr Lys
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 151
<211> LENGTH: 1071
<212> TYPE: DNA
<213> ORGANISM: Artificial sequence
<220> FEATURE:
<223> OTHER INFORMATION: Engineered sequence

<400> SEQUENCE: 151

```
atgaatggtg aaaccagtcg tccgccggca ctgggtttta gcagcgaaaa cattaatggc     60

gcaagtccgg aagttgcgca agcactggtt aaacatagca gcggtcaagc tggtccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaaa gcggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg tggggtaccg aagcaaacat tctgttctgc    900

cgtatggact ctccgatgat tgacgcactg ctgaaagcgg gctttaaatt tggctatgaa    960
```

cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 152
<211> LENGTH: 357
<212> TYPE: PRT
<213> ORGANISM: Artificial sequence
<220> FEATURE:
<223> OTHER INFORMATION: Engineered sequence

<400> SEQUENCE: 152

Met Asn Gly Glu Thr Ser Arg Pro Pro Ala Leu Gly Phe Ser Ser Glu
1 5 10 15

Asn Ile Asn Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Ser Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Ala Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Trp Gly Thr Glu Ala Asn Ile Leu Phe Cys Arg Met Asp Ser
290 295 300

Pro Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 153
<211> LENGTH: 1071
<212> TYPE: DNA
<213> ORGANISM: Artificial sequence
<220> FEATURE:
<223> OTHER INFORMATION: Engineered sequence

<400> SEQUENCE: 153
atgaatggtg aaaccagtcg tccgccggca ctgggtttta gcagcgaaaa cattaatggc 60
gcaagtccgg aagttgcgca agcactggtt aaacataaca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaat cgggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggctgctg ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 154
<211> LENGTH: 357
<212> TYPE: PRT
<213> ORGANISM: Artificial sequence
<220> FEATURE:
<223> OTHER INFORMATION: Engineered sequence

<400> SEQUENCE: 154

Met Asn Gly Glu Thr Ser Arg Pro Pro Ala Leu Gly Phe Ser Ser Glu
1 5 10 15

Asn Ile Asn Gly Ala Ser Pro Glu Val Ala Gln Ala Leu Val Lys His
20 25 30

Asn Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu

```
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Ser Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Cys Trp Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 155
<211> LENGTH: 1071
<212> TYPE: DNA
<213> ORGANISM: Artificial sequence
<220> FEATURE:
<223> OTHER INFORMATION: Engineered sequence

<400> SEQUENCE: 155

```
atgaatggtg aaaccagtcg tccgccggca ctgggtttta gcagcgaaaa cattaatggc      60

gcaagtccgg aagttgcgca agcactggtt aaacataaca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac ctggcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag cgggtagcat ctataccctg     480

gacgaaatcg aagcgattgg cgacgtctgc aaaagtagta gtctgggcct gcatatggac     540

ggtagtcgtt ttgcgaacgc actggttagt ctgggttgtt ctccggcaga aatgacctgg     600
```

```
aaagcaggtg ttgacgcact gagttttggc gcaaccaaaa acggctgctg ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 156
<211> LENGTH: 357
<212> TYPE: PRT
<213> ORGANISM: Artificial sequence
<220> FEATURE:
<223> OTHER INFORMATION: Engineered sequence

<400> SEQUENCE: 156

```
Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys His
            20                  25                  30

Asn Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His Leu Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Ala Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Cys Trp Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
```

```
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 157
<211> LENGTH: 1071
<212> TYPE: DNA
<213> ORGANISM: Artificial sequence
<220> FEATURE:
<223> OTHER INFORMATION: Engineered sequence

<400> SEQUENCE: 157

```
atgaatggtg aaaccagtcg tccgccggca ctgggtttta gcagcgaaaa cattaatggc     60

gcaagtccgg aagttgcgca agcactggtt aaacataaca gcggtcaagc tggtccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaat cgggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct gtgcgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 158
<211> LENGTH: 357
<212> TYPE: PRT
<213> ORGANISM: Artificial sequence
<220> FEATURE:
<223> OTHER INFORMATION: Engineered sequence

<400> SEQUENCE: 158

```
Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys His
            20                  25                  30
```

Asn Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Ser Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Cys Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Gly Gly Thr Glu Ala Asn Ile Leu Phe Cys Arg Met Asp Ser
290 295 300

Pro Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 159
<211> LENGTH: 1071
<212> TYPE: DNA
<213> ORGANISM: Artificial sequence
<220> FEATURE:
<223> OTHER INFORMATION: Engineered sequence

<400> SEQUENCE: 159
atgaatggtg aaaccagtcg tccgccggca ctgggtttta gcagcgaaaa cattaatggc 60
gcaagtccgg aagttgcgca agcactggtt aaagtgaaca gcggtcaagc tggtccgtat 120
ggtatggatg aaattaccgc gcaggttaaa cgtaaattct gcgagatctt cgagcgcgac 180

-continued

```
gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaat cgggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgtttg gtgcgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 160
<211> LENGTH: 357
<212> TYPE: PRT
<213> ORGANISM: Artificial sequence
<220> FEATURE:
<223> OTHER INFORMATION: Engineered sequence

<400> SEQUENCE: 160

```
Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys Val
            20                  25                  30

Asn Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Ser Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205
```

```
Phe Gly Ala Thr Lys Asn Gly Val Trp Cys Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 161
<211> LENGTH: 1071
<212> TYPE: DNA
<213> ORGANISM: Artificial sequence
<220> FEATURE:
<223> OTHER INFORMATION: Engineered sequence

<400> SEQUENCE: 161

```
atgaatggtg aaaccagtcg tccgccggca ctgggtttta gcagcgaaaa cattaatggc      60

gcaagtccgg aagttgcgca agcactggtt aaagtgaaca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaat cgggtagcat ctataccctg     480

gacgaaatcg aagcgattgg cgacgtctgc aaaagtagta gtctgggcct gcatatggac     540

ggtagtcgtt ttgcgaacgc actggttagt ctgggttgtt ctccggcaga aatgacctgg     600

aaagcaggtg ttgacgcact gagttttggc gcaaccaaaa acggctgctg ggctgcagaa     660

gcaattgttc tgtttaacac cagcctggcc accgaaatga gctatcgtcg taaacgcgca     720

ggtcatctga ttagcaaaca tcgtttcctg agcgcacaga ttgacgcata tctgaccgac     780

gatctgtggc tgcgtaacgc acgtaaagca aacgcagcag cacaacgtct ggcacaaggt     840

ctggaaggtc tgggcggcgt tgaagttctg ggcggtaccg aagcaaacat tctgttctgc     900

cgtatggact ctccgatgat tgacgcactg ctgaaagcgg gctttaaatt tggctatgaa     960

cgctggggtc cgaacgttgt tcgttttgtc accagctttg caaccaccgc agaagacgtt    1020

gatcatctgc tgaaccaagt tcgtctggca gcagatcgta cccaagaacg t             1071
```

<210> SEQ ID NO 162
<211> LENGTH: 357

<212> TYPE: PRT
<213> ORGANISM: Artificial sequence
<220> FEATURE:
<223> OTHER INFORMATION: Engineered sequence

<400> SEQUENCE: 162

```
Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys Val
            20                  25                  30

Asn Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Ser Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Cys Trp Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 163
<211> LENGTH: 1071

<212> TYPE: DNA
<213> ORGANISM: Artificial sequence
<220> FEATURE:
<223> OTHER INFORMATION: Engineered sequence

<400> SEQUENCE: 163
atgaatggtg aaaccagtcg tccgccggca ctgggtttta gcagcgaaaa cattaatggc 60
gcaagtccgg aagttctgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag tgggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggctgcct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 164
<211> LENGTH: 357
<212> TYPE: PRT
<213> ORGANISM: Artificial sequence
<220> FEATURE:
<223> OTHER INFORMATION: Engineered sequence

<400> SEQUENCE: 164

Met Asn Gly Glu Thr Ser Arg Pro Pro Ala Leu Gly Phe Ser Ser Glu
1 5 10 15

Asn Ile Asn Gly Ala Ser Pro Glu Val Leu Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

```
Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Cys Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 165
<211> LENGTH: 1071
<212> TYPE: DNA
<213> ORGANISM: Artificial sequence
<220> FEATURE:
<223> OTHER INFORMATION: Engineered sequence

<400> SEQUENCE: 165

```
atgaatggtg aaaccagtcg tccgccggca ctgggtttta gcagcgaaaa cattaatggc      60

gcaagtccgg aagttgcgca agcactggtt aaagtgaaca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag cgggtagcat ctataccctg     480

gacgaaatcg aagcgattgg cgacgtctgc aaaagtagta gtctgggcct gcatatggac     540

ggtagtcgtt ttgcgaacgc actggttagt ctgggttgtt ctccggcaga aatgacctgg     600

aaagcaggtg ttgacgcact gagttttggc gcaaccaaaa acggcgttct ggctgcagaa     660

gcaattgttc tgtttaacac cagcctggcc accgaaatga gctatcgtcg taaacgcgca     720

ggtcatctga ttagcaaaca tcgtttcctg agcgcacaga ttgacgcata tctgaccgac     780
```

```
gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071


<210> SEQ ID NO 166
<211> LENGTH: 357
<212> TYPE: PRT
<213> ORGANISM: Artificial sequence
<220> FEATURE:
<223> OTHER INFORMATION: Engineered sequence

<400> SEQUENCE: 166

Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys Val
            20                  25                  30

Asn Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Ala Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320
```

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 167
<211> LENGTH: 1071
<212> TYPE: DNA
<213> ORGANISM: Artificial sequence
<220> FEATURE:
<223> OTHER INFORMATION: Engineered sequence

<400> SEQUENCE: 167
atgaatggtg aaaccagtcg tccgccggca ctgggtttta gcagcgaaaa cattaatggc 60
gcaagtccgg aagttctgca agcactggtt aaagtgaaca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac ctggcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaat cgggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggctgctg ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 168
<211> LENGTH: 357
<212> TYPE: PRT
<213> ORGANISM: Artificial sequence
<220> FEATURE:
<223> OTHER INFORMATION: Engineered sequence

<400> SEQUENCE: 168

Met Asn Gly Glu Thr Ser Arg Pro Pro Ala Leu Gly Phe Ser Ser Glu
1 5 10 15

Asn Ile Asn Gly Ala Ser Pro Glu Val Leu Gln Ala Leu Val Lys Val
20 25 30

Asn Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met

```
65                  70                  75                  80

Thr Pro Pro Trp Gly Asn Ile Tyr Cys His Leu Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Ser Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Cys Trp Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 169
<211> LENGTH: 1071
<212> TYPE: DNA
<213> ORGANISM: Artificial sequence
<220> FEATURE:
<223> OTHER INFORMATION: Engineered sequence

<400> SEQUENCE: 169

```
atgaatggtg aaaccagtcg tccgccggca ctgggtttta gcagcgaaaa cattaatggc     60

gcaagtccgg aagttgcgca agcactggtt aaacataaca gcggtcaagc tgagccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420
```

```
acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctctggc tgcgtaacgc acgtaaagca aacgcagcag cacaacgtct ggcacaaggt    840

ctggaaggtc tgggcggcgt tgaagttctg tggggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

```
<210> SEQ ID NO 170
<211> LENGTH: 357
<212> TYPE: PRT
<213> ORGANISM: Artificial sequence
<220> FEATURE:
<223> OTHER INFORMATION: Engineered sequence

<400> SEQUENCE: 170

Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys His
            20                  25                  30

Asn Ser Gly Gln Ala Glu Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
```

```
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Trp Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 171
<211> LENGTH: 1071
<212> TYPE: DNA
<213> ORGANISM: Artificial sequence
<220> FEATURE:
<223> OTHER INFORMATION: Engineered sequence

<400> SEQUENCE: 171

```
atgaatggtg aaaccagtcg tccgccggca ctgggtttta gcagcgaaaa cattaatggc      60

gcaagtccgg aagttgcgca agcactggtt aaagtgagca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480

gacgaaatcg aagcgattgg cgacgtctgc aaaagtagta gtctgggcct gcatatggac     540

ggtagtcgtt ttgcgaacgc actggttagt ctgggttgtt ctccggcaga aatgacctgg     600

aaagcaggtg ttgacgcact gagttttggc gcaaccaaaa acggcgttct ggctgcagaa     660

gcaattgttc tgtttaacac cagcctggcc accgaaatga gctatcgtcg taaacgcgca     720

ggtcatctga ttagcaaaca tcgtttcctg agcgcacaga ttgacgcata tctgaccgac     780

gatctctggc tgcgtaacgc acgtaaagca aacgcagcag cacaacgtct ggcacaaggt     840

ctggaaggtc tgggcggcgt tgaagttctg tggggtaccg aagcaaacat tctgttctgc     900

cgtatggact ctccgatgat tgacgcactg ctgaaagcgg gctttaaatt tggctatgaa     960

cgctggggtc cgaacgttgt tcgttttgtc accagctttg caaccaccgc agaagacgtt    1020

gatcatctgc tgaaccaagt tcgtctggca gcagatcgta cccaagaacg t             1071
```

<210> SEQ ID NO 172
<211> LENGTH: 357
<212> TYPE: PRT
<213> ORGANISM: Artificial sequence
<220> FEATURE:
<223> OTHER INFORMATION: Engineered sequence

<400> SEQUENCE: 172

Met Asn Gly Glu Thr Ser Arg Pro Pro Ala Leu Gly Phe Ser Ser Glu
1 5 10 15

Asn Ile Asn Gly Ala Ser Pro Glu Val Ala Gln Ala Leu Val Lys Val
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Ala Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Trp Gly Thr Glu Ala Asn Ile Leu Phe Cys Arg Met Asp Ser
290 295 300

Pro Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 173
<211> LENGTH: 1071
<212> TYPE: DNA
<213> ORGANISM: Artificial sequence
<220> FEATURE:
<223> OTHER INFORMATION: Engineered sequence

<400> SEQUENCE: 173

```
atgaatggtg aaaccagtcg tccgccggca ctgggtttta gcagcgaaaa cattaatggc     60

gcaagtccgg aagttgcgca agcactggtt aaacatagca gcggtcaagc tggtccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaat cgggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggctgctg ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 174
<211> LENGTH: 357
<212> TYPE: PRT
<213> ORGANISM: Artificial sequence
<220> FEATURE:
<223> OTHER INFORMATION: Engineered sequence

<400> SEQUENCE: 174

```
Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Ser Gly Ser Ile Tyr Thr Leu
145                 150                 155                 160

Asp Glu Ile Glu Ala Ile Gly Asp Val Cys Lys Ser Ser Ser Leu Gly
                165                 170                 175
```

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Cys Trp Ala Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Gly Gly Thr Glu Ala Asn Ile Leu Phe Cys Arg Met Asp Ser
290 295 300

Pro Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 175
<211> LENGTH: 1071
<212> TYPE: DNA
<213> ORGANISM: Artificial sequence
<220> FEATURE:
<223> OTHER INFORMATION: Engineered sequence

<400> SEQUENCE: 175
atgaatggtg aaaccagtcg tccgccggca ctgggtttta gcagcgaaaa cattaatggc 60
gcaagtccgg aagttgcgca agcactggtt aaagtgagca gcggtcaagc tgcgccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctctggc tgcgtaacgc acgtaaagca aacgcagcag cacaacgtct ggcacaaggt 840
ctggaaggtc tgggcggcgt tgaagttctg tacggtacca tggcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 176
<211> LENGTH: 357
<212> TYPE: PRT
<213> ORGANISM: Artificial sequence
<220> FEATURE:
<223> OTHER INFORMATION: Engineered sequence

<400> SEQUENCE: 176

Met Asn Gly Glu Thr Ser Arg Pro Pro Ala Leu Gly Phe Ser Ser Glu
1 5 10 15

Asn Ile Asn Gly Ala Ser Pro Glu Val Ala Gln Ala Leu Val Lys Val
20 25 30

Ser Ser Gly Gln Ala Ala Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Ala Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Tyr Gly Thr Met Ala Asn Ile Leu Phe Cys Arg Met Asp Ser
290 295 300

Pro Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 177
<211> LENGTH: 1071
<212> TYPE: DNA
<213> ORGANISM: Artificial sequence
<220> FEATURE:
<223> OTHER INFORMATION: Engineered sequence

<400> SEQUENCE: 177
atgaatggtg aaaccagtcg tccgccggca ctgggtttta gcagcgaaaa cattaatggc 60
gcaagtccgg aagttgcgca agcactggtt aaagtgagca gcggtcaagc tgagccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatatctggc tgcgtaacgc acgtaaagca aacgcagcag cacaacgtct ggcacaaggt 840
ctggaaggtc tgggcggcgt tgaagttctg tacggtacca tggcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 178
<211> LENGTH: 357
<212> TYPE: PRT
<213> ORGANISM: Artificial sequence
<220> FEATURE:
<223> OTHER INFORMATION: Engineered sequence

<400> SEQUENCE: 178

Met Asn Gly Glu Thr Ser Arg Pro Pro Ala Leu Gly Phe Ser Ser Glu
1 5 10 15

Asn Ile Asn Gly Ala Ser Pro Glu Val Ala Gln Ala Leu Val Lys Val
20 25 30

Ser Ser Gly Gln Ala Glu Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

-continued

```
Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Ile Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Tyr Gly Thr Met Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 179
<211> LENGTH: 1071
<212> TYPE: DNA
<213> ORGANISM: Artificial sequence
<220> FEATURE:
<223> OTHER INFORMATION: Engineered sequence

<400> SEQUENCE: 179

```
atgaatggtg aaaccagtcg tccgccggca ctgggtttta gcagcgaaaa cattaatggc     60

gcaagtccgg aagttgcgca agcactggtt aaacataaca gcggtcaagc tagcccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600
```

-continued aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctctggc tgcgtaacgc acgtaaagca aacgcagcag cacaacgtct ggcacaaggt 840
ctggaaggtc tgggcggcgt tgaagttctg tacggtacca tggcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 180
<211> LENGTH: 357
<212> TYPE: PRT
<213> ORGANISM: Artificial sequence
<220> FEATURE:
<223> OTHER INFORMATION: Engineered sequence

<400> SEQUENCE: 180

Met Asn Gly Glu Thr Ser Arg Pro Pro Ala Leu Gly Phe Ser Ser Glu
1 5 10 15

Asn Ile Asn Gly Ala Ser Pro Glu Val Ala Gln Ala Leu Val Lys His
20 25 30

Asn Ser Gly Gln Ala Ser Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Ala Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Tyr Gly Thr Met Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355

<210> SEQ ID NO 181
<211> LENGTH: 1071
<212> TYPE: DNA
<213> ORGANISM: Artificial sequence
<220> FEATURE:
<223> OTHER INFORMATION: Engineered sequence

<400> SEQUENCE: 181
atgaatggtg aaaccagtcg tccgccggca ctgggtttta gcagcgaaaa cattaatggc 60
gcaagtccgg aagttgcgca agcactggtt aaacataaca gcggtcaagc tgcgccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctctggc tgcgtaacgc acgtaaagca aacgcagcag cacaacgtct ggcacaaggt 840
ctggaaggtc tgggcggcgt tgaagttctg ggcggtacca tggcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 182
<211> LENGTH: 357
<212> TYPE: PRT
<213> ORGANISM: Artificial sequence
<220> FEATURE:
<223> OTHER INFORMATION: Engineered sequence

<400> SEQUENCE: 182

Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys His
            20                  25                  30

Asn Ser Gly Gln Ala Ala Pro Tyr Gly Met Asp Glu Ile Thr Ala Gln

```
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Met Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 183
<211> LENGTH: 1071
<212> TYPE: DNA
<213> ORGANISM: Artificial sequence
<220> FEATURE:
<223> OTHER INFORMATION: Engineered sequence

<400> SEQUENCE: 183

atgaatggtg aaaccagtcg tccgccggca ctgggtttta gcagcgaaaa cattaatggc      60

gcaagtccgg aagttgcgca agcactggtt aaagtgagca gcggtcaagc tagcccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240
```

```
accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatatctggc tgcgtaacgc acgtaaagca aacgcagcag cacaacgtct ggcacaaggt    840

ctggaaggtc tgggcggcgt tgaagttctg tgggtaccga agcaaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

```
<210> SEQ ID NO 184
<211> LENGTH: 357
<212> TYPE: PRT
<213> ORGANISM: Artificial sequence
<220> FEATURE:
<223> OTHER INFORMATION: Engineered sequence

<400> SEQUENCE: 184

Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys Val
            20                  25                  30

Ser Ser Gly Gln Ala Ser Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
```

```
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Ile Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Trp Val Pro Lys Gln Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 185
<211> LENGTH: 1071
<212> TYPE: DNA
<213> ORGANISM: Artificial sequence
<220> FEATURE:
<223> OTHER INFORMATION: Engineered sequence

<400> SEQUENCE: 185

```
atgaatggtg aaaccagtcg tccgccggca ctgggtttta gcagcgaaaa cattaatggc     60

gcaagtccgg aagttgcgca agcactggtt aaacatagca gcggtcaaac ggctgcttat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 186
<211> LENGTH: 357
<212> TYPE: PRT

<213> ORGANISM: Artificial sequence
<220> FEATURE:
<223> OTHER INFORMATION: Engineered sequence

<400> SEQUENCE: 186

```
Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys His
            20                  25                  30

Ser Ser Gly Gln Thr Ala Ala Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 187
<211> LENGTH: 1071
<212> TYPE: DNA

<213> ORGANISM: Artificial sequence
<220> FEATURE:
<223> OTHER INFORMATION: Engineered sequence

<400> SEQUENCE: 187
atgaatggtg aaaccagtcg tccgccggca ctgggtttta gcagcgaaaa cattaatggc 60
gcaagtccgg aagttgcgca agcactggtt aaacatagca gcggtcaaat gcctgcttat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 188
<211> LENGTH: 357
<212> TYPE: PRT
<213> ORGANISM: Artificial sequence
<220> FEATURE:
<223> OTHER INFORMATION: Engineered sequence

<400> SEQUENCE: 188

Met Asn Gly Glu Thr Ser Arg Pro Pro Ala Leu Gly Phe Ser Ser Glu
1 5 10 15

Asn Ile Asn Gly Ala Ser Pro Glu Val Ala Gln Ala Leu Val Lys His
20 25 30

Ser Ser Gly Gln Met Pro Ala Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

-continued

```
Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 189
<211> LENGTH: 1071
<212> TYPE: DNA
<213> ORGANISM: Artificial sequence
<220> FEATURE:
<223> OTHER INFORMATION: Engineered sequence

<400> SEQUENCE: 189

```
atgaatggtg aaaccagtcg tccgccggca ctgggtttta gcagcgaaaa cattaatggc     60

gcaagtccgg aagttgcgca agcactggtt aaacatagca gcggtcaaaa ggctgcttat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840
```

```
ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 190
<211> LENGTH: 357
<212> TYPE: PRT
<213> ORGANISM: Artificial sequence
<220> FEATURE:
<223> OTHER INFORMATION: Engineered sequence

<400> SEQUENCE: 190

```
Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys His
            20                  25                  30

Ser Ser Gly Gln Lys Ala Ala Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320
```

```
Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 191
<211> LENGTH: 1071
<212> TYPE: DNA
<213> ORGANISM: Artificial sequence
<220> FEATURE:
<223> OTHER INFORMATION: Engineered sequence

<400> SEQUENCE: 191

```
atgaatggtg aaaccagtcg tccgccggca ctgggtttta gcagcgaaaa cattaatggc     60

gcaagtccgg aagttgcgca agcactggtt aaacatagca gcggtcaagc tagcccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct gtccgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctctggc tgcgtaacgc acgtaaagca aacgcagcag cacaacgtct ggcacaaggt    840

ctggaaggtc tgggcggcgt taccgttctg tggggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 192
<211> LENGTH: 357
<212> TYPE: PRT
<213> ORGANISM: Artificial sequence
<220> FEATURE:
<223> OTHER INFORMATION: Engineered sequence

<400> SEQUENCE: 192

```
Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys His
            20                  25                  30

Ser Ser Gly Gln Ala Ser Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80
```

```
Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ser Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Thr
        275                 280                 285

Val Leu Trp Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 193
<211> LENGTH: 1071
<212> TYPE: DNA
<213> ORGANISM: Artificial sequence
<220> FEATURE:
<223> OTHER INFORMATION: Engineered sequence

<400> SEQUENCE: 193

```
atgaatggtg aaaccagtcg tccgccggca ctgggtttta gcagcgaaaa cattaatggc      60

gcaagtccgg aagttgcgca agcactggtt aaacatagca gcggtcaagc tagcccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420
```

-continued acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct gtgcgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatatctggc tgcgtaacgc acgtaaagca aacgcagcag cacaacgtct ggcacaaggt 840
ctggaaggtc tgggcggcgt tgaagttctg tggaaaaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 194
<211> LENGTH: 357
<212> TYPE: PRT
<213> ORGANISM: Artificial sequence
<220> FEATURE:
<223> OTHER INFORMATION: Engineered sequence

<400> SEQUENCE: 194

Met Asn Gly Glu Thr Ser Arg Pro Pro Ala Leu Gly Phe Ser Ser Glu
1 5 10 15

Asn Ile Asn Gly Ala Ser Pro Glu Val Ala Gln Ala Leu Val Lys His
20 25 30

Ser Ser Gly Gln Ala Ser Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Cys Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Ile Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Trp Lys Thr Glu Ala Asn Ile Leu Phe Cys Arg Met Asp Ser
290 295 300

Pro Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 195
<211> LENGTH: 1071
<212> TYPE: DNA
<213> ORGANISM: Artificial sequence
<220> FEATURE:
<223> OTHER INFORMATION: Engineered sequence

<400> SEQUENCE: 195
atgaatggtg aaaccagtcg tccgccggca ctgggtttta gcagcgaaaa cattaatggc 60
gcaagtccgg aagttgcgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaat tcggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga tcagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttcgttt tggctatgaa 960
cgctggggtc cgaacgttgt tcgttttgtc accagctttg caaccaccgc agaagacgtt 1020
gatcatctgc tgaaccaagt tcgtctggca gcacagcgta cccaagaacg t 1071

<210> SEQ ID NO 196
<211> LENGTH: 357
<212> TYPE: PRT
<213> ORGANISM: Artificial sequence
<220> FEATURE:
<223> OTHER INFORMATION: Engineered sequence

<400> SEQUENCE: 196

Met Asn Gly Glu Thr Ser Arg Pro Pro Ala Leu Gly Phe Ser Ser Glu

-continued

```
1               5                   10                  15

Asn Ile Asn Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Phe Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Arg Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Gln
            340                 345                 350

Arg Thr Gln Glu Arg
        355
```

<210> SEQ ID NO 197
<211> LENGTH: 1071
<212> TYPE: DNA
<213> ORGANISM: Artificial sequence
<220> FEATURE:
<223> OTHER INFORMATION: Engineered sequence

<400> SEQUENCE: 197
atgaatggtg aaaccagtcg tccgccggca ctgggtttta gcagcgaaaa cattaatggc     60

-continued

```
gcaagtccgg aagttgcgca agcactggtt aaacatagca gcggtcaagc tggtccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaac gtggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatgc gctatcgtcg taaacgcgca    720

ggtcatctgg tcagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttgtgtt tggctatgaa    960

cgctggggtc cgaacgttgt tcgttttgtc accagctttg caaccaccgc agaagacgtt   1020

gatcatctgc tgaaccaagt tcgtctggca gcagcccgta cccaagaacg t            1071
```

<210> SEQ ID NO 198
<211> LENGTH: 357
<212> TYPE: PRT
<213> ORGANISM: Artificial sequence
<220> FEATURE:
<223> OTHER INFORMATION: Engineered sequence

<400> SEQUENCE: 198

```
Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Arg Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
```

```
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Arg Tyr Arg Arg Lys Arg Ala
225                 230                 235                 240

Gly His Leu Val Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Val Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Ala
            340                 345                 350

Arg Thr Gln Glu Arg
        355
```

<210> SEQ ID NO 199
<211> LENGTH: 1071
<212> TYPE: DNA
<213> ORGANISM: Artificial sequence
<220> FEATURE:
<223> OTHER INFORMATION: Engineered sequence

<400> SEQUENCE: 199

```
atgaatggtg aaaccagtcg tccgccggca ctgggtttta gcagcgaaaa cattaatggc     60

gcaagtccgg aagttgcgca agcactggtt aaacatagca gcggtcaagc tggtccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ccggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatgc gctatcgtcg taaacgcgca    720

ggtcatctgg tcagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttgtgtt tggctatgaa    960

cgctggggtc cgaacgttgt tcgttttgtc accagctttg caaccaccgc agaagacgtt   1020
```

-continued gatcatctgc tgaaccaagt tcgtctggca gcacagcgta cccaagaacg t 1071

<210> SEQ ID NO 200
<211> LENGTH: 357
<212> TYPE: PRT
<213> ORGANISM: Artificial sequence
<220> FEATURE:
<223> OTHER INFORMATION: Engineered sequence

<400> SEQUENCE: 200

Met Asn Gly Glu Thr Ser Arg Pro Pro Ala Leu Gly Phe Ser Ser Glu
1 5 10 15

Asn Ile Asn Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Ala Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Ala Ala Glu Ala Ile Val Leu
210 215 220

Phe Asn Thr Ser Leu Ala Thr Glu Met Arg Tyr Arg Arg Lys Arg Ala
225 230 235 240

Gly His Leu Val Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Glu Gly Leu Gly Gly Val Glu
275 280 285

Val Leu Gly Gly Thr Glu Ala Asn Ile Leu Phe Cys Arg Met Asp Ser
290 295 300

Pro Met Ile Asp Ala Leu Leu Lys Ala Gly Phe Val Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Gln
340 345 350

Arg Thr Gln Glu Arg

355

<210> SEQ ID NO 201
<211> LENGTH: 1071
<212> TYPE: DNA
<213> ORGANISM: Artificial sequence
<220> FEATURE:
<223> OTHER INFORMATION: Engineered sequence

<400> SEQUENCE: 201
atgaatggtg aaaccagtcg tccgccggca ctgggtttta gcagcgaaaa cattaatggc 60
gcaagtccgg aagttgcgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac catgcaagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaac gtggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatgc gctatcgtcg taaacgcgca 720
ggtcatctga tcagcaaaca tcgtttcctg agcgcacaga ttgacgcata tctgaccgac 780
gatctgtggc tgcgtaacgc acgtaaagca aacgcagcag cacaacgtct ggcacaaggt 840
ctggaaggtc tgggcggcgt tgaagttctg ggcggtaccg aagcaaacat tctgttctgc 900
cgtatggact ctccgatgat tgacgcactg ctgaaagcgg gctttgtgtt tggctatgaa 960
cgctggggtc cgaacgttgt tcgttttgtc accagctttg caaccaccgc agaagacgtt 1020
gatcatctgc tgaaccaagt tcgtctggca gcacagcgta cccaagaacg t 1071

<210> SEQ ID NO 202
<211> LENGTH: 357
<212> TYPE: PRT
<213> ORGANISM: Artificial sequence
<220> FEATURE:
<223> OTHER INFORMATION: Engineered sequence

<400> SEQUENCE: 202

Met Asn Gly Glu Thr Ser Arg Pro Pro Ala Leu Gly Phe Ser Ser Glu
1 5 10 15

Asn Ile Asn Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Ala Ser His Ile Asn
85 90 95

Asn Asp Glu Cys Gly Ala Pro Glu Phe Phe Ser Asn Gly Ala Lys Leu
100 105 110

-continued

```
Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Arg Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Arg Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Val Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Gln
            340                 345                 350

Arg Thr Gln Glu Arg
        355
```

<210> SEQ ID NO 203
<211> LENGTH: 1071
<212> TYPE: DNA
<213> ORGANISM: Artificial sequence
<220> FEATURE:
<223> OTHER INFORMATION: Engineered sequence

<400> SEQUENCE: 203

```
atgaatggtg aaaccagtcg tccgccggca ctgggtttta gcagcgaaaa cattaatggc     60

gcaagtccgg aagttgcgca agcactggtt aaagtgagca gcggtcaagc tgagccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660
```

```
gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatatctggc tgcgtaacgc acgtaaagca aacgcagcag cacaacgtct ggcacaaggt    840

ctggaaggtc tgggcggcgt tgaagttctg ggcggtacca tggcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 204
<211> LENGTH: 357
<212> TYPE: PRT
<213> ORGANISM: Artificial sequence
<220> FEATURE:
<223> OTHER INFORMATION: Engineered sequence

<400> SEQUENCE: 204

```
Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys Val
            20                  25                  30

Ser Ser Gly Gln Ala Glu Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Ile Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285
```

```
Val Leu Gly Gly Thr Met Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 205
<211> LENGTH: 1071
<212> TYPE: DNA
<213> ORGANISM: Artificial sequence
<220> FEATURE:
<223> OTHER INFORMATION: Engineered sequence

<400> SEQUENCE: 205

atgaatggtg aaaccagtcg tccgccggca ctgggtttta gcagcgaaaa cattaatggc     60

gcaagtccgg aagttgcgca agcactggtt aaagtgagca gcggtcaagc tagcgcgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatatctggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071


<210> SEQ ID NO 206
<211> LENGTH: 357
<212> TYPE: PRT
<213> ORGANISM: Artificial sequence
<220> FEATURE:
<223> OTHER INFORMATION: Engineered sequence

<400> SEQUENCE: 206

Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys Val
            20                  25                  30

Ser Ser Gly Gln Ala Ser Ala Tyr Gly Met Asp Glu Ile Thr Ala Gln
        35                  40                  45
```

```
Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Ile Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 207
<211> LENGTH: 1071
<212> TYPE: DNA
<213> ORGANISM: Artificial sequence
<220> FEATURE:
<223> OTHER INFORMATION: Engineered sequence

<400> SEQUENCE: 207

```
atgaatggtg aaaccagtcg tccgccggca ctgggtttta gcagcgaaaa cattaatggc      60

gcaagtccgg aagttgcgca agcactggtt aaacatagca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240
```

```
accccgccgt ggggtaatat ttattgccac cactggagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctgcgtggtg cgaaaggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 208
<211> LENGTH: 357
<212> TYPE: PRT
<213> ORGANISM: Artificial sequence
<220> FEATURE:
<223> OTHER INFORMATION: Engineered sequence

<400> SEQUENCE: 208

```
Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Trp Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220
```

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Arg Gly Ala Lys Gly Val Glu
275 280 285

Val Leu Gly Gly Thr Glu Ala Asn Ile Leu Phe Cys Arg Met Asp Ser
290 295 300

Pro Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 209
<211> LENGTH: 1071
<212> TYPE: DNA
<213> ORGANISM: Artificial sequence
<220> FEATURE:
<223> OTHER INFORMATION: Engineered sequence

<400> SEQUENCE: 209
atgaatggtg aaaccagtcg tccgccggca ctgggtttta gcagcgaaaa cattaatggc 60
gcaagtccgg aagttgcgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac aactggagcc atattaataa cgacgagtgc 300
ggcgcaccgg aatttttcag caacggcgcc aaactgatga ccgttgacgg tattgcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctgtatggtg cgaaaggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 210
<211> LENGTH: 357
<212> TYPE: PRT
<213> ORGANISM: Artificial sequence
<220> FEATURE:
<223> OTHER INFORMATION: Engineered sequence

<400> SEQUENCE: 210

Met Asn Gly Glu Thr Ser Arg Pro Pro Ala Leu Gly Phe Ser Ser Glu
1 5 10 15

Asn Ile Asn Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His Asn Trp Ser His Ile Asn
85 90 95

Asn Asp Glu Cys Gly Ala Pro Glu Phe Phe Ser Asn Gly Ala Lys Leu
100 105 110

Met Thr Val Asp Gly Ile Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Ala Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Tyr Gly Ala Lys Gly Val Glu
275 280 285

Val Leu Gly Gly Thr Glu Ala Asn Ile Leu Phe Cys Arg Met Asp Ser
290 295 300

Pro Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 211
<211> LENGTH: 1071
<212> TYPE: DNA
<213> ORGANISM: Artificial sequence
<220> FEATURE:
<223> OTHER INFORMATION: Engineered sequence

<400> SEQUENCE: 211
atgaatggtg aaaccagtcg tccgccggca ctgggtttta gcagcgaaaa cattaatggc 60
gcaagtccgg aagttgcgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac aacgcgagcc atattaataa cgacgagtgc 300
ggcgcaccgg aatttttcag caacggcgcc aaactgatga ccgttgacgg tattgcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctgaagggtg cgccgggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 212
<211> LENGTH: 357
<212> TYPE: PRT
<213> ORGANISM: Artificial sequence
<220> FEATURE:
<223> OTHER INFORMATION: Engineered sequence

<400> SEQUENCE: 212

Met Asn Gly Glu Thr Ser Arg Pro Pro Ala Leu Gly Phe Ser Ser Glu
1 5 10 15

Asn Ile Asn Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His Asn Ala Ser His Ile Asn
85 90 95

Asn Asp Glu Cys Gly Ala Pro Glu Phe Phe Ser Asn Gly Ala Lys Leu
100 105 110

Met Thr Val Asp Gly Ile Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu 145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Ala Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Lys Gly Ala Pro Gly Val Glu
275 280 285

Val Leu Gly Gly Thr Glu Ala Asn Ile Leu Phe Cys Arg Met Asp Ser
290 295 300

Pro Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr
325 330 335

Ala Glu Asp Val Asp His Leu Leu Asn Gln Val Arg Leu Ala Ala Asp
340 345 350

Arg Thr Gln Glu Arg
355

<210> SEQ ID NO 213
<211> LENGTH: 1071
<212> TYPE: DNA
<213> ORGANISM: Artificial sequence
<220> FEATURE:
<223> OTHER INFORMATION: Engineered sequence

<400> SEQUENCE: 213
atgaatggtg aaaccagtcg tccgccggca ctgggtttta gcagcgaaaa cattaatggc 60
gcaagtccgg aagttgcgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac aacgcgagcc atattaataa cgacgagtgc 300
ggcgcaccgg aatttttcag caacggcgcc aaactgatga ccgttgacgg tcgcgcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctgtatggtg cgccgggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 214
<211> LENGTH: 357
<212> TYPE: PRT
<213> ORGANISM: Artificial sequence
<220> FEATURE:
<223> OTHER INFORMATION: Engineered sequence

<400> SEQUENCE: 214

Met Asn Gly Glu Thr Ser Arg Pro Pro Ala Leu Gly Phe Ser Ser Glu
1 5 10 15

Asn Ile Asn Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His Asn Ala Ser His Ile Asn
85 90 95

Asn Asp Glu Cys Gly Ala Pro Glu Phe Phe Ser Asn Gly Ala Lys Leu
100 105 110

Met Thr Val Asp Gly Arg Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

Cys Ser Pro Ala Glu Met Thr Trp Lys Ala Gly Val Asp Ala Leu Ser
195 200 205

Phe Gly Ala Thr Lys Asn Gly Val Leu Ala Ala Glu Ala Ile Val Leu
210 215 220

Phe Asn Thr Ser Leu Ala Thr Glu Met Ser Tyr Arg Arg Lys Arg Ala
225 230 235 240

Gly His Leu Ile Ser Lys His Arg Phe Leu Ser Ala Gln Ile Asp Ala
245 250 255

Tyr Leu Thr Asp Asp Leu Trp Leu Arg Asn Ala Arg Lys Ala Asn Ala
260 265 270

Ala Ala Gln Arg Leu Ala Gln Gly Leu Tyr Gly Ala Pro Gly Val Glu
275 280 285

Val Leu Gly Gly Thr Glu Ala Asn Ile Leu Phe Cys Arg Met Asp Ser
290 295 300

Pro Met Ile Asp Ala Leu Leu Lys Ala Gly Phe Lys Phe Gly Tyr Glu
305 310 315 320

Arg Trp Gly Pro Asn Val Val Arg Phe Val Thr Ser Phe Ala Thr Thr 325 330 335

Ala Glu Asp Val Asp His Leu Leu Asn Gln Val Arg Leu Ala Ala Asp
340 345 350

Arg Thr Gln Glu Arg
355

<210> SEQ ID NO 215
<211> LENGTH: 1071
<212> TYPE: DNA
<213> ORGANISM: Artificial sequence
<220> FEATURE:
<223> OTHER INFORMATION: Engineered sequence

<400> SEQUENCE: 215
atgaatggtg aaaccagtcg tccgccggca ctgggtttta gcagcgaaaa cattaatggc 60
gcaagtccgg aagttgcgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac cactggagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctggagggtg cgaaaggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 216
<211> LENGTH: 357
<212> TYPE: PRT
<213> ORGANISM: Artificial sequence
<220> FEATURE:
<223> OTHER INFORMATION: Engineered sequence

<400> SEQUENCE: 216

Met Asn Gly Glu Thr Ser Arg Pro Pro Ala Leu Gly Phe Ser Ser Glu
1 5 10 15

Asn Ile Asn Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

```
Thr Pro Pro Trp Gly Asn Ile Tyr Cys His His Trp Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Ala Lys Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 217
<211> LENGTH: 1071
<212> TYPE: DNA
<213> ORGANISM: Artificial sequence
<220> FEATURE:
<223> OTHER INFORMATION: Engineered sequence

<400> SEQUENCE: 217

atgaatggtg aaaccagtcg tccgccggca ctgggtttta gcagcgaaaa cattaatggc      60

gcaagtccgg aagttgcgca agcactggtt aaacatagca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480
```

```
gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctgcgtggtg cgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

```
<210> SEQ ID NO 218
<211> LENGTH: 357
<212> TYPE: PRT
<213> ORGANISM: Artificial sequence
<220> FEATURE:
<223> OTHER INFORMATION: Engineered sequence

<400> SEQUENCE: 218

Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255
```

```
Tyr Leu Thr Asp Asp Leu Trp Leu Arg Asn Ala Arg Lys Ala Asn Ala
            260                 265                 270

Ala Ala Gln Arg Leu Ala Gln Gly Leu Arg Gly Ala Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 219
<211> LENGTH: 1071
<212> TYPE: DNA
<213> ORGANISM: Artificial sequence
<220> FEATURE:
<223> OTHER INFORMATION: Engineered sequence

<400> SEQUENCE: 219

```
atgaatggtg aaaccagtcg tccgccggca ctgggtttta gcagcgaaaa cattaatggc     60

gcaagtccgg aagttgcgca agcactggtt aaacatagca gcggtcaagc tggtccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac aactggagcc atattaataa cgacgagtgc    300

ggcgcaccgg aatttttcag caacggcgcc aaactgatga ccgttgacgg tcgcgcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctgcgtggtg cgaaaggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

<210> SEQ ID NO 220
<211> LENGTH: 357
<212> TYPE: PRT
<213> ORGANISM: Artificial sequence
<220> FEATURE:
<223> OTHER INFORMATION: Engineered sequence

<400> SEQUENCE: 220

```
Met Asn Gly Glu Thr Ser Arg Pro Pro Ala Leu Gly Phe Ser Ser Glu
1               5                   10                  15
```

```
Asn Ile Asn Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His Asn Trp Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Arg Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Arg Gly Ala Lys Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 221
<211> LENGTH: 1071
<212> TYPE: DNA
<213> ORGANISM: Artificial sequence
<220> FEATURE:
<223> OTHER INFORMATION: Engineered sequence

<400> SEQUENCE: 221
atgaatggtg aaaccagtcg tccgccggca ctgggtttta gcagcgaaaa cattaatggc 60
gcaagtccgg aagttgcgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac aactggagcc atattaataa cgacgagtgc 300
ggcgcaccgg aatttttcag caacggcgcc aaactgatga ccgttgacgg tccggcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctgtatggtc tgaaaggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 222
<211> LENGTH: 357
<212> TYPE: PRT
<213> ORGANISM: Artificial sequence
<220> FEATURE:
<223> OTHER INFORMATION: Engineered sequence

<400> SEQUENCE: 222

Met Asn Gly Glu Thr Ser Arg Pro Pro Ala Leu Gly Phe Ser Ser Glu
1 5 10 15

Asn Ile Asn Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His Asn Trp Ser His Ile Asn
85 90 95

Asn Asp Glu Cys Gly Ala Pro Glu Phe Phe Ser Asn Gly Ala Lys Leu
100 105 110

Met Thr Val Asp Gly Pro Ala Ala Lys Leu Asp Ile Val Arg Leu Arg
115 120 125

Glu Arg Thr Ser Glu Lys Val Gly Asp Val His Thr Thr Gln Pro Ala
130 135 140

Cys Val Ser Ile Thr Gln Ala Thr Glu Val Gly Ser Ile Tyr Thr Leu
145 150 155 160

Asp Glu Ile Glu Ala Ile Gly Asp Val Cys Lys Ser Ser Ser Leu Gly
165 170 175

Leu His Met Asp Gly Ser Arg Phe Ala Asn Ala Leu Val Ser Leu Gly
180 185 190

```
Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Tyr Gly Leu Lys Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 223
<211> LENGTH: 1071
<212> TYPE: DNA
<213> ORGANISM: Artificial sequence
<220> FEATURE:
<223> OTHER INFORMATION: Engineered sequence

<400> SEQUENCE: 223

atgaatggtg aaaccagtcg tccgccggca ctgggtttta gcagcgaaaa cattaatggc      60

gcaagtccgg aagttgcgca agcactggtt aaacatagca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac cactggagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480

gacgaaatcg aagcgattgg cgacgtctgc aaaagtagta gtctgggcct gcatatggac     540

ggtagtcgtt ttgcgaacgc actggttagt ctgggttgtt ctccggcaga aatgacctgg     600

aaagcaggtg ttgacgcact gagttttggc gcaaccaaaa acggcgttct ggctgcagaa     660

gcaattgttc tgtttaacac cagcctggcc accgaaatga gctatcgtcg taaacgcgca     720

ggtcatctga ttagcaaaca tcgtttcctg agcgcacaga ttgacgcata tctgaccgac     780

gatctgtggc tgcgtaacgc acgtaaagca aacgcagcag cacaacgtct ggcacaaggt     840

ctgaagggtg cgccgggcgt tgaagttctg ggcggtaccg aagcaaacat tctgttctgc     900

cgtatggact ctccgatgat tgacgcactg ctgaaagcgg gctttaaatt tggctatgaa     960

cgctggggtc cgaacgttgt tcgttttgtc accagctttg caaccaccgc agaagacgtt    1020

gatcatctgc tgaaccaagt tcgtctggca gcagatcgta cccaagaacg t             1071
```

<210> SEQ ID NO 224
<211> LENGTH: 357
<212> TYPE: PRT
<213> ORGANISM: Artificial sequence
<220> FEATURE:
<223> OTHER INFORMATION: Engineered sequence

<400> SEQUENCE: 224

```
Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Trp Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Lys Gly Ala Pro Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 225
<211> LENGTH: 1071
<212> TYPE: DNA
<213> ORGANISM: Artificial sequence
<220> FEATURE:
<223> OTHER INFORMATION: Engineered sequence

<400> SEQUENCE: 225
atgaatggtg aaaccagtcg tccgccggca ctgggtttta gcagcgaaaa cattaatggc 60
gcaagtccgg aagttgcgca agcactggtt aaacatagca gcggtcaagc tggtccgtat 120
ggtatggatg aaattaccgc gcaggttaaa cgtaaattct gcgagatctt cgagcgcgac 180
gttgaagttt ttctggttcc gaccggtacc gctgctaacg cactgtgtct gtctgcaatg 240
accccgccgt ggggtaatat ttattgccac cactggagcc atattaataa cgacgagtgc 300
ggcgcaccgg aatttttcag caacggcgcc aaactgatga ccgttgacgg tggcgcagca 360
aaactggata ttgtacgtct gcgcgaacgt accagcgaaa aagttggcga cgttcatacc 420
acccaaccgg cttgcgttag tattacccag gcaaccgaag ttggtagcat ctataccctg 480
gacgaaatcg aagcgattgg cgacgtctgc aaaagtagta gtctgggcct gcatatggac 540
ggtagtcgtt ttgcgaacgc actggttagt ctgggttgtt ctccggcaga aatgacctgg 600
aaagcaggtg ttgacgcact gagttttggc gcaaccaaaa acggcgttct ggctgcagaa 660
gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctgtatggtg tgccgggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 226
<211> LENGTH: 357
<212> TYPE: PRT
<213> ORGANISM: Artificial sequence
<220> FEATURE:
<223> OTHER INFORMATION: Engineered sequence

<400> SEQUENCE: 226

Met Asn Gly Glu Thr Ser Arg Pro Pro Ala Leu Gly Phe Ser Ser Glu
1 5 10 15

Asn Ile Asn Gly Ala Ser Pro Glu Val Ala Gln Ala Leu Val Lys His
20 25 30

Ser Ser Gly Gln Ala Gly Pro Tyr Gly Met Asp Glu Ile Thr Ala Gln
35 40 45

Val Lys Arg Lys Phe Cys Glu Ile Phe Glu Arg Asp Val Glu Val Phe
50 55 60

Leu Val Pro Thr Gly Thr Ala Ala Asn Ala Leu Cys Leu Ser Ala Met
65 70 75 80

Thr Pro Pro Trp Gly Asn Ile Tyr Cys His His Trp Ser His Ile Asn
85 90 95

Asn Asp Glu Cys Gly Ala Pro Glu Phe Phe Ser Asn Gly Ala Lys Leu
100 105 110

Met Thr Val Asp Gly Gly Ala Ala Lys Leu Asp Ile Val Arg Leu Arg

```
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Tyr Gly Val Pro Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 227
<211> LENGTH: 1071
<212> TYPE: DNA
<213> ORGANISM: Artificial sequence
<220> FEATURE:
<223> OTHER INFORMATION: Engineered sequence

<400> SEQUENCE: 227

atgaatggtg aaaccagtcg tccgccggca ctgggtttta gcagcgaaaa cattaatggc      60

gcaagtccgg aagttgcgca agcactggtt aaacatagca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac cactggagcc atattaataa cgacgagtgc     300

ggcgcaccgg aatttttcag caacggcgcc aaactgatga ccgttgacgg tccggcagca     360

aaactggata ttgtacgtct gcgcgaacgt accagcgaaa aagttggcga cgttcatacc     420

acccaaccgg cttgcgttag tattacccag gcaaccgaag ttggtagcat ctataccctg     480

gacgaaatcg aagcgattgg cgacgtctgc aaaagtagta gtctgggcct gcatatggac     540

ggtagtcgtt ttgcgaacgc actggttagt ctgggttgtt ctccggcaga aatgacctgg     600

aaagcaggtg ttgacgcact gagttttggc gcaaccaaaa acggcgttct ggctgcagaa     660
```

gcaattgttc tgtttaacac cagcctggcc accgaaatga gctatcgtcg taaacgcgca 720
ggtcatctga ttagcaaaca tcgtttcctg agcgcacaga ttgacgcata tctgaccgac 780
gatctgtggc tgcgtaacgc acgtaaagca aacgcagcag cacaacgtct ggcacaaggt 840
ctgtatggtg cgccgggcgt tgaagttctg ggcggtaccg aagcaaacat tctgttctgc 900
cgtatggact ctccgatgat tgacgcactg ctgaaagcgg gctttaaatt tggctatgaa 960
cgctggggtc cgaacgttgt tcgttttgtc accagctttg caaccaccgc agaagacgtt 1020
gatcatctgc tgaaccaagt tcgtctggca gcagatcgta cccaagaacg t 1071

<210> SEQ ID NO 228
<211> LENGTH: 357
<212> TYPE: PRT
<213> ORGANISM: Artificial sequence
<220> FEATURE:
<223> OTHER INFORMATION: Engineered sequence

<400> SEQUENCE: 228

Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Trp Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Tyr Gly Ala Pro Gly Val Glu
        275                 280                 285

Val Leu Gly Gly Thr Glu Ala Asn Ile Leu Phe Cys Arg Met Asp Ser

```
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355


<210> SEQ ID NO 229
<211> LENGTH: 1071
<212> TYPE: DNA
<213> ORGANISM: Artificial sequence
<220> FEATURE:
<223> OTHER INFORMATION: Engineered sequence

<400> SEQUENCE: 229

atgaatggtg aaaccagtcg tccgccggca ctgggtttta gcagcgaaaa cattaatggc     60

gcaagtccgg aagttgcgca agcactggtt aaacatagca gcggtcaagc tagcccgtat    120

ggtatggatg aaattaccgc gcaggttaaa cgtaaattct gcgagatctt cgagcgcgac    180

gttgaagttt ttctggttcc gaccggtacc gctgctaacg cactgtgtct gtctgcaatg    240

accccgccgt ggggtaatat ttattgccac catgcaagcc atattaataa cgacgagtgc    300

ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct gtccgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatatctggc tgcgtaacgc acgtaaagca aacgcagcag cacaacgtct ggcacaaggt    840

ctggaaggtc tgggcggcgt tgaagttctg tggaaaaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071


<210> SEQ ID NO 230
<211> LENGTH: 357
<212> TYPE: PRT
<213> ORGANISM: Artificial sequence
<220> FEATURE:
<223> OTHER INFORMATION: Engineered sequence

<400> SEQUENCE: 230

Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys His
            20                  25                  30

Ser Ser Gly Gln Ala Ser Pro Tyr Gly Met Asp Glu Ile Thr Ala Gln
        35                  40                  45
```

```
Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ser Ala Glu Ala Ile Val Leu
    210                 215                 220

Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Ile Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Trp Lys Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

```
<210> SEQ ID NO 231
<211> LENGTH: 1071
<212> TYPE: DNA
<213> ORGANISM: Artificial sequence
<220> FEATURE:
<223> OTHER INFORMATION: Engineered sequence

<400> SEQUENCE: 231

atgaatggtg aaaccagtcg tccgccggca ctgggtttta gcagcgaaaa cattaatggc      60

gcaagtccgg aagttgcgca agcactggtt aaacatagca gcggtcaagc tggtccgtat     120

ggtatggatg aaattaccgc gcaggttaaa cgtaaattct gcgagatctt cgagcgcgac     180

gttgaagttt ttctggttcc gaccggtacc gctgctaacg cactgtgtct gtctgcaatg     240

accccgccgt ggggtaatat ttattgccac catgcaagcc atattaataa cgacgagtgc     300
```

```
ggcgcaccgg aatttttcag caacggcgcc aaactgatga ccgttgacgg tccggcagca    360

aaactggata ttgtacgtct gcgcgaacgt accagcgaaa aagttggcga cgttcatacc    420

acccaaccgg cttgcgttag tattacccag gcaaccgaag ttggtagcat ctataccctg    480

gacgaaatcg aagcgattgg cgacgtctgc aaaagtagta gtctgggcct gcatatggac    540

ggtagtcgtt ttgcgaacgc actggttagt ctgggttgtt ctccggcaga aatgacctgg    600

aaagcaggtg ttgacgcact gagttttggc gcaaccaaaa acggcgttct ggctgcagaa    660

gcaattgttc tgtttaacac cagcctggcc accgaaatga gctatcgtcg taaacgcgca    720

ggtcatctga ttagcaaaca tcgtttcctg agcgcacaga ttgacgcata tctgaccgac    780

gatctgtggc tgcgtaacgc acgtaaagca aacgcagcag cacaacgtct ggcacaaggt    840

ctggaaggtc tgggcggcgt tgaagttctg ggcggtaccg aagcaaacat tctgttctgc    900

cgtatggact ctccgatgat tgacgcactg ctgaaagcgg gctttaaatt tggctatgaa    960

cgctggggtc cgaacgttgt tcgttttgtc accagctttg caaccaccgc agaagacgtt   1020

gatcatctgc tgaaccaagt tcgtctggca gcagatcgta cccaagaacg t            1071
```

```
<210> SEQ ID NO 232
<211> LENGTH: 357
<212> TYPE: PRT
<213> ORGANISM: Artificial sequence
<220> FEATURE:
<223> OTHER INFORMATION: Engineered sequence

<400> SEQUENCE: 232

Met Asn Gly Glu Thr Ser Arg Pro Pro Ala Leu Gly Phe Ser Ser Glu
1               5                   10                  15

Asn Ile Asn Gly Ala Ser Pro Glu Val Ala Gln Ala Leu Val Lys His
            20                  25                  30

Ser Ser Gly Gln Ala Gly Pro Tyr Gly Met Asp Glu Ile Thr Ala Gln
        35                  40                  45

Val Lys Arg Lys Phe Cys Glu Ile Phe Glu Arg Asp Val Glu Val Phe
    50                  55                  60

Leu Val Pro Thr Gly Thr Ala Ala Asn Ala Leu Cys Leu Ser Ala Met
65                  70                  75                  80

Thr Pro Pro Trp Gly Asn Ile Tyr Cys His His Ala Ser His Ile Asn
                85                  90                  95

Asn Asp Glu Cys Gly Ala Pro Glu Phe Phe Ser Asn Gly Ala Lys Leu
            100                 105                 110

Met Thr Val Asp Gly Pro Ala Ala Lys Leu Asp Ile Val Arg Leu Arg
        115                 120                 125

Glu Arg Thr Ser Glu Lys Val Gly Asp Val His Thr Thr Gln Pro Ala
    130                 135                 140

Cys Val Ser Ile Thr Gln Ala Thr Glu Val Gly Ser Ile Tyr Thr Leu
145                 150                 155                 160

Asp Glu Ile Glu Ala Ile Gly Asp Val Cys Lys Ser Ser Ser Leu Gly
                165                 170                 175

Leu His Met Asp Gly Ser Arg Phe Ala Asn Ala Leu Val Ser Leu Gly
            180                 185                 190

Cys Ser Pro Ala Glu Met Thr Trp Lys Ala Gly Val Asp Ala Leu Ser
        195                 200                 205

Phe Gly Ala Thr Lys Asn Gly Val Leu Ala Ala Glu Ala Ile Val Leu
    210                 215                 220
```

-continued

```
Phe Asn Thr Ser Leu Ala Thr Glu Met Ser Tyr Arg Arg Lys Arg Ala
225                 230                 235                 240

Gly His Leu Ile Ser Lys His Arg Phe Leu Ser Ala Gln Ile Asp Ala
                245                 250                 255

Tyr Leu Thr Asp Asp Leu Trp Leu Arg Asn Ala Arg Lys Ala Asn Ala
            260                 265                 270

Ala Ala Gln Arg Leu Ala Gln Gly Leu Glu Gly Leu Gly Gly Val Glu
        275                 280                 285

Val Leu Gly Gly Thr Glu Ala Asn Ile Leu Phe Cys Arg Met Asp Ser
    290                 295                 300

Pro Met Ile Asp Ala Leu Leu Lys Ala Gly Phe Lys Phe Gly Tyr Glu
305                 310                 315                 320

Arg Trp Gly Pro Asn Val Val Arg Phe Val Thr Ser Phe Ala Thr Thr
                325                 330                 335

Ala Glu Asp Val Asp His Leu Leu Asn Gln Val Arg Leu Ala Ala Asp
            340                 345                 350

Arg Thr Gln Glu Arg
        355
```

<210> SEQ ID NO 233
<211> LENGTH: 1059
<212> TYPE: DNA
<213> ORGANISM: Artificial sequence
<220> FEATURE:
<223> OTHER INFORMATION: Engineered sequence

<400> SEQUENCE: 233

```
atgagtcgtc cgccggcact gggttttagc agcgaaaaca ttaatggcgc aagtccggaa      60

gttgcgcaag cactggttaa acatagcagc ggtcaagctg gtccgtatgg tatggatgaa     120

attaccgcgc aggttaaacg taaattctgc gagatcttcg agcgcgacgt tgaagttttt     180

ctggttccga ccggtaccgc tgctaacgca ctgtgtctgt ctgcaatgac cccgccgtgg     240

ggtaatattt attgccacca tgcaagccat attaataacg acgagtgcgg cgcaccggaa     300

tttttcagca acggcgccaa actgatgacc gttgacggtc cggcagcaaa actggatatt     360

gtacgtctgc gcgaacgtac cagcgaaaaa gttggcgacg ttcataccac ccaaccggct     420

tgcgttagta ttacccaggc aaccgaagtt ggtagcatct ataccctgga cgaaatcgaa     480

gcgattggcg acgtctgcaa aagtagtagt ctgggcctgc atatggacgg tagtcgtttt     540

gcgaacgcac tggttagtct gggttgttct ccggcagaaa tgacctggaa agcaggtgtt     600

gacgcactga gttttggcgc aaccaaaaac ggcgttctgg ctgcagaagc aattgttctg     660

tttaacacca gcctggccac cgaaatgagc tatcgtcgta aacgcgcagg tcatctgatt     720

agcaaacatc gtttcctgag cgcacagatt gacgcatatc tgaccgacga tctgtggctg     780

cgtaacgcac gtaaagcaaa cgcagcagca caacgtctgg cacaaggtct ggaaggtctg     840

ggcggcgttg aagttctggg cggtaccgaa gcaaacattc tgttctgccg tatggactct     900

ccgatgattg acgcactgct gaaagcgggc tttaaatttg gctatgaacg ctggggtccg     960

aacgttgttc gttttgtcac cagctttgca accaccgcag aagacgttga tcatctgctg    1020

aaccaagttc gtctggcagc agatcgtacc caagaacgt                           1059
```

<210> SEQ ID NO 234
<211> LENGTH: 353
<212> TYPE: PRT
<213> ORGANISM: Artificial sequence
<220> FEATURE:

<223> OTHER INFORMATION: Engineered sequence

<400> SEQUENCE: 234

Met Ser Arg Pro Pro Ala Leu Gly Phe Ser Ser Glu Asn Ile Asn Gly
1 5 10 15

Ala Ser Pro Glu Val Ala Gln Ala Leu Val Lys His Ser Ser Gly Gln
20 25 30

Ala Gly Pro Tyr Gly Met Asp Glu Ile Thr Ala Gln Val Lys Arg Lys
35 40 45

Phe Cys Glu Ile Phe Glu Arg Asp Val Glu Val Phe Leu Val Pro Thr
50 55 60

Gly Thr Ala Ala Asn Ala Leu Cys Leu Ser Ala Met Thr Pro Pro Trp
65 70 75 80

Gly Asn Ile Tyr Cys His His Ala Ser His Ile Asn Asn Asp Glu Cys
85 90 95

Gly Ala Pro Glu Phe Phe Ser Asn Gly Ala Lys Leu Met Thr Val Asp
100 105 110

Gly Pro Ala Ala Lys Leu Asp Ile Val Arg Leu Arg Glu Arg Thr Ser
115 120 125

Glu Lys Val Gly Asp Val His Thr Thr Gln Pro Ala Cys Val Ser Ile
130 135 140

Thr Gln Ala Thr Glu Val Gly Ser Ile Tyr Thr Leu Asp Glu Ile Glu
145 150 155 160

Ala Ile Gly Asp Val Cys Lys Ser Ser Ser Leu Gly Leu His Met Asp
165 170 175

Gly Ser Arg Phe Ala Asn Ala Leu Val Ser Leu Gly Cys Ser Pro Ala
180 185 190

Glu Met Thr Trp Lys Ala Gly Val Asp Ala Leu Ser Phe Gly Ala Thr
195 200 205

Lys Asn Gly Val Leu Ala Ala Glu Ala Ile Val Leu Phe Asn Thr Ser
210 215 220

Leu Ala Thr Glu Met Ser Tyr Arg Arg Lys Arg Ala Gly His Leu Ile
225 230 235 240

Ser Lys His Arg Phe Leu Ser Ala Gln Ile Asp Ala Tyr Leu Thr Asp
245 250 255

Asp Leu Trp Leu Arg Asn Ala Arg Lys Ala Asn Ala Ala Ala Gln Arg
260 265 270

Leu Ala Gln Gly Leu Glu Gly Leu Gly Gly Val Glu Val Leu Gly Gly
275 280 285

Thr Glu Ala Asn Ile Leu Phe Cys Arg Met Asp Ser Pro Met Ile Asp
290 295 300

Ala Leu Leu Lys Ala Gly Phe Lys Phe Gly Tyr Glu Arg Trp Gly Pro
305 310 315 320

Asn Val Val Arg Phe Val Thr Ser Phe Ala Thr Thr Ala Glu Asp Val
325 330 335

Asp His Leu Leu Asn Gln Val Arg Leu Ala Ala Asp Arg Thr Gln Glu
340 345 350

Arg

<210> SEQ ID NO 235
<211> LENGTH: 1056
<212> TYPE: DNA
<213> ORGANISM: Artificial sequence
<220> FEATURE:
<223> OTHER INFORMATION: Engineered sequence

<400> SEQUENCE: 235

```
atgcgtccgc cggcactggg ttttagcagc gaaaacatta atggcgcaag tccggaagtt      60
gcgcaagcac tggttaaaca tagcagcggt caagctggtc cgtatggtat ggatgaaatt     120
accgcgcagg ttaaacgtaa attctgcgag atcttcgagc gcgacgttga agtttttctg     180
gttccgaccg gtaccgctgc taacgcactg tgtctgtctg caatgacccc gccgtggggt     240
aatatttatt gccaccatgc aagccatatt aataacgacg agtgcggcgc accggaattt     300
ttcagcaacg gcgccaaact gatgaccgtt gacggtccgg cagcaaaact ggatattgta     360
cgtctgcgcg aacgtaccag cgaaaaagtt ggcgacgttc ataccaccca accggcttgc     420
gttagtatta cccaggcaac cgaagttggt agcatctata ccctggacga aatcgaagcg     480
attggcgacg tctgcaaaag tagtagtctg ggcctgcata tggacggtag tcgttttgcg     540
aacgcactgg ttagtctggg ttgttctccg gcagaaatga cctggaaagc aggtgttgac     600
gcactgagtt ttggcgcaac caaaaacggc gttctggctg cagaagcaat tgttctgttt     660
aacaccagcc tggccaccga aatgagctat cgtcgtaaac gcgcaggtca tctgattagc     720
aaacatcgtt tcctgagcgc acagattgac gcatatctga ccgacgatct gtggctgcgt     780
aacgcacgta aagcaaacgc agcagcacaa cgtctggcac aaggtctgga aggtctgggc     840
ggcgttgaag ttctgggcgg taccgaagca aacattctgt tctgccgtat ggactctccg     900
atgattgacg cactgctgaa agcgggcttt aaatttggct atgaacgctg ggtccgaac      960
gttgttcgtt ttgtcaccag ctttgcaacc accgcagaag acgttgatca tctgctgaac    1020
caagttcgtc tggcagcaga tcgtacccaa gaacgt                              1056
```

<210> SEQ ID NO 236
<211> LENGTH: 352
<212> TYPE: PRT
<213> ORGANISM: Artificial sequence
<220> FEATURE:
<223> OTHER INFORMATION: Engineered sequence

<400> SEQUENCE: 236

```
Met Arg Pro Pro Ala Leu Gly Phe Ser Ser Glu Asn Ile Asn Gly Ala
1               5                   10                  15

Ser Pro Glu Val Ala Gln Ala Leu Val Lys His Ser Ser Gly Gln Ala
            20                  25                  30

Gly Pro Tyr Gly Met Asp Glu Ile Thr Ala Gln Val Lys Arg Lys Phe
        35                  40                  45

Cys Glu Ile Phe Glu Arg Asp Val Glu Val Phe Leu Val Pro Thr Gly
    50                  55                  60

Thr Ala Ala Asn Ala Leu Cys Leu Ser Ala Met Thr Pro Pro Trp Gly
65                  70                  75                  80

Asn Ile Tyr Cys His His Ala Ser His Ile Asn Asn Asp Glu Cys Gly
                85                  90                  95

Ala Pro Glu Phe Phe Ser Asn Gly Ala Lys Leu Met Thr Val Asp Gly
            100                 105                 110

Pro Ala Ala Lys Leu Asp Ile Val Arg Leu Arg Glu Arg Thr Ser Glu
        115                 120                 125

Lys Val Gly Asp Val His Thr Thr Gln Pro Ala Cys Val Ser Ile Thr
    130                 135                 140

Gln Ala Thr Glu Val Gly Ser Ile Tyr Thr Leu Asp Glu Ile Glu Ala
145                 150                 155                 160
```

-continued

| | | | | | | | | | | | | | | | |
|---|---|---|---|---|---|---|---|---|---|---|---|---|---|---|---|
| Ile | Gly | Asp | Val | Cys | Lys | Ser | Ser | Ser | Leu | Gly | Leu | His | Met | Asp | Gly |
| | | | | 165 | | | | | 170 | | | | | 175 | |
| Ser | Arg | Phe | Ala | Asn | Ala | Leu | Val | Ser | Leu | Gly | Cys | Ser | Pro | Ala | Glu |
| | | | 180 | | | | | 185 | | | | | 190 | | |
| Met | Thr | Trp | Lys | Ala | Gly | Val | Asp | Ala | Leu | Ser | Phe | Gly | Ala | Thr | Lys |
| | | 195 | | | | | 200 | | | | | 205 | | | |
| Asn | Gly | Val | Leu | Ala | Ala | Glu | Ala | Ile | Val | Leu | Phe | Asn | Thr | Ser | Leu |
| | 210 | | | | | 215 | | | | | 220 | | | | |
| Ala | Thr | Glu | Met | Ser | Tyr | Arg | Arg | Lys | Arg | Ala | Gly | His | Leu | Ile | Ser |
| 225 | | | | | 230 | | | | | 235 | | | | | 240 |
| Lys | His | Arg | Phe | Leu | Ser | Ala | Gln | Ile | Asp | Ala | Tyr | Leu | Thr | Asp | Asp |
| | | | | 245 | | | | | 250 | | | | | 255 | |
| Leu | Trp | Leu | Arg | Asn | Ala | Arg | Lys | Ala | Asn | Ala | Ala | Ala | Gln | Arg | Leu |
| | | | 260 | | | | | 265 | | | | | 270 | | |
| Ala | Gln | Gly | Leu | Glu | Gly | Leu | Gly | Gly | Val | Glu | Val | Leu | Gly | Gly | Thr |
| | | 275 | | | | | 280 | | | | | 285 | | | |
| Glu | Ala | Asn | Ile | Leu | Phe | Cys | Arg | Met | Asp | Ser | Pro | Met | Ile | Asp | Ala |
| | 290 | | | | | 295 | | | | | 300 | | | | |
| Leu | Leu | Lys | Ala | Gly | Phe | Lys | Phe | Gly | Tyr | Glu | Arg | Trp | Gly | Pro | Asn |
| 305 | | | | | 310 | | | | | 315 | | | | | 320 |
| Val | Val | Arg | Phe | Val | Thr | Ser | Phe | Ala | Thr | Thr | Ala | Glu | Asp | Val | Asp |
| | | | | 325 | | | | | 330 | | | | | 335 | |
| His | Leu | Leu | Asn | Gln | Val | Arg | Leu | Ala | Ala | Asp | Arg | Thr | Gln | Glu | Arg |
| | | | 340 | | | | | 345 | | | | | 350 | | |